United States Patent [19]

Allen et al.

[11] Patent Number: 5,252,574
[45] Date of Patent: Oct. 12, 1993

[54] ANGIOTENSIN II ANTAGONISTS INCORPORATING A SUBSTITUTED THIOPHENE OR FURAN

[75] Inventors: Eric E. Allen, Somerset; Nancy Kevin, Clifton; Tomasz W. Glinka, Scotch Plains; Ralph A. Rivero, Tinton Falls, all of N.J.

[73] Assignee: Merck & Co., Inc., Rahway, N.J.

[21] Appl. No.: 846,152

[22] Filed: Mar. 11, 1992

Related U.S. Application Data

[63] Continuation-in-part of Ser. No. 691,911, Apr. 26, 1991, abandoned.

[51] Int. Cl.$^5$ .................. A61K 31/505; C07D 239/95; C07D 239/88; C07D 239/93
[52] U.S. Cl. ...................................... 514/259; 514/260; 544/283; 544/284; 544/287; 544/288
[58] Field of Search ............... 544/283, 284, 287, 288; 514/259, 260

[56] References Cited

U.S. PATENT DOCUMENTS

| | | |
|---|---|---|
| 4,753,944 | 6/1988 | Wright, Jr. et al. ................. 514/259 |
| 4,880,804 | 11/1989 | Carini et al. ....................... 514/234.5 |

FOREIGN PATENT DOCUMENTS

| | | |
|---|---|---|
| A58696/90 | 7/1989 | Australia . |
| 0260613 | 9/1987 | European Pat. Off. . |
| 0323841 | 1/1989 | European Pat. Off. . |
| 0324377 | 1/1989 | European Pat. Off. . |
| 0392317 | 4/1990 | European Pat. Off. . |
| 0399731 | 5/1990 | European Pat. Off. . |
| 0399732 | 5/1990 | European Pat. Off. . |
| 0400974 | 5/1990 | European Pat. Off. . |
| 0403158 | 6/1990 | European Pat. Off. . |
| 0403159 | 6/1990 | European Pat. Off. . |
| 0411766 | 6/1990 | European Pat. Off. . |
| 0409332 | 7/1990 | European Pat. Off. . |
| 0412594 | 7/1990 | European Pat. Off. . |
| 0415886 | 8/1990 | European Pat. Off. . |
| 0419048 | 8/1990 | European Pat. Off. . |
| 0429257 | 11/1990 | European Pat. Off. . |
| 0434249 | 11/1990 | European Pat. Off. . |
| 0430709 | 6/1991 | European Pat. Off. . |
| 0465323A1 | 6/1991 | European Pat. Off. . |
| 0468372 | 7/1991 | European Pat. Off. . |
| 0480204 | 9/1991 | European Pat. Off. . |

OTHER PUBLICATIONS

U.S. Ser. No. 07/744,565, Aug. 1991, Greenlee et al.
U.S. Ser. No. 07/744,554, Aug. 1991, Greenlee et al.
U.S. Ser. No. 07/744,138, Aug. 1991, Greenlee et al.
U.S. Ser. No. 07/671,597, Apr. 1991, Chakravarty et al.
U.S. Ser. No. 07/681,793, Apr. 1991, Bagley et al.
U.S. Ser. No. 07/846,152, Mar. 1992, Allen et al.
U.S. Ser. No. 07/744,557, Aug. 1991, Greenlee et al.
U.S. Ser. No. 07/846,151, Mar. 1992, Allen et al.
U.S. Ser. No. 07/674,836, Mar. 1991, Chakravarty et al.
U.S. Ser. No. 07/697,169, May 1991, Chakravarty et al.

*Primary Examiner*—Mukund J. Shah
*Assistant Examiner*—Matthew V. Grumbling
*Attorney, Agent, or Firm*—Joseph F. DiPrima; Valerie J. Camara

[57] ABSTRACT

Substituted heterocycles attached through a methylene bridge to novel substituted phenyl thiophene or phenyl furan derivative of the Formula I are useful as angiotensin II antagonists.

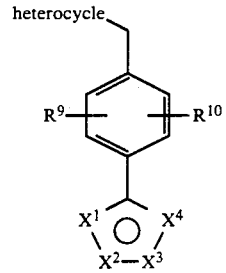

11 Claims, No Drawings

ANGIOTENSIN II ANTAGONISTS INCORPORATING A SUBSTITUTED THIOPHENE OR FURAN

BACKGROUND OF THE INVENTION

The present application is a continuation in part of U.S. Ser. No. 07/691,911 filed on Apr. 26, 1991 now abandoned.

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is antiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens,* A4, 27-46 (1982); D. H. P. Streeten and G. H. Anderson, Jr.—*Handbook of Hypertension, Clinical Pharmacology of Antihypertensive Drugs,* ed. A. E. Doyle, Vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804 and in European Patent Applications 028,834; 234,637; 253,310; and 291,969; and articles by A. T. Chiu, et al. [*Eur. J. Pharm. Exp. Therap,* 157, 13-21 (1988)] and by P. C. Wong, et al. [*J. Pharm. Exp. Therap,* 247, 1-7 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in any U.S. Patent, European Applications or literature publication are of the type containing substituted heterocycles bonded through an alkyl bridge to a novel substituted phenyl thiophene or phenyl furan of the type disclosed herein. The quinazolin-4(1H)-ones, triazolinones, triazolinimines, and pyrimidinones have been disclosed in earlier U.S. Patent applications focusing on the heterocyclic fragment of the antagonist design. The Ser. Nos. of these applications are 351,508; 358,971; 375,655; 360,673; 375,217; and 386,328. A related application U.S. Ser. No. 675,371, filed Mar. 26, 1991, discloses 6-membered ring fused imidazoles incorporating a thiophene or furan moiety.

BRIEF DESCRIPTION OF THE INVENTION

This invention is directed to substituted heterocycles attached through a methylene bridge to novel substituted phenylthiophene or phenylfuran derivative to give compounds of the Formula I, which are angiotensin II antagonists and are useful in the treatment of hypertension and congestive heart failure. The compounds of the invention are useful as ocular antihypertensives.

Specifically, the compounds of this invention contain a heterocyclic moiety which is substituted at the specified positions and to which is methylene bridge connecting a novel substituted phenylthiophene or phenylfuran group as defined by the lower portion of Formula I, is attached. Additionally, pharmaceutically acceptable compositions of these novel compounds, as the sole therapeutically active ingredient and in combination with diuretics and other antihypertensive agents, including beta blockers, angiotensin converting enzyme inhibitors, calcium channel blockers or a combination thereof are disclosed and claimed. Further, methods of treating hypertension and congestive heart failure are described and claimed.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

DETAILED DESCRIPTION OF THE INVENTION

This invention relates to compounds of the general Formula I:

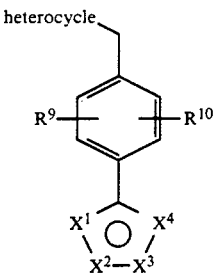

and the heterocycle is specifically defined as:

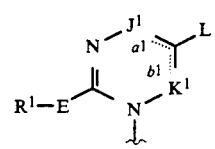

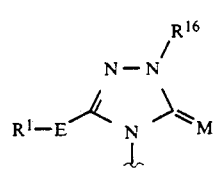

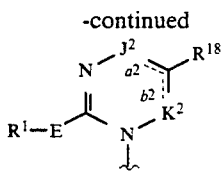

R[1] is:
(a) ($C_1$–$C_6$)-alkyl, ($C_2$–$C_6$)-alkenyl or ($C_2$–$C_6$)-alkynyl each of which is unsubstituted or substituted with a substituent selected from the group consisting of:
  i) aryl as defined below,
  ii) ($C_3$–$C_7$)-cycloalkyl,
  iii) Cl, Br, I, F,
  iv) OH,
  v) $NH_2$,
  vi) $NH(C_1$–$C_4)$-alkyl,
  vii) $N[(C_1$–$C_4)$-alkyl$]_2$,
  viii) $NHSO_2R^2$,
  ix) $CF_3$,
  x) $COOR^2$, or
  xi) $SO_2NHR^{2a}$;
(b) aryl, wherein aryl is defined as phenyl or naphthyl, unsubstituted or substituted with 1 or 2 substituents selected from the group consisting of:
  i) Br, I, Cl, F,
  ii) ($C_1$–$C_4$)-alkyl,
  iii) ($C_1$–$C_4$)-alkoxy,
  iv) $NO_2$
  v) $CF_3$
  vi) $SO_2NR^{2a}R^{2a}$,
  vii) ($C_1$–$C_4$)-alkylthio,
  viii) hydroxy,
  ix) amino,
  x) ($C_3$–$C_7$)-cycloalkyl, or
  xi) ($C_3$–$C_{10}$)-alkenyl;
(c) heteroaryl, wherein heteroaryl is defined as a 5- or 6-membered heteroaromatic moiety, which can contain one or two members selected from the group consisting of N, O, S and wherein the heteroaryl is unsubstituted, monosubstituted or disubstituted with substituents selected from the group consisting of:
  i) Cl, Br, I, or F,
  ii) OH,
  iii) SH,
  iv) $NO_2$,
  v) ($C_1$–$C_4$)-alkyl,
  vi) ($C_2$–$C_4$)-alkenyl,
  vii) ($C_2$–$C_4$)-alkynyl,
  viii) ($C_1$–$C_4$)-alkoxy, or
  ix) $CF_3$, or
(d) ($C_1$–$C_4$)-polyfluoroalkyl;
E is:
(a) a single bond,
(b) —S(O)$_n$(CH$_2$)$_s$—, or
(c) —O—;
n is 0 to 2;
s is 0 to 5;
$J^1$ is (a) —C(=M)—, (b) $J^1$ and L are connected together to form a 6-carbon aromatic ring substituted with R[7a], R[7b], R[8a] and R[8b] or (c) $J^1$ and L are connected together to form a 6-membered aromatic ring containing one nitrogen atom not at $J^1$, substituted with R[7a], R[8a] and R[8b];

$K^1$ is (a) —C(=M)—, (b) $K^1$ and L are connected together to form a 6-carbon aromatic ring substituted with R[7a], R[7b], R[8a] and R[8b], or (c) $K^1$ and L are connected together to form a 6-membered aromatic ring containing one nitrogen atom, substituted on the carbon atoms with R[7a], R[8a] and R[8b];
one of a[1] or b[1] is a double bond in structures Ia provided that when $J^1$ is —C(=M)— then b[1] is a double bond and when $K^1$ is —C(=M)— then a[1] is a double bond;
L is the point of attachment of the 6-membered fused aromatic ring optionally containing one nitrogen atom;
$J^2$ is (a) —C(=M)—, or (b) —C(R[17])—;
$K^2$ is (a) —C(=M)—, or (b) —C(R[17])—, provided that one and only one of $J^2$ and $K^2$ is —C(=M)—;
one of a[2] or b[2] is a double bond in structure Ic provided that when $J^2$ is —C(=M)— then b[2] is a double bond and when $K^2$ is —C(=M)— then a[2] is a double bond.
M is O, S or NR[15];
R[2] is:
(a) H, or
(b) ($C_1$–$C_6$)-alkyl;
R[2a] is:
(a) R[2],
(b) $CH_2$-aryl, or
(c) aryl;
R[2b] is:
(a) R[2a], or
(b) $C_3$–$C_7$ cycloalkyl;
R[2c] is:
(a) —$SO_2$—($C_1$–$C_6$)-alkyl,
(b) —CO—($C_1$–$C_6$)-alkyl,
(c) —$SO_2$—($C_3$–$C_6$)-cycloalkyl,
(d) —CO—($C_3$–$C_6$)-cycloalkyl,
(e) —$SO_2$—($C_1$–$C_4$)-polyfluoroalkyl,
(f) —CO-aryl,
(g) —CO-polyfluoroaryl,
(h) —CO—(2- or 3-thienyl),
(i) —$SO_2$—(2- or 3-thienyl),
(j) —CO—(2-, 3- or 4-pyridyl),
(k) —CONH—($C_1$–$C_6$)-alkyl,
(l) —CON[($C_1$–$C_6$)alkyl]$_2$,
(m) —$CO_2$-($C_1$–$C_6$)-alkyl, or
(n) —$CO_2$—($C_3$–$C_6$)cycloalkyl;
R[7a] and R[7b] are independently
(a) H,
(b) ($C_1$–$C_6$)-alkyl, ($C_2$–$C_6$)-alkenyl or ($C_2$–$C_6$)-alkynyl,
(c) Cl, Br, I, F,
(d) $CF_3$, or
(e) when R[7a] and R[7b] are bonded to adjacent carbon atoms, they can be joined to form a phenyl ring;
R[8a] and R[8b] are independently
(a) H,
(b) aryl-($C_1$–$C_4$)-alkyl,
(c) heteroaryl-($C_1$–$C_4$)-alkyl,
(d) ($C_1$–$C_6$)-alkyl, which is unsubstituted or substituted with a substituent selected from the group consisting of: —CON(R[2a])$_2$, -heteroaryl, —S(O)$_n$R[21], -tetrazol-5-yl, —CONHSO$_2$R[21], —SO$_2$NH-heteroaryl, —SO$_2$NHCOR[21], —PO(OR[2])$_2$, —PO(OR[2a])$_2$, —SO$_2$NH—CN, —NR[2a]COOR[21], —OH, —NH$_2$, guanidino, ($C_1$–$C_4$)-alkoxy, ($C_1$–$C_4$)-alkylthio, ($C_1$–$C_4$)-alkylamino, ($C_1$–$C_4$)-dialkylamino, —COOR$^{2a}$, —CONHR$^{2a}$, —O—COR$^{2a}$, aryl, or

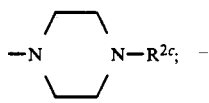

(e) —CO-aryl,
(f) ($C_3$–$C_7$)-cycloalkyl,
(g) Cl, Br, I, F,
(h) —OH,
(i) —OR$^{21}$,
(j) —SH,
(k) —S(O)$_n$—($C_1$–$C_4$)-alkyl,
(l) —COR$^{2a}$,
(m) —CO$_2$H,
(n) —SO$_3$H,
(o) —NR$^{2a}$R$^{21}$,
(p) —NR$^{2a}$COR$^{21}$,
(q) —NR$^{2a}$COOR$^{21}$,
(r) —SO$_2$NHR$^{2a}$,
(s) —SO$_2$NR$^2$R$^{2a}$,
(t) —NO$_2$,
(u) —NHSO$_2$CF$_3$,
(v) —CONR$^{2a}$R$^{21}$,
(w) —($C_1$–$C_4$)-polyfluoroalkyl,
(x) —COOR$^2$,
(y) —SO$_3$H,
(z) —N(R$^{2a}$)SO$_2$R$^{21}$,
(aa) —NR$^{2a}$CONR$^{2b}$R$^{21}$,
(bb) —OC(=O)NR$^{21}$R$^{2a}$,
(cc) -aryl,
(dd) —NHSO$_2$CF$_3$,
(ee) —SO$_2$NH-heteroaryl,
(ff) —SO$_2$NHCOR$^{21}$,
(gg) —CONHSO$_2$R$^{21}$,
(hh) —PO(OR$^2$)$_2$,
(ii) -tetrazol-5-yl,
(jj) —CONH(tetrazol-5-yl),
(kk) —SO$_2$NHCN,
(ll) -heteroaryl, (mm) 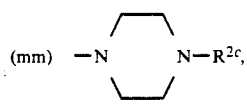

(nn) 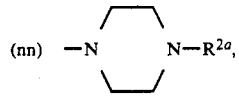

(oo) 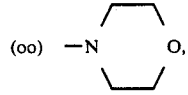

(pp) 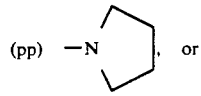, or (qq) 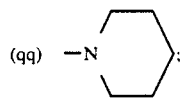;

—X$^1$—X$^2$—X$^3$—X$^4$— is:
(a) —Y—CR$^{11}$—CR$^{12}$—CZ—,
(b) —CR$^{11}$—Y—CR$^{12}$—CZ—,
(c) —CR$^{11}$—CR$^{12}$—Y—CZ—,
(d) —Y—CR$^{11}$—CZ—CR$^{12}$—,
(e) —CR$^{11}$—Y—CZ—CR$^{12}$—, or
(f) —CR$^{11}$—CR$^{12}$—CZ—Y—;

Y is: O, S, SO, or SO$_2$;

R$^9$ and R$^{10}$ are each independently:
(a) H,
(b) Cl, Br, I, F,
(c) NO$_2$,
(d) ($C_1$–$C_6$)-alkyl,
(e) ($C_1$–$C_6$)-acyloxy,
(f) ($C_3$–$C_6$)-cycloalkyl,
(g) ($C_1$–$C_6$)-alkoxy,
(h) —NHSO$_2$R$^{2a}$,
(i) hydroxy-($C_1$–$C_4$)-alkyl,
(j) ($C_1$–$C_4$)-alkyl-aryl,
(k) S(O)$_n$—($C_1$–$C_4$)-alkyl,
(n) NR$^{2a}$R$^{2a}$,
(q) CF$_3$,
(r) —SO$_2$NHR$^{2a}$,
(s) furyl,
(t) aryl, wherein aryl is phenyl or naphthyl, unsubstituted or substituted with one or two substituents selected from the group consisting of: Cl, Br, I, F, ($C_1$–$C_4$)-alkyl, ($C_1$–$C_4$)-alkoxy, NO$_2$, CF$_3$, ($C_1$–$C_4$)-alkylthio, OH, NH$_2$, —NH[($C_1$–$C_4$)-alkyl], —N[($C_1$–$C_4$)-alkyl]$_2$, —CO$_2$H, or —CO$_2$—($C_1$–$C_4$)-alkyl, or
(u) when R$^9$ and R$^{10}$ are bonded to adjacent carbon atoms, they can be joined to form an aryl ring;

R$^{11}$ and R$^{12}$ are independently:
(a) H,
(b) Cl, Br, I, F,
(c) NO$_2$,
(d) NH$_2$,
(e) NH[($C_1$–$C_4$)-alkyl],
(f) N[($C_1$–$C_4$)-alkyl]$_2$,
(g) SO$_2$NHR$^{2a}$,
(h) CF$_3$,
(i) ($C_1$–$C_7$)-alkyl,
(j) ($C_1$–$C_6$)-alkoxy, or
(k) ($C_3$–$C_7$)-cycloalkyl,
(l) when R$^{11}$ and R$^{12}$ are bonded to adjacent carbon atoms, they can be joined to form an aryl ring;
(m) O(CH$_2$)$_{n+1}$O(CH$_2$)$_s$CH$_3$,
(n) (CH$_2$)$_{n+1}$O(CH$_2$)$_s$CH$_3$,
(o) (CH$_2$)N(R$^{2a}$)$_2$,
(p) CH$_2$N[CH$_2$CH$_2$]$_2$O,
(q) (CH$_2$)$_n$N[CH$_2$CH$_2$]$_2$CH$_2$,
(r) CH(OR$^{2a}$)[($C_1$–$C_7$)-alkyl],
(s) CHO,
(t) CO$_2$R$^{2a}$,
(u) CH=CH—R$^{2a}$,
(v) CH$_2$CR$^{2a}$=C(R$^{2a}$)$_2$, or
(w) (CH$_2$)$_n$NCOR$^{2a}$;
(x) (CH$_2$)$_n$aryl, or
(y) CH(R$^{2a}$)$_2$;

Z is:
(a) —CO$_2$R$^{2a}$,
(b) —SO$_3$R$^{13}$,
(c) —NHSO$_2$CF$_3$,
(d) —PO(OR$^{13}$)$_2$,
(e) —SO$_2$NHR$^{2a}$,
(f) —CONHOR$^{13}$, (g) 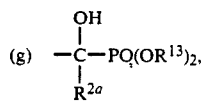

(h) —CN, (i) —SO$_2$NH-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: —OH, —SH, —(C$_1$–C$_4$)-alkyl, —(C$_1$–C$_4$)-alkoxy, —CF$_3$, Cl, Br, F, I, —NO$_2$, —CO$_2$H, —CO$_2$—(C$_1$–C$_4$)-alkyl, —NH$_2$, NH[(C$_1$–C$_4$)-akyl] and —N[(C$_1$–C$_4$)-alkyl]$_2$, (j) —CH$_2$SO$_2$NH-heteroaryl, (k) —SO$_2$NH—CO—R$^{14}$, (l) —CH$_2$SO$_2$NH—CO—R$^{14}$, (m) —CONH—SO$_2$R$^{14}$, (n) —CH$_2$CONH—SO$_2$R$^{14}$, (o) —NHSO$_2$NHCO—R$^{14}$, (p) —NHCONHSO$_2$—R$^{14}$, (q) 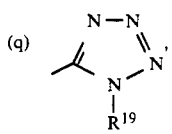

(r) 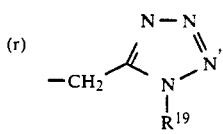

(s) 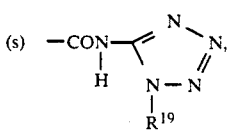

(t) —CONHNHSO$_2$CF$_3$, (u) 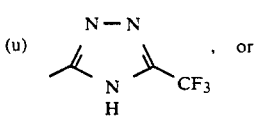, or (v) 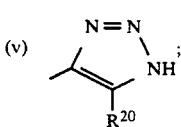;

R$^{13}$ is H, or 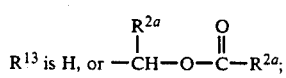

R$^{14}$ is (a) aryl,
(b) heteroaryl,
(c) (C$_3$–C$_7$)-cycloalkyl, or
(d) (C$_1$–C$_7$)-alkyl, unsubstituted or substituted with a substituent selected from the group consisting of: aryl, heteroaryl, —OH, —SH, (C$_1$–C$_4$)-alkyl, —(C$_1$–C$_4$)-alkoxy, —S(C$_1$–C$_4$)-alkyl, —CF$_3$, Cl, Br, F, I, —NO$_2$, —CO$_2$H, CO$_2$—(C$_1$–C$_4$)-alkyl, —NH$_2$, —N[(C$_1$–C$_4$)-alkyl]$_2$, —PO$_3$H or PO(OH)(O—(C$_1$–C$_4$)-alkyl);

(e) (C$_1$–C$_7$)-alkoxy,
(f) O(CH$_2$)$_{n+1}$O(CH$_2$)$_5$CH$_3$,
(g) (CH$_2$)$_{n+1}$O(CH$_2$)$_5$CH$_3$, or
(h) CH(R$^{2a}$)$_2$;
(i) (C$_1$–C$_6$)-polyfluoroalkyl, or
(j) —NH—(C$_1$–C$_6$)-alkyl;

R$^{15}$ is (a) H,
(b) aryl, which is unsubstituted or substituted with 1 or 2 substituents selected from the group consisting of: Cl, Br, I, F —O—(C$_1$–C$_4$)-alkyl, (C$_1$–C$_4$)-alkyl, —NO$_2$, —CF$_3$, —SO$_2$NR$^2$R$^{2a}$, —S—(C$_1$–C$_4$)-alkyl, —OH, —NH$_2$, (C$_3$–C$_7$)-cycloakyl, (C$_3$–C$_{10}$)-alkenyl;
(c) (C$_1$–C$_6$)-alkyl, (C$_2$–C$_6$)-alkenyl or (C$_2$–C$_6$)-alkynyl each of which is unsubstituted or substituted with one or more substituents selected from the group consisting of: aryl, (C$_3$–C$_7$)-cycloalkyl, Cl, Br, I, F, —OH, —NH$_2$, —NH[(C$_1$–C$_4$)-alkyl], —N[(C$_1$–C$_4$)-alkyl]$_2$, —NH—SO$_2$R$^{2a}$, —COOR$^{2a}$, —SO$_2$NHR$^{2a}$; or
(d) an unsubstituted, monosubstituted or disubstituted aromatic 5 or 6 membered ring which can contain one or two heteroatoms selected from the group consisting of N, O, S, and wherein the substituents are members selected from the group consisting of —OH, —SH, (C$_1$–C$_4$)-alkyl, (C$_1$–C$_4$)-alkoxy, —CF$_3$, Cl, Br, I, F, or NO$_2$;

R$^{16}$ is (a) (C$_1$–C$_{10}$)-alkyl,
(b) substituted (C$_1$–C$_{10}$)-alkyl in which one or two substituent(s) selected from the group consisting of:
  (1) I, Br, Cl, F,
  (2) hydroxy,
  (3) (C$_1$–C$_{10}$)-alkoxy,
  (4) (C$_1$–C$_5$)-alkoxycarbonyl,
  (5) (C$_1$–C$_5$)-acyloxy,
  (6) (C$_3$–C$_8$)-cycloalkyl,
  (7) aryl,
  (8) substituted aryl, in which the substituents are V and W,
  (9) (C$_1$–C$_{10}$)-alkyl-S(O)$_n$,
  (10) (C$_3$–C$_8$)-cycloalkyl-S(O)$_n$,
  (11) phenyl-S(O)$_n$,
  (12) substituted phenyl-S(O)$_n$, in which the substituents are V and W,
  (13) oxo,
  (14) carboxy,
  (15) NR$^{2a}$R$^{2a}$, or
  (16) (C$_1$–C$_5$)alkylaminocarbonyl;
(c) polyfluoro-(C$_1$–C$_4$)-alkyl,
(d) (C$_2$–C$_{10}$)-alkenyl,
(e) (C$_2$–C$_{10}$)-alkynyl,
(f) (C$_3$–C$_8$)-cycloalkyl,
(g) substituted (C$_3$–C$_8$)-cycloalkyl, in which the substituent is selected from:
  (1) (C$_1$–C$_5$)-alkyl, or
  (2) (C$_1$–C$_5$)-alkoxy;
(h) aryl,
(i) substituted aryl, in which the substituents are V and W,
(j) aryl-(CH$_2$)$_r$—(M$_1$)$_z$—(CH$_2$)$_r$—, (k) substituted aryl—$(CH_2)_r$—$(M_1)_z$—$(CH_2)_t$— in which the aryl group is substituted with V and W,

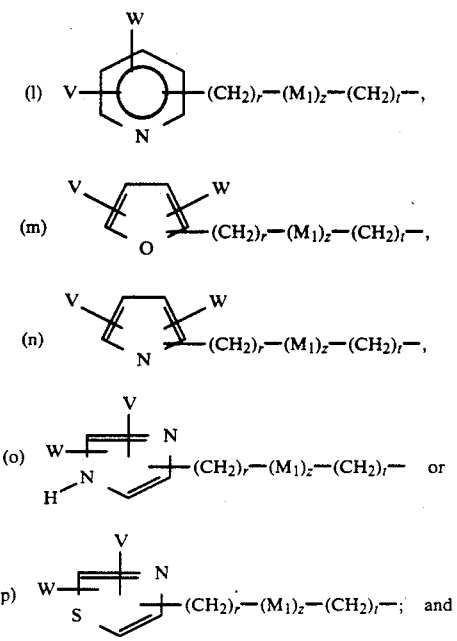

(q) —$[(C_1-C_4)\text{-alkyl}]NR^2R^{21}$,
(r) —$[(C_1-C_4)\text{-alkyl}]NR^2COR^{21}$,
(s) —$[(C_1-C_4)\text{-alkyl}]NR^2COOR^{21}$,
(t) —$[(C_1-C_4)\text{-alkyl}]CONR^{2a}R^{2a}$,
(u) —$[(C_1-C_4)\text{-alkyl}]N(R^2)SO_2R^{21}$,
(v) —$[(C_1-C_4)\text{-alkyl}]NR^2CONR^4R^{21}$, or
(w) —$[(C_1-C_4)\text{-alkyl}]OC(=O)NR^{21}R^{2a}$;

V and W are each independently selected from:
(a) H,
(b) $(C_1-C_5)$-alkoxy,
(c) $(C_1-C_5)$-alkyl,
(d) hydroxy,
(e) $(C_1-C_5)$-alkyl-$S(O)_n$,
(f) —CN,
(g) —$NO_2$,
(h) —$NR^2R^{2a}$,
(i) $(C_1-C_5)$-acyl-$NR^2R^{2a}$,
(j) —$CO_2R^{2a}$,
(k) $(C_1-C_5)$-alkyl-carbonyl,
(l) $CF_3$,
(m) I, Br, Cl, F,
(n) hydroxy-$(C_1-C_4)$-alkyl-,
(o) carboxy-$(C_1-C_4)$-alkyl-,
(p) -tetrazol-5-yl,
(q) —$NH—SO_2CF_3$, or
(r) aryl;

$M_1$ is M or —$C(O)$—;
z is 0 or 1;
r and t are 0 to 2;
$R^{17}$ and $R^{18}$ are each independently selected from:
(a) H,
(b) aryl-$(C_1-C_4)$-alkyl-,
(c) heteroaryl-$(C_1-C_4)$-alkyl-,
(d) $(C_1-C_4)$-alkyl unsubstituted or substituted with a substituent selected from the group consisting of —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^{2a}$, $CONHR^{2a}$, —O—$COR^{2a}$, $CF_3$;
(e) $(C_1-C_4)$-alkenyl,
(f) —CO-aryl,
(g) $(C_3-C_7)$-cycloalkyl,
(h) Cl, Br, I, F,
(i) —OH,
(j) —O—$(C_1-C_4)$-alkyl,
(k) —$(C_1-C_4)$-polyfluoroalkyl,
(l) —SH,
(m) —$S(O)_n$—$(C_1-C_4)$-alkyl,
(n) —CHO,
(o) —$CO_2R^{2a}$,
(p) —$SO_3H$,
(q) —$NH_2$,
(r) —$NH[(C_1-C_4)\text{-alkyl}]$,
(s) —$N[(C_1-C_4)\text{-alkyl}]_2$,
(t) —$NHCO_2$—$(C_1-C_4)$-alkyl,
(u) —$SO_2NR^2R^{2a}$,
(v) —$CH_2OCOR^{2a}$,
(w) —NH—$SO_2$—$(C_1-C_4)$-alkyl,
(x) 5 or 6 membered saturated heterocycle containing one nitrogen atom and optionally containing one other heteroatom selected from N, O, or S, such as pyrrolidine, morpholine, or piperazine,
(y) aryl,
(z) heteroaryl, wherein heteroaryl is a 5 or 6 membered aromatic ring containing one or two heteroatoms selected from the group consisting of O, N, or S,
(aa) tetrazol-5-yl,
(bb) —$[(C_1-C_4)\text{-alkyl}]NR^2R^{21}$,
(cc) —$[(C_1-C_4)\text{-alkyl}]NR^2COR^{21}$,
(dd) —$[(C_1-C_4)\text{-alkyl}]NR^2COOR^{21}$,
(ee) —$[(C_1-C_4)\text{-alkyl}]CONR^{2a}R^{2a}$,
(ff) —$[(C_1-C_4)\text{-alkyl}]N(R^2)SO_2R^{21}$,
(gg) —$[(C_1-C_4)\text{-alkyl}]NR^2CONR^4R^{21}$, or
(hh) —$[(C_1-C_4)\text{-alkyl}]OC(=O)NR^{21}R^{2a}$;

$R^{19}$ is:
(a) H,
(b) $(C_1-C_6)$-alkyl,
(c) $(C_2-C_4)$-alkenyl,
(d) $(C_1-C_4)$-alkoxy, or
(e) benzyl, wherein the phenyl is unsubstituted or substituted with a substituent selected from the group consisting of: —$NO_2$, —$NH_2$, —OH or —$OCH_3$;

$R^{20}$ is —CN, —$NO_2$, —$CO_2R^{2a}$, or —$CF_3$; and
$R^{21}$ is:
(a) aryl, unsubstituted or substituted with a substituent selected from Cl, Br, F or I, or
(b) $(C_1-C_4)$-alkyl is unsubstituted or substituted with:
i) $NH_2$,
ii) $NH[(C_1-C_4)\text{-alkyl}]$,
iii) $N[(C_1-C_4)\text{-alkyl}]_2$,
iv) $CO_2H$,
v) $CO_2(C_1-C_4)$-alkyl,
vi) OH,
vii) $SO_3H$, or
viii) $SO_2NH_2$,
(c) heteroaryl, or
(d) $(C_3-C_7)$ cycloalkyl;
or a pharmaceutically acceptable salt thereof.
Wherein an embodiment of the invention is when:
$R^1$ is:
(a) $(C_1-C_6)$-alkyl or $(C_2-C_6)$-alkenyl or $(C_2-C_6)$-alkynyl each of which is unsubstituted or substituted with a substituent selected from the group consisting of:
i) $(C_1-C_4)$-alkylthio,
ii) $(C_1-C_4)$-alkoxy,
iii) $CF_3$,
iv) $CF_2CF_3$, or
v) $(C_3-C_5)$-cycloalkyl,
(b) polyfluoro-$(C_1-C_4)$-alkyl, or
(c) $(C_3-C_5)$-cycloalkyl;

E is:
(a) single bond,
(b) —S—, or
(c) —O—;

$J^1$ is (a) —C(=M)—, (b) $J^1$ and L are connected together to form a 6-carbon aromatic ring substituted with $R^{7a}$, $R^{7b}$, $R^{8a}$ and $R^{8b}$ or (c) $J^1$ and L are connected together to form a 6-membered aromatic ring containing one nitrogen atom not at $J^1$, substituted with $R^{7a}$, $R^{8a}$ and $R^{8b}$;

$K^1$ is (a) —C(=M)—, or (b) $K^1$ and L are connected together to form a 6-carbon aromatic ring substituted with $R^{7a}$, $R^{7b}$, $R^{8a}$ and $R^{8b}$, or (c) $K^1$ and L are connected together to form a six-membered aromatic ring containing one nitrogen atom substituted with $R^{7a}$, $R^{8a}$ and $R^{8b}$ provided that one and only one of $J^1$ and $K^1$ is —C(=M)—;

one of $a^1$ or $b^1$ is a double bond in structure Ia provided that when $J^1$ is —C(=M)— then $b^1$ is a double bond and when $K^1$ is —C(=M)— then $a^1$ is a double bond;

L is the point of attachment of the 6-membered fused aromatic ring optionally containing one nitrogen atom;

$J^2$ is (a) —C(=M)—, or (b) —C($R^{17}$)—;
$K^2$ is (a) —C(=M)—, or (b) —C($R^{17}$)—, provided that one and only one of $J^2$ and $K^2$ is —C(=M)—;

one of $a^2$ or $b^2$ is a double bond in structure Ic provided that when $J^2$ is —C(=M)— then $b^2$ is a double bond and when $K^2$ is —(=M)— then $a^2$ is a double bond.

M is O, S or $NR^{15}$;

$R^2$ is:
(a) H,
(b) $(C_1-C_6)$-alkyl;

$R^{2a}$ is:
(a) $R^2$,
(b) $CH_2$aryl, or
(c) aryl;

$R^{2b}$ is:
(a) $R^{2a}$, or
(b) $C_3-C_7$ cycloalkyl;

$R^{2c}$ is:
(a) —$SO_2$—$(C_1-C_6)$-alkyl,
(b) —CO—$(C_1-C_6)$-alkyl,
(c) —$SO_2$—$(C_3-C_6)$-cycloalkyl,
(d) —CO—$(C_3-C_6)$-cycloalkyl,
(e) —$SO_2$—$(C_1-C_4)$-polyfluoroalkyl,
(f) —CO-aryl,
(g) —CO-polyfluoroaryl,
(h) —CO-(2- or 3-thienyl),
(i) —$SO_2$—(2- or 3-thienyl),
(j) —CO—(2-, 3- or 4-pyridyl),
(k) —CONH—$(C_1-C_6)$-alkyl,
(l) —CON[$(C_1-C_6)$alkyl]$_2$,
(m) —$CO_2$—$(C_1-C_6)$-alkyl, or
(n) —$CO_2$—$(C_3-C_6)$cycloalkyl;

$R^{7a}$ and $R^{7b}$ are independently (a) H,
(b) $(C_1-C_6)$-alkyl, $(C_2-C_6)$-alkenyl or $(C_2-C_6)$-alkynyl,
(c) Cl, Br, I, F,
(d) $CF_3$, or
(e) when $R^{7a}$ and $R^{7b}$ are bonded to adjacent carbon atoms, they can be joined to form a phenyl ring;

$R^{8a}$ and $R^{8b}$ are independently
(a) H,
(b) aryl-$(C_1-C_4)$-alkyl,
(c) heteroaryl-$(C_1-C_4)$-alkyl,
(d) $(C_1-C_6)$-alkyl, is unsubstituted or substituted with a substituent selected from the group consisting of: —CON($R^{2a}$)$_2$, -heteroaryl, —S(O)$_x$—$R^{21}$, -tetrazol-5-yl, —$CONHSO_2R^{21}$, —$SO_2NH$-heteroaryl, —$SO_2NHCOR^{21}$, —$PO(OR^2)_2$, —$PO(OR^{2a})_2$, —$SO_2NH$—CN, —$NR^{2a}COOR^{21}$, —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^{2a}$, —$CONHR^{2a}$, —O—$COR^{2a}$, aryl, or

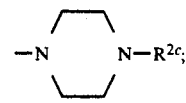

(e) —CO-aryl,
(f) $C_3-C_7$-cycloalkyl,
(g) Cl, Br, I, F,
(h) —OH,
(i) —$OR^{21}$,
(j) —SH,
(k) —S(O)$_n$—$(C_1-C_4)$-alkyl,
(l) —$COR^{2a}$,
(m) —$CO_2H$,
(n) —$SO_3H$,
(o) —$NR^{2a}R^{21}$,
(p) —$NR^{2a}COR^{21}$,
(q) —$NR^{21}COOR^{21}$,
(r) —$SO_2NR^{2a}$,
(s) —$SO_2NR^2R^{2a}$,
(t) —$NO_2$,
(u) —$NHSO_2CF_3$,
(v) —$CONR^{2a}R^{21}$,
(w) —$(C_1-C_4)$-polyfluoroalkyl,
(x) —$COOR^2$,
(y) —$SO_3H$,
(z) —$N(R^{2a})SO_2R^{21}$,
(aa) —$NR^{2a}CONR^{2b}R^{21}$,
(bb) —OC(=)$NR^{21}R^{2a}$,
(cc) -aryl,
(dd) —$NHSO_2CF_3$,
(ee) —$SO_2NH$-heteroaryl,
(ff) —$SO_2NHCOR^{21}$,
(gg) —$CONHSO_2R^{21}$,
(hh) —$PO(OR^2)_2$,
(ii) —tetrazol-5-yl,
(jj) —CONH(tetrazol-5-yl),
(kk) —$SO_2NHCN$,
(ll) —heteroaryl, (mm) 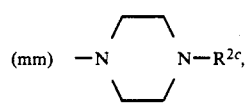

-continued (nn) 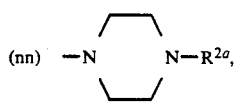

(oo) 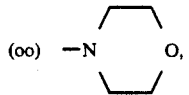

(pp) 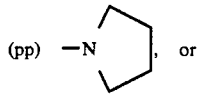, or (qq) 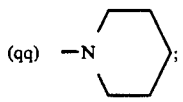;

—$X^1$—$X^2$—$X^3$—$X^4$— is:
- (a) —Y—$CR^{11}$=$CR^{12}$—CZ—,
- (b) —$CR^{11}$=Y—$CR^{12}$—CZ—,
- (c) —$CR^{11}$=$CR^{12}$—Y—CZ—,
- (d) —Y—$CR^{11}$=CZ—$CR^{12}$—,
- (e) —$CR^{11}$=Y—CZ—$CR^{12}$—, or
- (f) —$CR^{11}$=$CR^{12}$—CZ—Y—;

Y is: O, S, SO, or $SO_2$;

$R^9$ and $R^{10}$ are each independently:
- (a) H,
- (b) Cl, Br, I, F,
- (c) $NO_2$,
- (d) $(C_1-C_6)$-alkyl,
- (e) $(C_1-C_6)$-acyloxy,
- (f) $(C_3-C_6)$-cycloalkyl,
- (g) $(C_1-C_6)$-alkoxy,
- (h) —$NHSO_2R^{2a}$,
- (i) hydroxy-$(C_1-C_4)$alkyl,
- (j) $(C_1-C_4)$-alkyl-aryl,
- (k) $S(O)_n$-$(C_1-C_4)$-alkyl,
- (n) $NR^{2a}R^{2a}$,
- (q) $CF_3$,
- (r) —$SO_2NHR^{2a}$,
- (s) furyl,
- (t) aryl, wherein aryl is phenyl or naphthyl, unsubstituted or substituted with one or two substituents selected from the group consisting of: Cl, Br, I, F, $(C_1-C_4)$-alkyl, $(C_1-C_4)$-alkoxy, $NO_2$, $CF_3$, $(C_1-C_4)$-alkylthio, OH, $NH_2$, —NH[($C_1-C_4$)-alkyl], —N[($C_1-C_4$)-alkyl]$_2$, —$CO_2H$, or —$CO_2$-$(C_1-C_4$-alkyl), or
- (u) when $R^9$ and $R^{10}$ are bonded to adjacent carbon atoms, they can be joined to form an aryl ring;

$R^{11}$ and $R^{12}$ are independently:
- (a) H,
- (b) Cl, Br, I, F,
- (c) $NO_2$,
- (d) $NH_2$,
- (e) NH[($C_1-C_4$)-alkyl],
- (f) N[($C_1-C_4$)-alkyl]$_2$,
- (g) $SO_2NHR^{2a}$,
- (h) $CF_3$,
- (i) (C-$C_7$)-alkyl,
- (j) $(C_1-C_6)$-alkoxy, or
- (k) $(C_3-C_7)$-cycloalkyl,
- (l) when $R^{11}$ and $R^{12}$ are bonded to adjacent carbon atoms, they can be joined to form an aryl ring;

- (m) $O(CH_2)_{n+1}O(CH_2)_sCH_3$,
- (n) $(CH_2)_{n+1}O(CH_2)_sCH_3$,
- (o) $(CH_2)N(R^{2a})_2$,
- (p) $(CH_2)_nN[CH_2CH_2]_2X$,
- (q) $(CH_2)_nN[CH_2CH_2]_2CH_2$,
- (r) $CH(OR^{2a})[(C_1-C_7)$-alkyl],
- (s) CHO,
- (t) $CO_2R^{2a}$,
- (u) CH=CH—$R^{2a}$,
- (v) $CH_2CR^{2a}$=$C(R^{2a})_2$,
- (w) $(CH_2)_nNCOR^{2a}$,
- (x) $(CH_2)_n$aryl, or
- (y) $CH(R^{2a})_2$;

Z is:
- (a) —$CO_2R^{2a}$;
- (b) —$NHSO_2CF_3$,
- (c) —$SO_2NHR^{2a}$,
- (d) —CN,
- (e) —$SO_2NH$-heteroaryl, wherein heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, —$(C_1-C_4)$-alkyl, —$(C_1-C_4)$-alkoxy, —$CF_3$, Cl, Br, F, I, —$NO_2$, —$CO_2H$, —$CO_2$-$C_1-C_4$-alkyl, —$NH_2$, NH[($C_1-C_4$)-alkyl] and —N[($C_1-C_4$-alkyl]$_2$,
- (f) —1H-tetrazol-5-yl,
- (g) —$CH_2$-1H-tetrazol-5-yl,
- (h) —CONH-1H-tetrazol-5-yl, or
- (i) —$SO_2HNCOR^{14}$;

$R^{14}$ is
- (a) aryl,
- (b) heteroaryl,
- (c) $(C_3-C_7)$-cycloalkyl, or
- (d) $(C_1-C_7)$-alkyl, unsubstituted or substituted with a substituent selected from the group consisting of: aryl, heteroaryl, —OH, —SH, $(C_1-C_4)$alkyl, —$(C_1-C_4)$-alkoxy, —$S(C_1-C_4)$-alkyl, —$CF_3$, Cl, Br, F, I, —$NO_2$, —$CO_2H$, $CO_2$—$(C_1-C_4)$-alkyl, —$NH_2$, —N[($C_1-C_4$)-alkyl]$_2$, —$PO_3H$ or PO(OH)(O—$(C_1-C_4)$-alkyl);
- (e) $(C_1-C_7)$-alkoxy,
- (f) $O(CH_2)_{n+1}O(CH_2)_sCH_3$,
- (g) $(CH_2)_{n+1}O(CH_2)_sCH_3$,
- (h) $CH(R^{2a})_2$,
- (i) —NH—$(C_1-C_6)$-alkyl, $R^{15}$ is:
- (a) H,
- (b) aryl, is unsubstituted or substituted with 1 or 2 substituents selected from the group consisting of Cl, Br, I, F, —O—$(C_1-C_4)$-alkyl, $(C_1-C_4)$-alkyl, —$NO_2$, —$CF_3$, —$SO_2NR^2R^{2a}$, —S—$(C_1-C_4)$-alkyl, —OH, —$NH_2$, $(C_3-C_7)$-cycloalkyl, $(C_3-C_{10})$-alkenyl;
- (c) $(C_1-C_6)$-alkyl, $(C_2-C_6)$-alkenyl or $(C_2-C_6)$-alkynyl each of which is unsubstituted or substituted with one or more substituents selected from the group consisting of: aryl, $(C_3-C_7)$-cycloalkyl, Cl, Br, I, F, —OH, —$NH_2$, —NH[($C_1-C_4$)-alkyl], —N[($C_1-C_4$)-alkyl]$_2$, —NH—$SO_2R^{2a}$, —$COOR^{2a}$, —$SO_2NHR^{2a}$; or
- (d) an unsubstituted, monosubstituted or disubstituted aromatic 5 or 6 membered ring which contains one or two heteroatoms selected from the group consisting of N, O, S, and wherein the substituents are members selected from the group consisting of —OH, —SH, $(C_1-C_4)$-alkyl, $(C_1-C_4)$-alkyloxy —$CF_3$, Cl, Br, I, F, or $NO_2$;

$R^{16}$ is:
- (a) $(C_1-C_{10})$-alkyl,
- (b) substituted $(C_1-C_{10})$-alkyl in which one or two substituent(s) is (are) selected from:
  - (1) hydroxy,
  - (2) $(C_1-C_5)$-alkoxy,
  - (3) $(C_1-C_5)$-alkoxycarbonyl,
  - (4) phenyl,
  - (5) carboxy, or
  - (6) C(=O)NH-$(C_1-C_5)$-alkyl;
- (c) aryl, or
- (d) aryl substituted with V and W;

V and W are selected from:
- (a) H,
- (b) $(C_1-C_5)$-alkoxy,
- (c) $(C_1-C_5)$-alkyl,
- (d) hydroxy,
- (e) —CN,
- (f) —$NO_2$,
- (g) —$NR^2R^{2a}$,
- (h) —$CO^2R^{2a}$,
- (i) —$CF_3$,
- (j) I, Br, Cl, F,
- (k) hydroxy-$(C_1-C_4)$-alkyl—,
- (l) tetrazol-5-yl,
- (m) —NH—$SO_2CF_3$,
- (n) —[$(C_1-C_4)$-alkyl]$NR^2R^{21}$,
- (o) —[$(C_1-C_4)$-alkyl]$NR^2COR^{21}$,
- (p) —[$(C_1-C_4)$-alkyl]$NR^2COOR^{21}$,
- (q) —[$(C_1-C_4)$-alkyl]$CONR^{2a}R^{2a}$,
- (r) —[$(C_1-C_4)$-alkyl]$N(R^2)SO_2R^{21}$,
- (s) —[$(C_1-C_4)$-alkyl]$NR^2CONR^4R^{21}$, or
- (t) —[$(C_1-C_4)$-alkyl]OC(=O)$NR^{21}R^{2a}$;

$R^{17}$ and $R^{18}$ are independently
- (a) H,
- (b) aryl-$(C_1-C_4)$-alkyl—,
- (c) heteroaryl-$(C_1-C_4)$-alkyl—,
- (d) $(C_1-C_4)$-alkyl, unsubstituted or substituted with a substituent selected from the group consisting of: —OH, —$NH_2$, guanidino, $(C_1-C_4)$alkoxy, $(C_1-C_4)$-alkylthio, $(C_1-C_4)$-alkylamino, $(C_1-C_4)$-dialkylamino, —$COOR^{2a}$, —$CONHR^{2a}$, —O—$COR^{2a}$, $CF_3$,
- (e) $(C_1-C_4)$-alkenyl,
- (f) —CO—aryl,
- (g) $(C_3-C_7)$-cycloalkyl,
- (h) Cl, Br, I, F,
- (i) —OH,
- (j) —O—$(C_1-C_4)$-alkyl,
- (k) —$(C_1-C_4)$-polyfluoroalkyl,
- (l) —SH,
- (m) —$S(O)_n$—$(C_1-C_4)$-alkyl,
- (n) —CHO,
- (o) —$CO_2R^{2a}$,
- (p) —$SO_3H$,
- (q) —$NH_2$,
- (r) —NH[$(C_1-C_4)$-alkyl],
- (s) —N[$(C_1-C_4)$-alkyl]$_2$,
- (t) —$NHCO_2$—$(C_1-C_4)$-alkyl,
- (u) —$SO_2NR^2R^{2a}$,
- (v) —$CH_2OCOR^{2a}$,
- (w) —NH—$SO_2$—$(C_1-C_4)$-alkyl,
- (x) 5 or 6 membered saturated heterocycle containing one nitrogen atom and optionally containing one other heteroatom selected from N, O, or S, such as pyrrolidine, morpholine, or piperazine,
- (y) aryl,
- (z) heteroaryl, wherein heteroaryl is a 5 or 6 membered aromatic ring containing one or two heteroatoms selected from the group consisting of O, N, or S;
- (aa) tetrazol-5-yl, or
- (bb) —[$(C_1-C_4)$-alkyl]$NR^2R^{21}$,
- (cc) —[$(C_1-C_4)$-alkyl]$NR^2COR^{21}$,
- (dd) —[$(C_1-C_4)$-alkyl]$NR^2COOR^{21}$,
- (ee) —[$(C_1-C_4)$-alkyl]$CONR^{2a}R^{2a}$,
- (ff) —[$(C_1-C_4)$-alkyl]$N(R^2)SO_2R^{21}$,
- (gg) —[$(C_1-C_4)$-alkyl]$NR^2CONR^4R^{21}$, or
- (hh) —[$(C_1-C_4)$-alkyl]OC(=O)$NR^{21}R^{2a}$;

$R^{21}$ is:
- (a) aryl, unsubstituted or substituted with a substituent selected from Cl, Br, F or I, or
- (b) $(C_1-C_4)$-alkyl which is unsubstituted or substituted with:
  - i) $NH_2$,
  - ii) NH[$(C_1-C_4)$-alkyl],
  - iii) N[$(C_1-C_4)$-alkyl]$_2$,
  - iv) $CO_2H$,
  - v) $CO_2(C_1-C_4)$-alkyl,
  - vi) OH,
  - vii) $SO_3H$, or
  - viii) $SO_2NH_2$;
- (c) heteroaryl, or
- (d) $C_3-C_7$ cycloalkyl;

or a pharmaceutically acceptable salt thereof.

Wherein another embodiment of the invention is when:

$R^1$ is:
- (a) $(C_1-C_6)$-alkyl $(C_2-C_6)$-alkenyl or $(C_2-C_6)$-alkynyl each of which is unsubstituted or substituted with a substituent selected from the group consisting of:
  - i) $(C_1-C_4)$-alkylthio,
  - ii) $(C_1-C_4)$-alkoxy,
  - iii) $CF_3$,
  - iv) $CF_2CF_3$, or
  - v) $(C_3-C_5)$-cycloalkyl, or
- (b) $(C_1-C_4)$-polyfluoroalkyl;

E is a single bond;

$J^1$ and L are connected together to form a 6-carbon aromatic ring substituted with $R^{7a}$, $R^{7b}$, $R^{8a}$ and $R^{8b}$; or $J^1$ and L are connected together to form a 6-membered aromatic ring containing one nitrogen atom not at $J^1$, substituted with $R^{7a}$, $R^{8a}$ and $R^{8b}$;

$K^1$ is —C(=M)—;

$a^1$ is a double bond;

L is the point of attachment of the 6-membered fused aromatic ring optionally containing one nitrogen atom;

$J^2$ is —C($R^{17}$)—;

$K^2$ is —C(=M)—;

$a^2$ is a double bond;

M is O, or $NR^{15}$;

$R^2$ is:
- (a) H,
- (b) $(C_1-C_6)$-alkyl, or
- (c) $(C_1-C_6)$-alkyl;

$R^{2a}$ is:
- (a) $R^2$,
- (b) benzyl, or
- (c) phenyl;

$R^{2b}$ is:
- (a) $R^{2a}$, or
- (b) $C_3$-$C_7$ cycloalkyl;

$R^{2c}$ is:
- (a) $-SO_2-(C_1-C_6)$-alkyl,
- (b) $-CO-(C_1-C_6)$-alkyl,
- (c) $-SO_2-(C_3-C_6)$-cycloalkyl,
- (d) $-CO-(C_3-C_6)$-cycloalkyl,
- (e) $-SO_2-(C_1-C_4)$-polyfluoroalkyl,
- (f) $-CO$-aryl,
- (g) $-CO$-polyfluoroaryl,
- (h) $-CO-$(2- or 3-thienyl),
- (i) $-SO_2-$(2- or 3-thienyl),
- (j) $-CO-$(2-, or 3- or 4-pyridyl),
- (k) $-CONH-(C_1-C_6)$-alkyl,
- (l) $-CON[(C_1-C_6)alkyl]_2$,
- (m) $-CO_2-(C_1-C_6)$-alkyl, or
- (n) $-CO_2-(C_3-C_6)$cycloalkyl; or $R^{7a}$ and $R^{7b}$ are independently:
- (a) H,
- (b) $(C_1-C_6)$-alkyl, $(C_2-C_6)$-alkenyl or $(C_2-C_6)$-alkynyl,
- (c) Cl, Br, I, F,
- (d) $CF_3$, or
- (e) when $R^{7a}$ and $R^{7b}$ are bonded to adjacent carbon atoms, they can be joined to form a phenyl ring;

$R^{8a}$ and $R^{8b}$ are independently:
- (a) H,
- (b) aryl-$(C_1-C_4)$-alkyl,
- (c) heteroaryl-$(C_1-C_4)$-alkyl,
- (d) $(C_1-C_6)$-alkyl, unsubstituted or substituted with a substituent selected from the group consisting of: $-CON(R^{2a})_2$, $-$heteroaryl, $-S(O)_n-R^{21}$, $-$tetrazol-5-yl, $-CONHSO_2R^{21}$, $-SO_2NH$-heteroaryl, $-SO_2NHCOR^{21}$, $-PO(OR^2)_2$, $-PO(OR^{2a})_2$, $-SO_2NH-CN$, $-NR^{2a}COOR^{21}$, $-OH$, $-NH_2$, guanidino, $(C_1-C_4)$-alkoxy, $(C_1-C_4)$-alkylthio, $(C_1-C_4)$-alkylamino, $(C_1-C_4)$-dialkylamino, $-COOR^{2a}$, $-CONHR^{2a}$, $-O-COR^{2a}$ aryl,

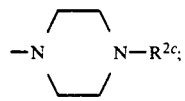

- (e) $-CO$-aryl,
- (f) $(C_3-C_7)$-cycloalkyl,
- (g) Cl, Br, I, F,
- (h) $-OH$,
- (i) $-OR^{21}$,
- (j) $-SH$,
- (k) $-S(O)_n-(C_1-C_4)$-alkyl,
- (l) $-COR^{2a}$,
- (m) $-CO_2H$,
- (n) $-SO_3H$,
- (o) $-NR^{2a}R^{21}$,
- (p) $-NR^{2a}COR^{21}$,
- (q) $-NR^{2a}COOR^{21}$,
- (r) $-SO_2NR^{2a}$,
- (s) $-SO_2NR^2R^{2a}$,
- (t) $-NO_2$,
- (u) $-NHSO_2CF_3$,
- (v) $-CONR^{2a}R^{21}$,
- (w) $-(C_1-C_4)$-polyfluoroalkyl,
- (x) $-COOR^2$,
- (y) $-SO_3H$,
- (z) $-N(R^{2a})SO_2R^{21}$,
- (aa) $-NR^{2a}CONR^{2b}R^{21}$,
- (bb) $-OC(=O)NR^{21}R^{2a}$,
- (cc) $-$aryl,
- (dd) $-NHSO_2CF_3$,
- (ee) $-SO_2NH$-heteroaryl,
- (ff) $-SO_2NHCOR^{21}$,
- (gg) $-CONHSO_2R^{21}$,
- (hh) $-PO(OR^2)_2$,
- (ii) $-$tetrazol-5-yl,
- (jj) $-CONH$(tetrazol-5-yl),
- (kk) $-SO_2NHCN$,
- (ll) $-$heteroaryl,

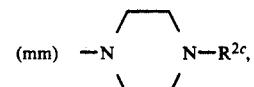

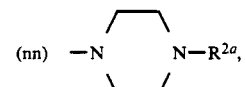

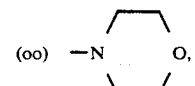

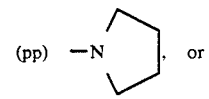

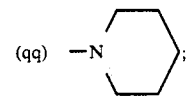

$-X^1-X^2-X^3-X^4-$ is:
- (a) $-Y-CR^{11}-CR^{11}-CR^{12}-CZ-$,
- (b) $-CR^{11}-Y'CR^{12}-CZ-$,
- (c) $-CR^{11}-CR^{12}-Y-CZ-$,
- (d) $-Y-CR^{11}-CZ-CR^{12}-$,
- (e) $-CR^{11}-Y-CZ-CR^{12}-$, or
- (f) $-CR^{11}-CR^{12}-CZ-Y-$;

Y is: O or S;

$R^9$ and $R^{10}$ are each independently:
- (a) H,
- (b) Cl, Br, I, F,
- (c) $NO_2$,
- (d) $(C_1-C_6)$-alkyl,
- (e) $(C_1-C_6)$-alkoxy,
- (f) $(C_3-C_6)$-cycloalkyl,
- (g) $(C_1-C_6)$-alkoxy,
- (h) $-NHSO_2R^{2a}$,
- (i) hydroxy-$(C_1-C_4)$-alkyl,
- (j) $(C_1-C_4)$-alkyl-aryl,
- (k) $S(O)_n-(C_1-C_4)$-alkyl,
- (n) $NR^{2a}R^{2a}$,
- (q) $CF_3$,
- (r) $-SO_2NHR^{2a}$,
- (s) furyl,
- (t) aryl, wherein aryl is phenyl or naphthyl, unsubstituted or substituted with one or two substituents selected from the group consisting of: Cl, Br, I, F, $(C_1-C_4)$-alkyl, $(C_1-C_4)$-alkoxy, $NO_2$, CF₃, (C₁-C₄)-alkylthio, OH, NH₂, —NH[(-C₁-C₄)-alkyl], —N[(C₁-C₄)-alkyl]₂, —CO₂H, or —CO₂-(C₁-C₄)-alkyl, or (u) when $R^9$ and $R^{10}$ re bonded to adjacent carbon atoms, they can be joined to form an aryl ring;

$R^{11}$ and $R^{12}$ are independently:
- (a) H,
- (b) Cl, Br, I, R,
- (c) NH₂,
- (d) NH[(C₁-C₄)-alkyl],
- (e) N[(C₁-C₄)-alkyl]₂,
- (f) SO₂NHR$^{2a}$,
- (g) CF₃,
- (h) (C₁-C₇)-alkyl,
- (i) (C₁-C₄)-alkoxy, or
- (j) (C₃-C₇)-cycloalkyl;

Z is:
- (a) —CO₂R$^{2a}$,
- (b) —NHSO₂CF₃,
- (c) —SO₂NHR$^{14}$,
- (d) —1H-tetrazol-5-yl,
- (e) —SO₂NHCOR$^{14}$, or
- (f) —NHSO₂R$^{14}$;

$R^{14}$ is
- (a) aryl,
- (b) heteroaryl,
- (c) (C₃-C₇)-cycloalkyl, or
- (d) (C₁-C₄)alkyl, unsubstituted or substituted with a substituent selected from the group consisting of aryl as defined above, heteroaryl as defined above, —OH, —SH, (C₁-C₄)-alkyl, —(C₁-C₄)-alkoxy, —S(C₁-C₄)-alkyl, —CF₃, Cl, Br, F, I, —NO₂, —CO₂H, CO₂—(C₁-C₄)-alkyl, —NH₂, —N[(C₁-C₄)-alkyl]₂, —PO₃H, PO(OH)(O—(C₁-C₄)-alkyl;
- (e) (C₁-C₇)-alkoxy,
- (f) O(CH₂)$_{n+1}$O(CH₂)$_s$CH₃,
- (g) (CH₂)$_{n+1}$O(CH₂)$_s$CH₃,
- (h) CH(R$^{2a}$)₂,
- (i) (C₁-C₆)-polyfluoroalkyl, or
- (j) 'NH(C₁-C₆)-alkyl;

$R^{15}$ is:
- (a) H,
- (b) aryl, unsubstituted or substituted with 1 or 2 substituents selected from the group consisting of: Cl, Br, I, F —O—(C₁-C₄)-alkyl, (C₁-C₄)-alkyl, —NO₂, —CF₃, —SO₂NR²R$^{2a}$, —S—(C₁-C₄)-alkyl, —OH, —NH₂, (C₃-C₇)-cycloalkyl, (C₃-C₁₀)-alkenyl;
- (c) (C₁-C₆)-alkyl, (C₂-C₆)-alkenyl or (C₂-C₆)-alkynyl each of which is unsubstituted or substituted with one or more substituents selected from the group consisting of aryl as defined above, (C₃-C₇)-cycloalkyl, Cl, Br, I, F, —OH, —NH₂, —NH[(C₁-C₄)-alkyl], —N[(C₁-C₄)-alkyl]₂, —NH—SO₂R$^{2a}$, —COOR$^{2a}$, —SO₂NHR$^{2a}$; or
- (d) an unsubstituted, monosubstituted or disubstituted aromatic 5 or 6 membered ring which can contain one or two heteroatoms selected from the group consisting of N, O, S, and wherein the substituents are members selected from the group consisting of: —OH, —SH, (C₁-C₄)-alkyl, (C₁-C₄)-alkyloxy —CF₃, Cl, Br, I, F, or NO₂;

$R^{16}$ is
- (a) (C₁-C₁₀)-alkyl,
- (b) substituted (C₁-C₁₀)-alkyl in which one or more substituent(s) is selected form
  - (1) hydroxy,
  - (2) (C₁-C₅)-alkoxy,
  - (3) (C₁-C₅)-alkoxycarbonyl,
  - (4) phenyl,
  - (5) carboxy, or
  - (6) C(50 O)NH—(C₁-C₅)-alkyl,
- (c) aryl, or
- (d) aryl substituted with V and W;

V and W are selected from:
- (a) H,
- (b) (C₁-C₅)-alkoxy,
- (c) (C₁-C₅)alkyl,
- (d) hydroxy,
- (e) —CN,
- (f) —NO₂,
- (g) —NR²R$^{2a}$,
- (h) —CO₂R$^{2a}$,
- (i) —CF₃,
- (j) I, Br, Cl, F,
- (k) hydroxy-C₁-C₄)-alkyl—,
- (l) —1H-tetrazol-5-yl, or
- (m) —NH—SO₂CF₃;

$R^{17}$ and $R^{18}$ are independently
- (a) H,
- (b) aryl-(C₁-C₄)-alkyl—,
- (c) heteroaryl-(C₁-C₄)-alkyl—,
- (d) (C₁-C₄)-alkyl, unsubstituted or substituted with a substituent selected from the group consisting of: —OH, —NH₂, guanidino, (C₁-C₄)-alkoxy, (C₁-C₄)-alkylthio, (C₁-C₄)-alkylamino, (C₁-C₄)-dialkylamino, —COOR$^{2a}$, —CONHR$^{2a}$, —O—COR$^{2a}$, CF₃;
- (e) (C₁-C₄)-alkenyl,
- (f) —CO-aryl,
- (g) (C₃-C₇)-cycloalkyl,
- (h) Cl, Br, I, F,
- (i) —OH,
- (j) —O—(C₁-C₄)-alkyl,
- (k) —(C₁-C₄)-polyfluoroalkyl,
- (l) —SH,
- (m) —S(O)$_n$—(C₁-C₄)-alkyl,
- (n) —CHO,
- (o) —CO₂R$^{2a}$,
- (p) —SO₃H,
- (q) —NH₂,
- (r) —NH[(C₁-C₄)-alkyl],
- (s) —N[(C₁-C₄)-alkyl]₂,
- (t) —NHCO₂—(C₁-C₄)-alkyl,
- (u) —SO₂NR²R$^{2a}$,
- (v) —CH₂OCOR$^{2a}$,
- (w) —NH—SO₂—(C₁-C₄)-alkyl,
- (x) 5 or 6 membered saturated heterocycle containing one nitrogen atom and optionally containing one other heteroatom selected from N, O, or S, such as pyrrolidine, morpholine, or piperazine,
- (y) aryl,
- (z) heteroaryl, or
- (aa) tetrazol-5-yl; and $R^{21}$ is:
- (a) aryl, unsubstituted or substituted with a substituent selected from Cl, Br, F or I, or
- (b) (C₁-C₄)-alkyl which is unsubstituted or substituted with:
  - i) NH₂,
  - ii) NH[(C₁-C₄)-alkyl],
  - iii) N[(C₁-C₄)-alkyl]₂,
  - iv) CO₂H,
  - v) CO₂(C₁-C₄)-alkyl,
  - vi) OH, vii) SO₃H, or
viii) SO₂NH₂;
(c) heteroaryl, or
(d) (C₃-C₇)-cycloalkyl;
or a pharmaceutically acceptable salts thereof.

A class within the embodiment is when the structural formula is:

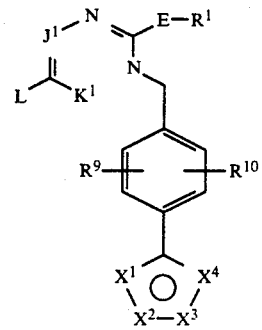

A subclass within the embodiment is when the structural formula is:

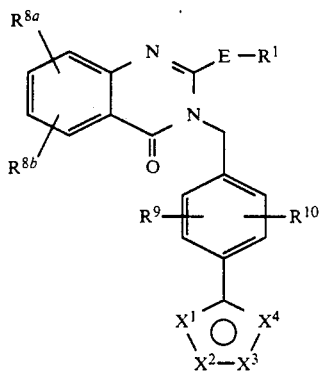

or a pharmaceutically acceptable salt thereof, wherein the substituents are as defined above.

A subclass within this class is when the structural formula is:

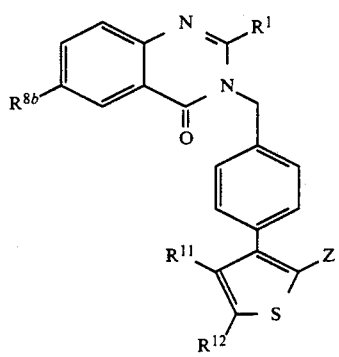

wherein
R¹ is: ethyl, n-propyl, n-butyl or pentyl;
R²ᶜ is: H, COCH₃, CO₂Me CO₂Et, CONHCH₃, CON[CH₃]₂, COphenyl, CO-4-pyridinyl, CO₂-n-butyl, CO-cyclopropyl, SO₂-isopropyl, CONH-n-propyl, or

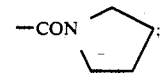

R⁸ᵇ is:
N(n-butyl)CO-phenyl,
N(pentyl)CO-phenyl,
N(benzyl))CO-phenyl,
N(benzyl)CO₂ isobutyl,
N(pentyl)CO-4-pyridyl,
N(pentyl)CO-(4-chlorophenyl),
N(n-butyl)CO-(4-fluorophenyl),
N(methyl)CO₂-isobutyl,
isopropyl,
N(benzyl)CON(methyl)(ethyl), or

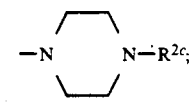

R¹¹ is: H or R¹¹ and R¹² can joined to form an phenyl ring;
R¹² is: H, (C₁-C₆)-alkyl, (C₁-C₆)-alkoxy, —CH₂-aryl, O(CH₂)ₙ₊₁O(CH₂)ₛCH₃, (CH₂)ₙ₊₁O(CH₂)ₛ(CH₃, or CH₂N[CH₂CH₂]₂O;
Y is: O, or S; and
Z is:
(a) CO₂R²,
(b) 1H-tetrazol-5-yl,
(c) CONHSO₂R¹⁴,
(d) SO₂NHR¹⁴,
(e) NHSO₂R¹⁴,
(f) SO₂HNHCOR¹⁴, or
(g) NHSO₂CF₃.

Another subclass of within this class is when the structural formula is:

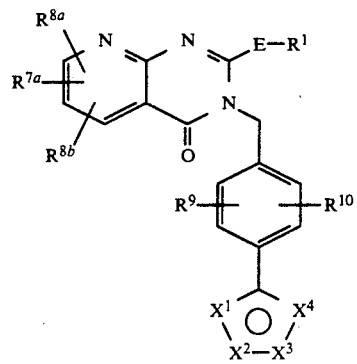

or a pharmaceutically acceptable salt thereof.

Another subclass of within this class is when the structural formula is:

or a pharmaceutically acceptable salt thereof.

Another class within this embodiment is when the structural formula is:

or a pharmaceutically acceptable salt thereof.

Another class within this embodiment is represented by structural formula:

wherein:
$R^1$ is: ethyl, n-propyl, n-butyl;
$R^{16}$ is:
  benzyl,
  2-carboxyphenyl,
  2-chlorophenyl,
  2-trifluoromethylphenyl,
  2-methylphenyl, or
  2,6 dichloromethyl;
—$X^1$—$X^2$—$X^3$—$X^4$— is:
  (a) —Y—$CR^{11}$—$CR^{12}$—CZ—,
  (b) —$CR^{11}$—Y—$CR^{12}$—CZ—, or
  (c) $CR^{11}$—$CR^{12}$—Y—CZ—;

$R^{11}$ is: H or $R^{11}$ and $R^{12}$ can joined to form an phenyl ring;
$R^{12}$ is: H, ($C_1$-$C_6$)-alkyl, ($C_1$-$C_6$)-alkoxy, —$CH_2$-aryl, $O(CH_2)_{n+1}O(CH_2)_5CH_3$, $(CH_2)_{n+1}O(CH_2)_5CH_3$, or $CH_2N[CH_2CH_2]_2O$;
Y is: O, or S; and
Z is:
  (a) $CO_2R^2$,
  (b) 1H-tetrazol-5-yl,
  (c) $CONHSO_2R^{14}$,
  (d) $SO_2NHR^{14}$,
  (e) $NHSO_2R^{14}$,
  (f) $SO_2NHCOR^{14}$, or
  (g) $NHSO_2CF_3$.

Another class within this embodiment is when the structural formula is:

or a pharmaceutically acceptable salt thereof.

Another class within the embodiment of the invention is the structural formula is wherein:
$R^1$ is: ethyl, n-propyl, n-butyl,
$R^{17}$ and $R^{18}$ are independently:
  hydrogen,
  methyl,
  carboxyl,
  benzyl,
  2-chlorophenyl,
  2-trifluoromethylphenyl, or
  2-tolyl;
—$X^1$—$X^2$—$X^3$—$X^4$— is:
  (a) —Y—$CR^{11}$—$CR^{12}$—CZ—,
  (b) —$CR^{11}$—Y—$CR^{12}$—CZ—, or
  (c) $CR^{11}$—$CR^{12}$—Y—CZ—;
$R^{11}$ is: H or $R^{11}$ and $R^{12}$ can joined to form an phenyl ring;

$R^{12}$ is: H, ($C_1$-$C_6$)-alkyl, ($C_1$-$C_6$)-alkoxy, —$CH_2$-aryl, $O(CH_2)_{n+1}O(CH_2)_sCH_3$, $(CH_2)_{n+1}O(CH_2)_sCH_3$, or $CH_2N[CH_2CH_2]_2O$;

Y is: O, or S; and

Z is:
- (a) $CO_2R^2$,
- (b) 1H-tetrazol-5-yl,
- (c) $CONHSO_2R^{14}$,
- (d) $SO_2NHR^{14}$,
- (e) $NHSO_2R^{14}$,
- (f) $SO_2NHCOR^{14}$, or
- (g) $NHSO_2CF_3$.

The alkyl substituents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The aryl substituent recited above represents phenyl or naphthyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

GENERAL METHODS FOR PREPARATION OF COMPOUNDS OF GENERAL FORMULA I

The methods described in PART I and PART II below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by formulas Ia through Ic and a substituted benzyl substitutent which is attached to the heterocyclic component at a nitrogen atom. Thus, two generally applicable approaches to antagonists of formula I are these:

1. A heterocycle, designated above with Formulas Ia through Ic is prepared as described in PART I below. Then the heterocycle is alkylated at a nitrogen atom with a substituted benzyl halide or pseudohalide giving an alkylated heterocycle in the Schemes below, this alkylating agent is often designated as "Ar—$CH_2Q$" where Q is a halide (—Cl,Br,I) or pseudohalide (—OMs, OTs, OTf). In some cases, alkylation may take place at more than one nitrogen atom of the heterocycle, and in these cases, separation by fractional crystallization or by chromatographic methods may be necessary for isolation of the desired product. In some cases, the alkylation step produces a fully-assembled antagonist of Formula I, except that functional groups in the alkylating agent or in the heterocycle may be present in protected form and require deprotection steps to be carried out to complete the synthesis. In other cases, the alkylation is carried out with a substituted benzylic halide or pseudohalide ("Ar—$CH_2Q$"), but here the alkylation step is followed by subsequent steps which are required to assemble the substituted benzyl element of the antagonist of Formula I. The alkylation steps and subsequent steps used to prepare antagonists of Formula I, are described in PART II below.

Abbreviations used in the schemes and examples are listed in Table 1.

TABLE 1

| | |
|---|---|
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Reagents | |
| NBS | N-bromosuccinimide |
| AIBN | Azo(bis) isobutyronitrile |
| DDQ | Dichlorodicyanoquinone |
| $Ac_2O$ | acetic anhydride |
| TEA | triethylamine |
| DMAP | 4-dimethylaminopyridine |
| $PPh_3$ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| FMOC-Cl | 9-Fluorenylmethyloxycarbonyl chloride |
| Others: | |
| rt | room temperature |
| TBDMS | t-butyldimethylsilyl |
| OTf | $OSO_2CF_3$ |
| Ph | phenyl |
| FAB-MS (FSBMS) | Fast atom bombardment mass spectroscopy |
| NOE | Nuclear Overhauser Effect |
| $SiO_2$ | silica gel |
| trityl | triphenylmethyl |
| Bn | benzyl |

PART I: Preparation of the heterocycles shown in Formulas Ia, Ib, and Ic

A. Preparation of quinazolinones (Formula Ia)

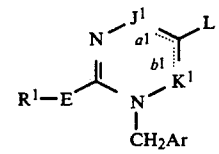

Scheme I-1 illustrates the preparation of 1,2-disubstituted quinazolin-4(1H)-ones of Formula Ia wherein $J^1$=—C(O)— and E is a single bond. An appropriately substituted anthranilonitrile is acylated using the requisite acyl chloride. The resulting amide is alkylated with sodium hydride and the appropriate alkyl halide (or pseudohalide). The resulting tertiary amide is then rearranged/cyclized with basic hydrogen peroxide[1].

SCHEME I-1

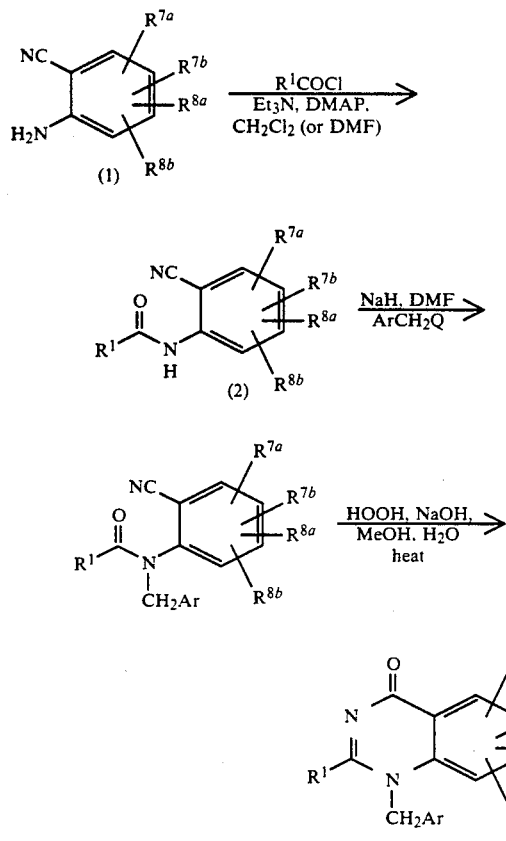

Q = Br, I, OTs, OTf
Ar = is as defined as in the generic structure Formula I

2-Substituted quinazolinones may be prepared from substituted anthranilonitriles as described in the literature and illustrated in Scheme I-2. The appropriately substituted anthranilonitrile is acylated using the requisite acyl chloride then cyclized using basic hydrogen peroxide.[1]

SCHEME I-2

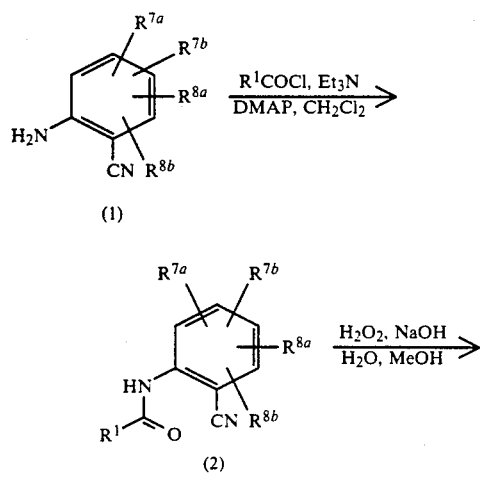

-continued
SCHEME I-2

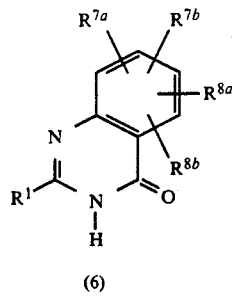

Scheme I-3 shows an alternate preparation of 2-substituted quinazolinones starting with the corresponding anthranilic acid. The appropriately substituted anthranilic acid is treated with two equivalents of the requisite acyl chloride in DMF with triethylamine and DMAP at 0° C. This is then heated to 110° C. for two hours after which time excess ammonium carbonate is added.[2]

SCHEME I-3

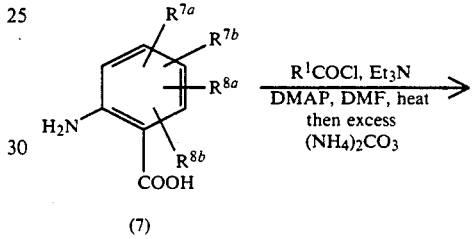

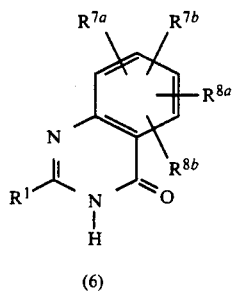

Scheme I-4 illustrates the general preparation of 2,3-disubstituted quinazolin-4-(3H)-ones of Formula Ia, wherein E is a single bond and K[1] is —C(O)—. An appropriately substituted 2-substituted quinazolinone (see Scheme I-2 or Scheme I-3) is alkylated using sodium hydride and the appropriate alkyl halide (or pseudohalide). This reaction sometimes gives some O-alkylated product, generally less than 20% of the isolated reaction products.

SCHEME I-4

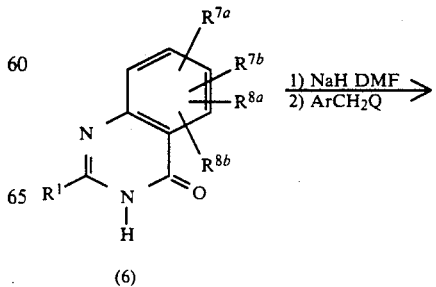

-continued
SCHEME I-4

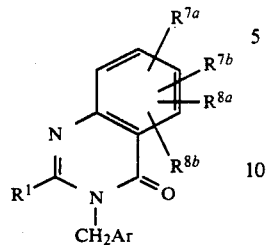

Schemes I-5, I-6, and I-7 provide an alternate route to compounds of Formula Ia, wherein E is a single bond and $K^1$ is —C(O)—.

Two methods for preparing 3,1,4-benzoxazones are illustrated in Scheme I-5. Substituted anthranilic acids may be acylated and cyclized by heating them in DMF with an acyl chloride, triethylamine and DMAP.[3] Alternatively, they may also be prepared by heating an appropriately substituted anthranil with an acyl chloride in pyridine.[4]

The necessary alkyl amine may then be prepared from the alkyl halide (or pseudohalide) using the standard literature procedures (Scheme I-6).[5] Then, the amine and the 3,1,4-benzoxazone are heated together to give the desired 2,3-disubstituted quinazolinone 2 (Scheme I-7).

SCHEME I-5

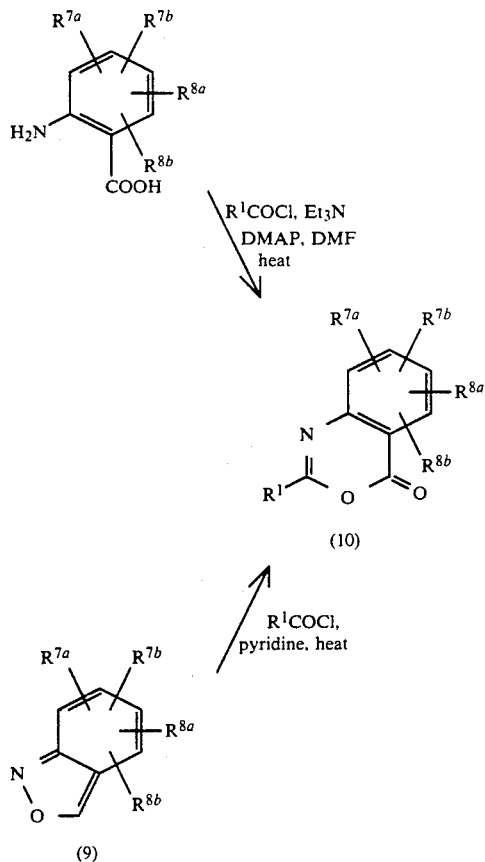

SCHEME I-6

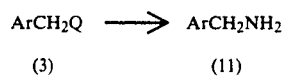

SCHEME I-7

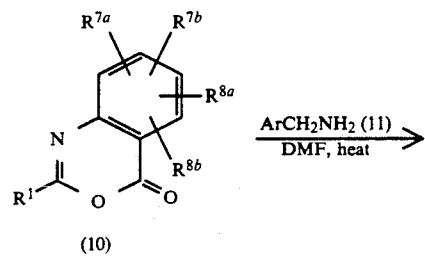

Substituted 2-alkylthioquinazolin-4(3H)-ones wherein $K^1$ is —C(O)— and E is —S— may be prepared from their corresponding substituted anthranilic acids as shown in Scheme I-8. The amine from Scheme I-6 can be converted to its isothiocyanate upon treatment with thiophosgene. This may then be reacted with an appropriately substituted anthranilic acid to give the desired 3-alkyl-2-mercapto-quinazolin-4(3H)-one.[6] A second alkylation of the mercapto group then gives the desired 2-alkylthio-3-alkylquinazolin-4(3H)-one.[7]

SCHEME I-8

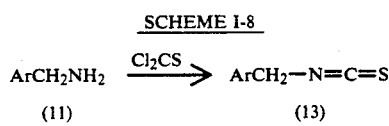

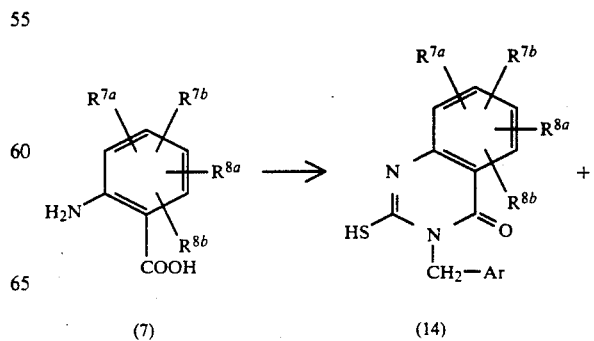

-continued
SCHEME I-8

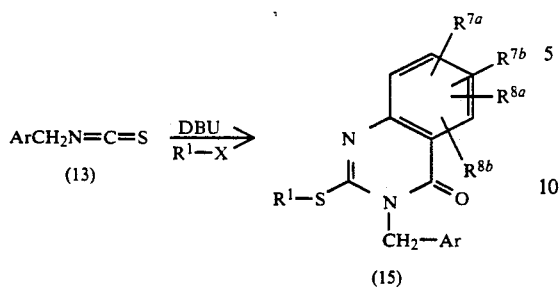

Similarly, 2-alkoxyquinazolin-4(3H)-ones wherein $K^1$ is —C(O)— and B is —O— may be prepared from their corresponding substituted anthranilic acids as shown in Scheme 9.[8] Alkylation with the appropriate alkyl halide according to the methods developed by Lange and Sheibley[9] then gives the final product 17.

SCHEME I-9

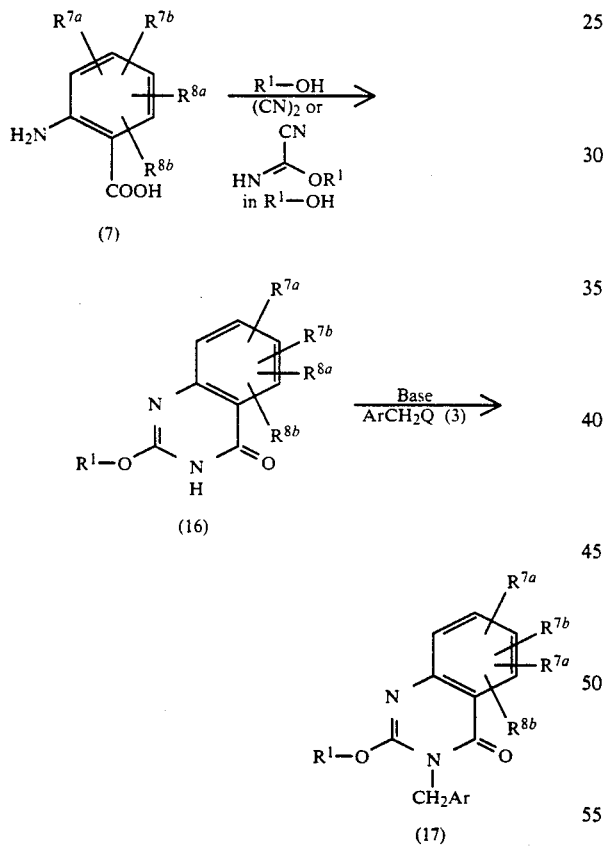

Scheme I-10 illustrates a possible route to the isomeric 1,2-disubstituted quinazolin-4(1H)-ones wherein $J^1$ is —C(O)— and wherein E is —S— or —O—. An anthranilonitrile can be acylated with an alkyl haloformate or an alkylthiol haloformate.[10] This may then be deprotonated and alkylated with the appropriate alkyl halide to give the intermediate carbamate nitrile shown.[11] Conversion of the intermediate then could occur when the material is treated with basic hydrogen peroxide to yield the desired product 20.

SCHEME I-10

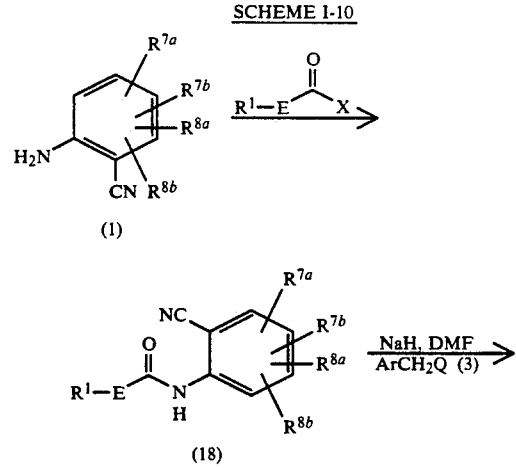

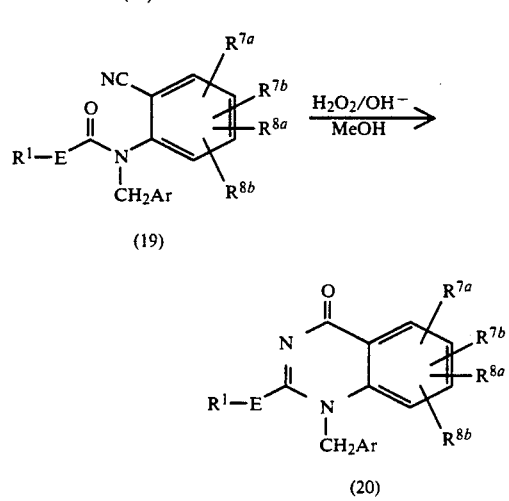

Scheme I-11 illustrates the method by which a 2-amino-3-alkylquinazolinone can be made. The 2-mercaptoquinazolinone (14) shown in Scheme I-8 can be treated with sulfuryl chloride to give the corresponding 2-chloroquinazolinone.[12] Displacement of the chloride with an $R^1$ amine then gives 20 with B=NH.[13]

SCHEME I-11

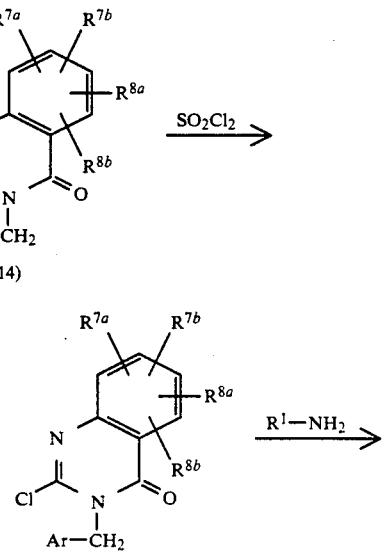

SCHEME I-11 -continued

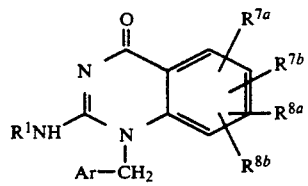

(20)

Scheme I-12 illustrates the method by which a 2-amino-1-alkylquinazolinone can be made. The products from Scheme I-10 can be used as a synthetic intermediate if the initial R[1] is a protecting group such as benzyl or t-butyl.[14] Deprotection and subjection of the resulting 2-mercapto-1-alkyl-quinazolinone to the same conditions used in Scheme I-11 will result in the formation of the desired 2-amino-1-alkylquinazolin-4(1H)-one. Alternatively, the sulfide may be displaced directly by an R[1] amine as shown in Scheme I-13 (R[1]—S— and R[1]—NH$_2$ may or may not have the same R[1]).

SCHEME I-12

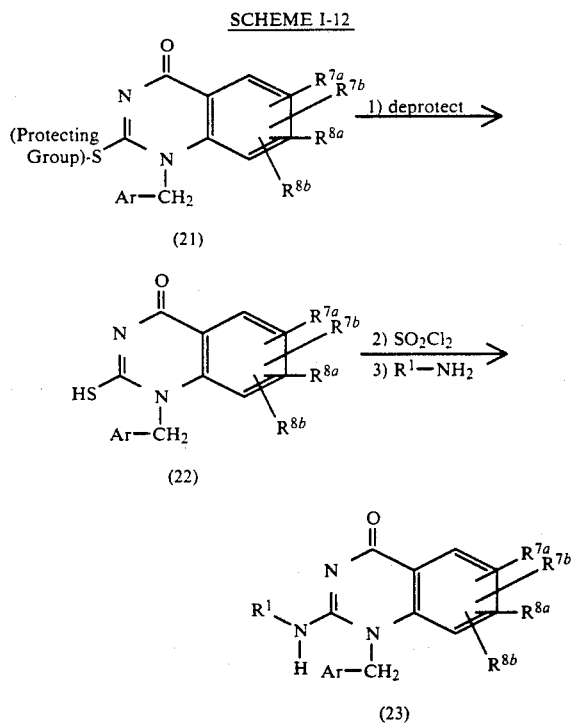

SCHEME I-13

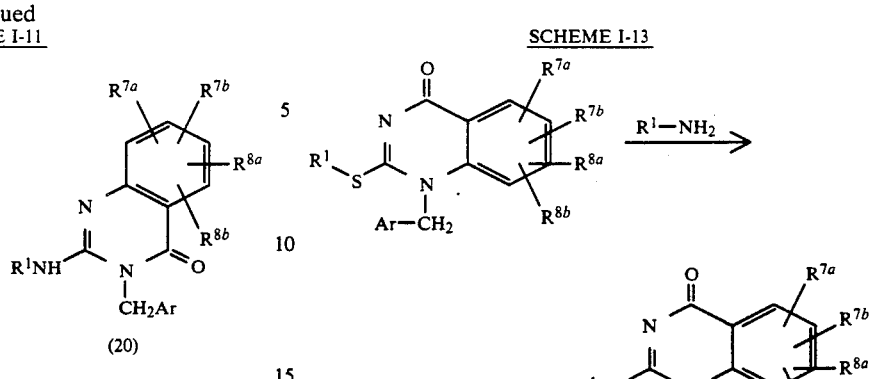

The preparation of quinazolinones of general Formula Ia bearing substituted C-6 amino groups may be accomplished as illustrated in Schemes I-14 through I-16. In order to prepare these derivatives, the amide group of a 6-nitroquinazolin-4(3H)-one is usually first protected with an acid labile protecting group as shown in Scheme I-14. For instance, reaction of the generalized 6-nitroquinazolin-4(3H)-one (24) with a base such as sodium hydride in DMF followed by addition of bis(4-methoxyphenyl)methyl chloride affords the N-protected derivative 25. The nitro group of 25 may be reduced to the amine 26 by reduction with hydrogen over palladium on carbon. The amine (26) may then be reacted with a variety of reagents known to form derivatives of amines such as alkyl- or aryl-carboxylic acid chlorides, chloroformates, sulfonyl and sulfamoyl chlorides, isocyanates and isothiocyanates. Scheme I-14 illustrates the derivatization of amine 26 with a generalized chloroformate to afford substituted carbamates such as 27. The acylation of amine 26 with a chloroformate is best carried out in the presence of a strong base such as sodium hydride to deprotonate the amine. This anion then reacts readily with chloroformates to give the substituted carbamates 27. The carbamate (27) may be isolated, then deprotonated with lithium bis(trimethylsilyl)amide and alkylated to give the N,O-disubstituted carbamates 28. Alternatively, this process may be carried out in one flask by first deprotonating the aniline (i.e. with sodium hydride in DMF), reacting the anion with an acyl halide or chloroformate, then treating the intermediate with an equivalent of a strong base such as lithium bis(trimethylsilyl)amide and finally adding an alkylating agent to obtain 28. The carbamoyl-substituted quinazolinones 27 and 28 may be cleanly deprotected under acidic conditions such as trifluoroacetic acid-anisole to afford the heterocycles 29 and 30 respectively.

SCHEME I-14

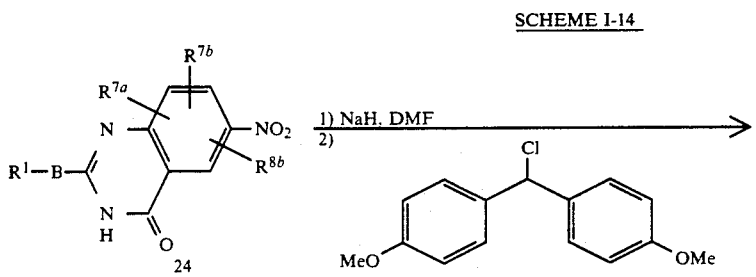

-continued
SCHEME I-14
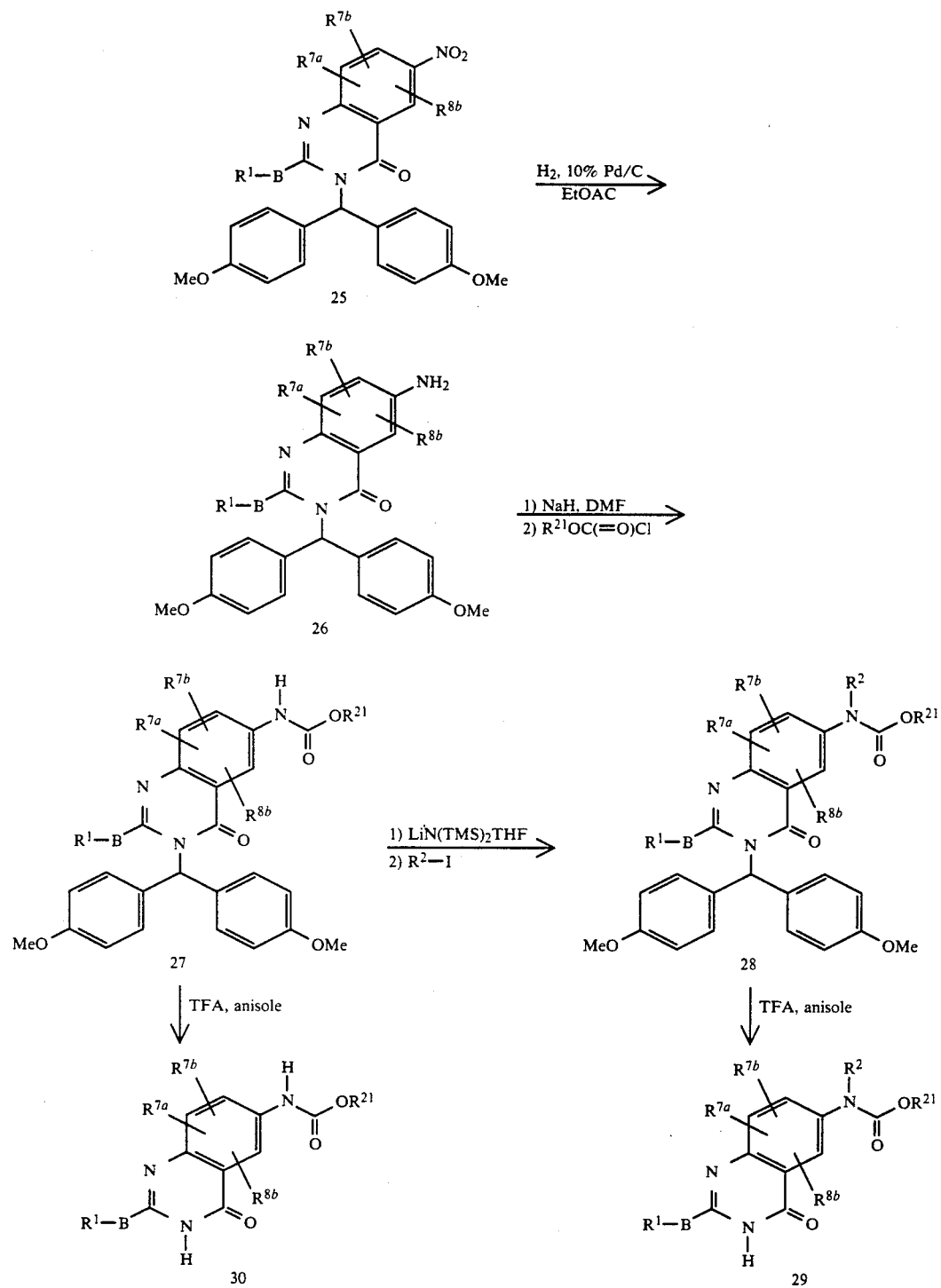

SCHEME I-15

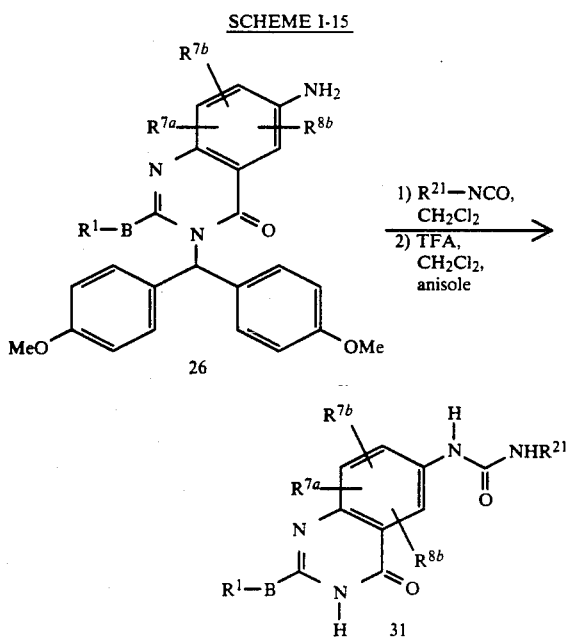

Scheme I-15 illustrates the reaction of amine 25 with isocyanates to give disubstituted ureas (31). Tetrasubstituted and trisubstituted ureas such as 34 and 35 may be prepared from the benzyl carbamate 27 as shown in Scheme I-16. Thus, treatment of 27 with the magnesium salt of a secondary amine formed from the secondary amine and methylmagnesium bromide affords the trisubstituted urea 32. Trisubstituted ureas (32) may be N-alkylated by deprotonation of the remaining hydrogen with lithium bis(trimethylsilyl)amide followed by alkylation with an alkyl iodide to give 33. The urea-substituted quinzolines 32 and 33 may be cleanly deprotected under acidic conditions such as trifluoroacetic acid-anisole to afford the heterocycles 34 and 35 respectively. The amine 26 (Scheme I-14) may be derivatized or converted to other functional groups using chemical procedures well known to those skilled in the art. After the appropriate 6-substituent has been constructed the protecting group may be removed by treatment with trifluoroacetic acid in the presence of anisole as illustrated in Schemes I-14 through I-16. The heterocycles obtained in this manner may be incorporated into Angiotensin II Antagonists of general Formula Ia as described in Part II.

SCHEME I-16

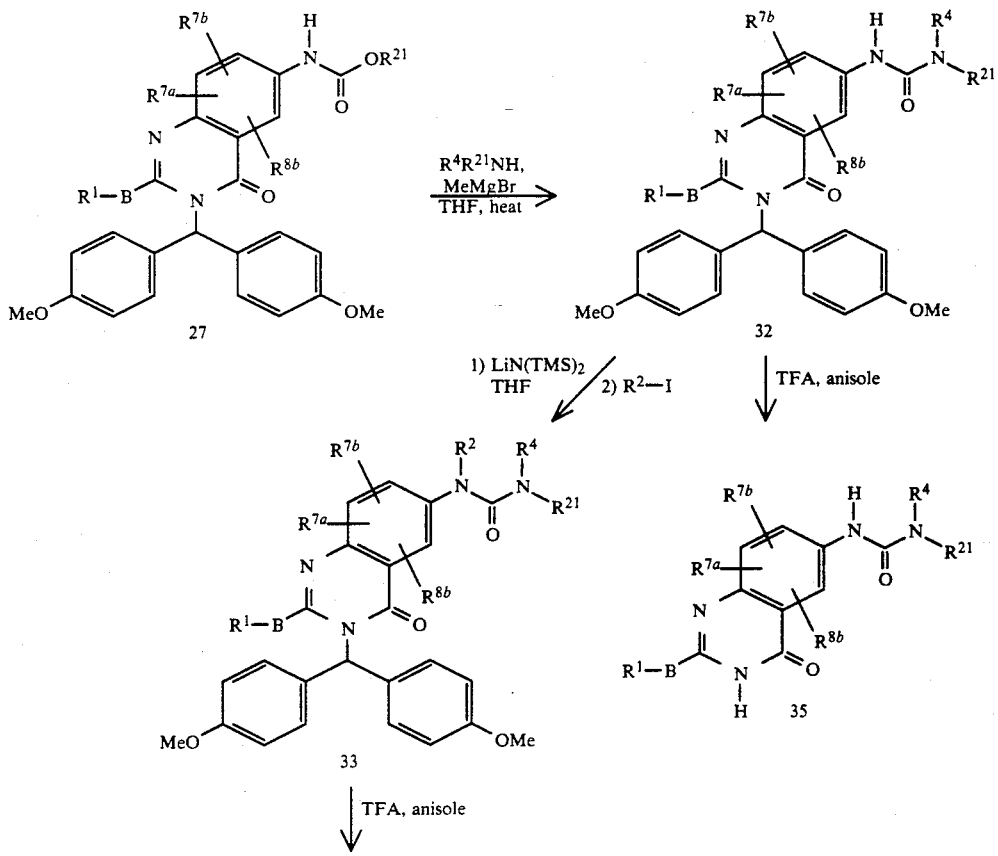

SCHEME I-16

-continued

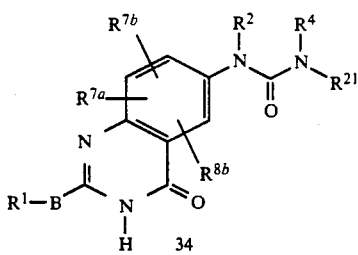

For a general review of the synthesis and reactivity of 2,3-disubstituted pyrido[2,3-d] or [3,4-d] or [3,2-d] or [4,3-d]pyrimidin-4(3HO-ones, see A. R. Katritzky, et al., *Comprehensive Heteocyclic Chemistry*, vol. 3, 201 (1984) and W. J. Irwin, et al., *Advances in Heterocyclic Chemistry*, vol. 10, 149 (1969).

QUINAZOLINONE REFERENCES

[1] E. C. Taylor, R. J. Knopf, A. L. Borror, *J. Am. Chem. Soc.* (1960) 82, 3152.

R. L. McKee, M. K. McKee, R. W. Bost, *J. Am. Chem. Soc.* (1964), 68, 1902.

A. Khan, R. K. Saksena, *Pharmazie* (1988) 43 H, 12.

[2] M. T. Bogert, W. F. Hand, *J. Am. Chem. Soc.* (1906) 28, 94.

[3] See A. Khan, reference 1.

L. A. Errede, J. J. McBrady, H. T. Oien, *J. Org. Chem.* (1977) 42, 656.

L. A. Errede, *J. Org. Chem.* (1976) 41 1763.

L. A. Errede, H. T. Oien, D. R. Yarian, *J. Org. Chem.* (1977) 42, 12.

[4] K. Wunsch, A. J. Boulton, *Adv. Het. Chem.* (1967) 8, pp 326-9, and references therein.

I. R. Gambhir, S. S. Joshi, *J. Ind. Chem. Soc.* (1964) 41, 47.

[5] Bayley, Stranding, Knowles, *Tetrahedron. Lett.* (1978) 3633.

Rólla, *J. Org. Chem.* (1982) 47, 4327.

Gibson, Bradshaw, *Angew. Chem. Int. Ed. Engl.* (1968) 7, 919.

[6] R. G. Dave, G. S. Mewada, G. C. Amin, *J. Ind. Chem. Soc.* (1960) 37, 595.

[7] J. E. McCarty, E. L. Haines, C. A. VanderWerf, *J. Am. Chem. Soc.* (1960) 82, 964.

P. N. Bhargava, P. Ram, *Bull. Chem. Soc. Jap.* (1965) 38, 342.

M. R. Chaurasia, A. K. Sharma, *Heterocycles* (1983) 20, 1549.

K. Lempert, G. Doleschall, *Chem. Ber.* (1963) 96, 1271.

H. Singh, K. S. Narang, *J. Ind. Chem. Soc.* (1963) 40, 545.

M. S. Dhatt, K. S. Narang, *J. Ind. Chem. Soc.* (1954) 31, 787.

M. S. Dhatt, K. S. Narang, *J. Ind. Chem. Soc.* (1954) 31, 864.

D. S. Bariana, H. S. Sachdev, K. S. Narang, *J. Ind. Chem. Soc.* (1955) 32, 647.

[8] Griess, *Ber. Deut. Chem. Ges.* (1869) 2, 415.

[9] N. A. Lang, F. E. Sheibley, *J. Am. Chem. Soc.* (1933) 55, 1188.

[10] H. B. Milne, S. L. Razniak, R. P. Bayer, D. W. Fish, *J. Am. Chem. Soc.* (1960) 82, 4582.

E. J. Corey, M. G. Bock, A. P. Kozkowski, A. V. R. Rao, D. Floyd, B. Lipschutz, *Tetrahedron Lett.* (1978) 1051.

M. Bergmann, L. Zervas, *Ber.* (1932) 65 1192.

[11] R. L. Dannley, M. Lukin, *J. Org. Chem.* (1957) 22, 268.

R. Zibuck, N. J. Liverton, A. B. Smith, *J. Am. Chem. Soc.* (1986) 10,8 2451.

[12] D. J. Brown, *Fused Pyrimidines*, Part I Quinazolines, (1967), J. Wiley & Sons, p. 222.

[13] D. J. Brown, *Fused Pyrimidines*, Part I Quinazolines, (1967), J. Wiley & Sons, p. 323.

[14] T. W. Greene, *Protective Groups in Organic Synthesis*, (1981), J. Wiley & Sons, pp. 193-217.

B. Preparation of triazolinones, triazolinethiones and triazolinimines (Formula Ib)

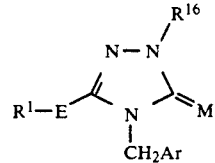

The compounds of Formula Ib can be prepared by a variety of methods typified by those described below in Schemes I-17 to I-28. General synthetic methods for 2,4,5-trisubstituted-1,2,4-triazolin-3(4H)-ones and -triazolin-3(4H)-thiones are discussed in books or review articles such as:

(1) C. Temple and J. A. Montgomery, "Triazoles: 1,2,4" (Vol. 37 of *The Chemistry of Heterocyclic Compounds*, A. Weissberger and E. C. Taylor, eds.), Wiley-Interscience, New York, 1981, pp. 365-442.

(2) J. B. Polya, *Comprehensive Heterocyclic Chemistry, The Structure, Reactions, Synthesis and Uses of Heterocyclic Compounds*, A. R. Katritzky and C. W. Rees, eds., Vol. 5, Pergamon Press, Oxford, 1984, pp. 733-790.

(3) J. H. Boyer, *Heterocyclic Compounds*, R. C. Elderfield, ed., Vol. 7, John Wiley & Sons, New York, 1961 pp. 384-461.

In general, the compounds of Formula Ib are constructed in such a way that $N^1$ and $N^2$ of the triazole ring are derived from hydrazine or a hydrazine derivative, while $N^4$ of the triazole and the 4-(arylmethyl) substituent are derived directly or indirectly from a suitably substituted benzylamine (or isocyanate or isothiocyanate) or from a benzyl halide (or methanesulfonate, p-toluenesulfonate, etc.).

Although the Reaction Schemes described below are reasonably general, it will be understood by those skilled in the art of organic synthesis that one or more functional groups present in a given compound of Formula Ib may render the molecule incompatible with a particular synthetic sequence. In such a case an alternative route, an altered order of steps, or a strategy of protection and deprotection may be employed. In all cases the particular reaction conditions (including reagents, solvent, temperature, and time) should be chosen so that they are consistent with the nature of the functionality present in the molecule.

The Reaction Schemes below have been generalized for simplicity. It is to be understood that the "ArCH$_2$" substituent present at N$^4$ of the triazole derivatives or in their precursors is any substituted arylmethyl moiety consistent with the definition of the N$^4$ substituent in Formula I or which may be transformed to such a grouping either before or after the assembly of the triazole ring system. Such transformations may involve protection and/or deprotection steps, as described above in the "General Methods" section or other modifications. It is also to be understood that in most of the Reaction Schemes, the "ArCH$_2$" (Ar=aryl) substituent is consistent with the definition of Formula I.

It is further to be understood that in the generalized schemes below, unless specified otherwise, the R$^1$ and R$^{16}$ groups represent functionalized or unfunctionalized alkyl, aryl, heteroaryl, aralkyl, and the like. The moiety, R$^{16}$Q, represents an alkylating agent in which R$^{16}$ is typically a functionalized or unfunctionalized alkyl or aralkyl group, while Q is a leaving group such as chloro, bromo, iodo, methanesulfonate, or p-toluenesulfonate. In structures showing an "X" group double-bonded to a carbon atom (as in 22 and products derived therefrom), M is O or S.

REACTION SCHEME I-17

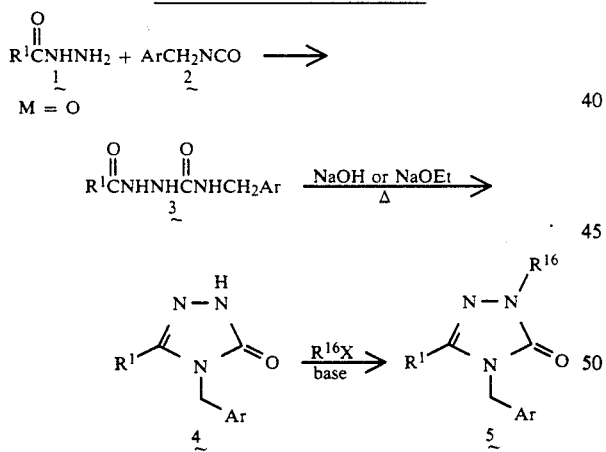

One of the most widely used routes to 2,4,5-trisubstituted-2,4-dihydro-3H-1,2,4-triazol-3-ones (2,4,5-trisubstituted-1,2,4-triazolin-3(4H)-ones) is shown in Reaction Scheme I-17 in its adaptation for the synthesis of compounds of Formula Ib. Reaction of a carboxylic acid hydrazide 1 (readily obtained from the corresponding ester) with the appropriate arylmethyl isocyanate 2 gives the 1-acyl-4-(arylmethyl)semicarbazide 3. The isocyanate 2 itself is obtainable by well-known methods from various sources, including the (arylmethyl)amine (by phosgene treatment), the arylmethyl halide (by treatment with cyanate anion), and the arylacetic acid or derivative (via Curtius rearrangement of the acyl azide). Upon heating in the presence of hydroxide or alkoxide, cyclization of 3 to the triazolinone 4 occurs. Finally, in the presence of a base (e.g., sodium hydride, sodium ethoxide, sodium hydroxide, or potassium carbonate), 4 is converted to the trisubstituted triazolinone 5 on treatment with a suitable alkylating agent R$^{16}$Q, where R$^{16}$ is alkyl, aralkyl, etc., and Q is bromo, iodo, chloro, methanesulfonate, p-toluenesulfonate, and the like. Such reaction pathways have been described by D. L. Temple, Jr., and W. G. Lobeck, Jr., U.S. Pat. No. 4,487,773 (1984), R. E. Gammans, D. W. Smith, and J. P. Yevich, U.S. Pat. No. 4,613,600 (1986), and (in part) H. Gehlen and W. Schade, *Liebegs Ann. Chem.* 675, 180 (1964), G. Palazoo, U.S. Pat. No. 3,857,845 (1974), and K. H. Hauptmann and K. Zeile, British Patent 971,606 (1964). A modified approach to an intermediate of type 3 and its subsequent cyclization to a triazolinone analogous to 4 have been reported by H. Hrebabecky and J. Barenek, *Collect. Czech. Chem. Commun.*, 50, 779 (1985).

REACTION SCHEME I-18

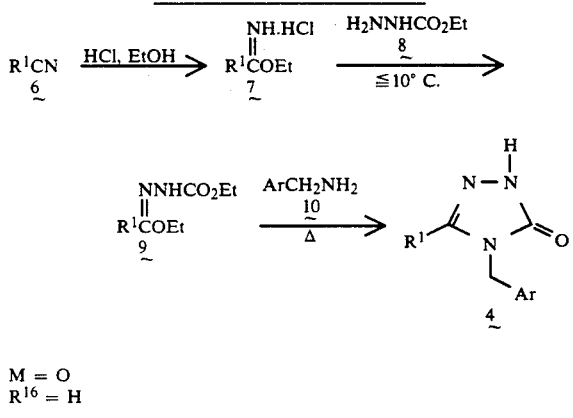

M = O
R$^{16}$ = H

A highly useful alternative route to 4 is shown in Reaction Scheme I-18. This approach has been described by M. Pesson, S. Dupin, and M. Antoine, *Compt. Rend.*, 253, 285 (1961) and R. Un and A. Ikizler, *Chim. Acta. Turc.*, 3, 113 (1975). Addition of ethyl carbazate (8) to the imidate 7 (which is readily prepared from the corresponding nitrile 6) yields an adduct 9, which can be converted to the triazolinone 4 on heating with the (arylmethyl)amine 10 (typically at temperatures from 70°-150° C.) As in Reaction Scheme I-17, 4 can be alkylated to give the trisubstituted triazolinone 5.

REACTION SCHEME I-19

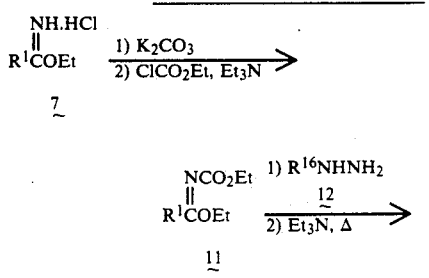

-continued
REACTION SCHEME I-19

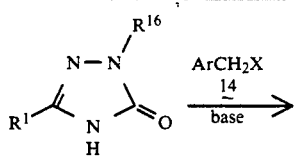

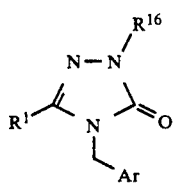

$R^{16}$ = aryl
M = O

The procedures of Reaction Schemes I-17 and I-18 are not suitable for the introduction of most aryl or heteroaryl substituents at $N^2$. In contrast, the procedures of Reaction Schemes I-19 to I-22 are especially well suited for the synthesis of compounds of Formula Ib having aryl or heteroaryl substituents at $N^2$, since the triazolinone ring is constructed with the $N^2$-substituent in place, whereas the $N^4$-substituent is introduced subsequently by alkylation. Reaction Scheme I-19 presents a route patterned after that reported by K. Yabutani, K. Taninaka, M. Kajioka, K. Takagi, H. Matsui, K. Sutoh, and M. Yamamota, European Patent Application 220, 952 (1987). The N-carbethoxy imidate 11 (obtained by reaction of 7 with ethyl chloroformate) is treated with an arylhydrazine 12 (or analog), typically at about 40°-50° C.) in the presence of a tertiary amine such as triethylamine which effects cyclization to the triazolinone 13. In the presence of a suitable base (e.g., sodium hydride, sodium alkoxide, sodium hydroxide) treatment of 13 with the appropriate ArCH$_2$Q, where Q=bromo, iodo, chloro, methane-sulfonate, p-toluenesulfonate, and the like, yields the $N^4$-alkylated product 15. A variant of the method using a thioimidate has been described by M. Kajioka, H. Kurono, K. Okawa, and M. Harada, U.S. Pat. No. 4,318,731 (1982).

REACTION SCHEME I-20

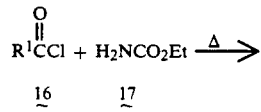

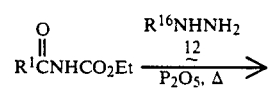

-continued
REACTION SCHEME I-20

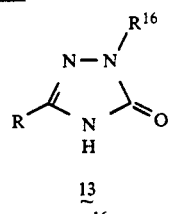

$R^{16}$ = aryl

An alternative route to the $N^2$-substituted triazolinone intermediate 13 is shown in Reaction Scheme I-20. This chemistry has been described by T. N. Gosh and M. V. Betrabet, *J. Indian Chem. Soc.*, 7, 899 (1930), S. Bellioni, *Ann. Chim. (Rome)*, 52, 187(1962), G. Palazzo and G. Picconi, *Boll. Chim. Farm.*, 105, 217 (1966), and British Patent 1,021,070 (1966). An acid chloride 16 is heated with urethane (17) (typically at 80°-100° C.), to give the acylurethane 18. Reaction of 18 with an arylhydrazine 12 and phosphorus pentoxide (usually in toluene or xylene at reflux) gives 13, which can then be further alkylated on $N^4$ as in Reaction Scheme I-19. A (thioacyl)urethane modification of this pathway has been reported by D. L. Temple, Jr., and W. G. Lobeck, Jr., U.S. Pat. No. 4,487,773 (1984).

REACTION SCHEME I-21

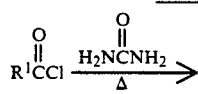

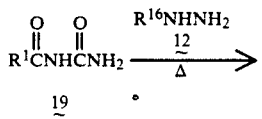

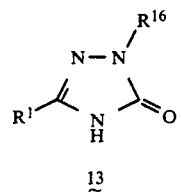

$R^{16}$ = aryl
M = O

A variation of Reaction Scheme I-20, shown in Reaction Scheme I-21, has been described by P. Gold-Aubert, D. Melkonian, and L. Toribio, *Helv. Chim. Acta*, 47, 1188 (1964) and A. L. Langis, U.S. Pat. No. 3,499,000 (1970). The readily prepared acylurea 19 upon heating with an arylhydrazine 12 (at about 150°-200° C.) is converted to the triazolinone intermediate 13.

REACTION SCHEME I-22

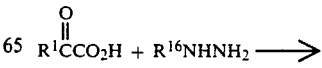

-continued
REACTION SCHEME I-22

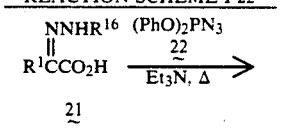

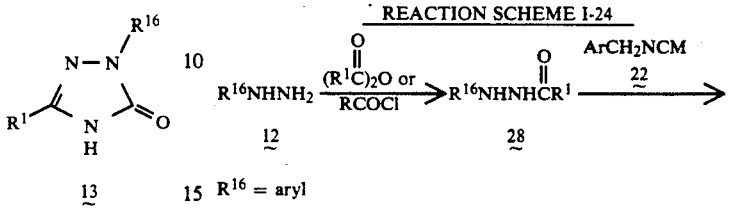

$R^{16}$ = aryl
M = O

In a quite different approach (Reaction Scheme I-22), L. Maravetz, U.S. Pat. No. 4,705,557 (1987) and G. Theodoridis, International Patent Application WO87/03782 (1987) disclose condensing an α-keto acid 20 with the arylhydrazine 12 to give derivatives such as 21, which can be converted to the triazolinone intermediate 13 by heating with diphenylphosphoryl azide and triethylamine (typically at 75°–115° C.). In the last step, an intermediate acyl azide loses nitrogen and undergoes the Curtius rearrangement to an isocyanate, which undergoes ring closure. As shown in Reaction Scheme I-19, 13 can then be alkylated on $N^4$ to give the trisubstituted triazolinone 15.

REACTION SCHEME I-23

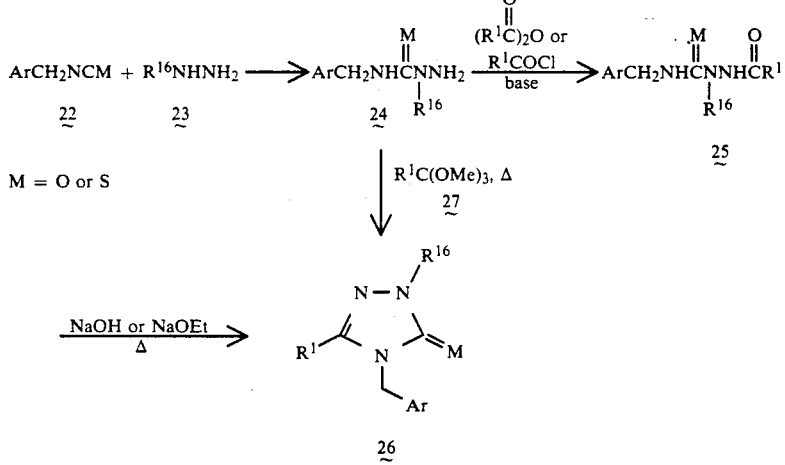

M = O or S 2,4,5-Trisubstituted-2,4-dihydro-3H-1,2,4-triazole-3-thiones (2,4,5-trisubstituted-1,2,4-triazolin-3(4H)-thiones) cannot generally be prepared by routes analogous to those in Reaction Schemes I-17 to I-22 because of the propensity for alkylation to occur on sulfur rather than on the open ring nitrogen. It is thus preferable to have all of the substituents in place at the time of the ring closure to form the heterocycle. As shown in Reaction Scheme I-23, for certain $R^{16}$ groups (e.g., $R^{16}$=$CH_3$), reaction of the hydrazine derivative 23 with the appropriate isocyanate or isothiocyanate 22 yields the 2,4-disubstituted semicarbazide or thiosemicarbazide 24. Acylation of 24 gives 25, which can be cyclized upon heating with hydroxide or alkoxide to give the trisubstituted triazolinone or triazolinethione 26. This approach has been detailed by J. M. Kane and F. P. Miller, U.S. Pat. No. 4,775,688 (1988) and G. F. Duffin, J. D. Kendall, and H. R. J. Waddington, *J. Chem. Soc.*, 3799 (1959). Alternative methods of ring closure, such as heating 24 with the orthoester 27, can also be utilized.

REACTION SCHEME I-24

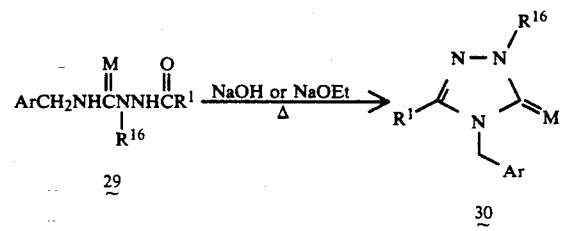

$R^{16}$ = aryl

In Reaction Scheme I-24, acylation of an aryl- or heteroaryl hydrazine gives 28, which can be reacted with the isocyanate or isothiocyanate 22 to yield the 1-acyl-2,4-disubstituted-semicarbazide or -thiosemicarbazide 29. Cyclization of 29 upon heating with hydroxide or alkoxide affords the triazolinone or triazolinethione 30. This chemistry has been described by H. Gehlen and W. Schade. *Liebigs Ann. Chem.*, 675, 180 (1964).

REACTION SCHEME I-25

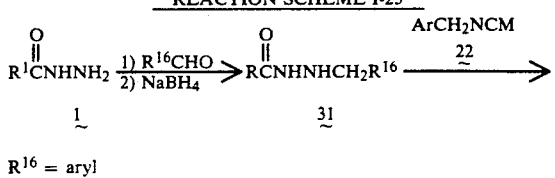

$R^{16}$ = aryl

-continued
REACTION SCHEME I-25

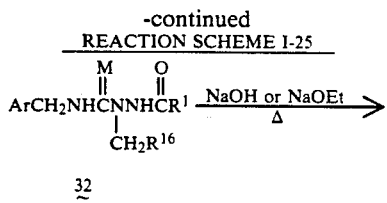

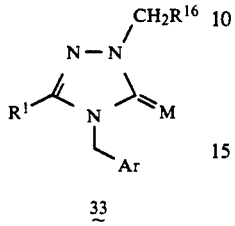

REACTION SCHEME I-26

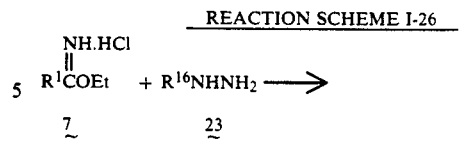

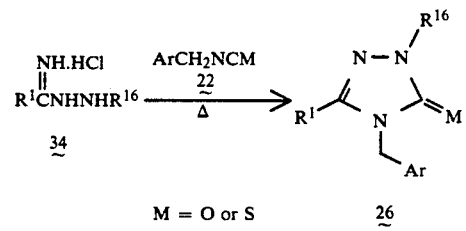

The method of F. Russo, M. Santagati, and G. Pappalardo [*Ann. Chim.* (Rome), 62, 351 (1972] (Reaction Scheme I-45) is useful for the synthesis of trisubstituted triazolinones and triazolinethiones having benzylic substituents at $N^2$. Treatment of a hydrazide 1 with an aromatic or heteroaromatic aldehyde followed by reduction with sodium borohydride gives the substituted hydrazide 31. Reaction of 31 with the isocyanate or isothiocyanate 22 affords the semicarbazide or thiosemicarbazide derivative 32, which is cyclized to the triazolinone or triazolinethione 33 upon heating with hydroxide or alkoxide.

In another approach (Reaction Scheme I-26), imidate 7 is treated with a substituted hydrazine 23 (especially an aryl or heteroaryl hydrazine) to give the amidrazone 34. Heating 34 with the isocyanate or isothiocyanate 22 gives the triazolinone or triazolinethione 26. Syntheses of this type have been reported by M. Santus, *Acta Pol. Pharm.* 37, 293 (1980); T. Bany, *Rocz. Chem.*, 42. 247 (1968); and, T. Bany and M. Dobosz, *Ann. Univ. Mariae Curie-Sklodowska, Sect., AA*, 26/27, 23 (1971).

REACTION SCHEME I-27

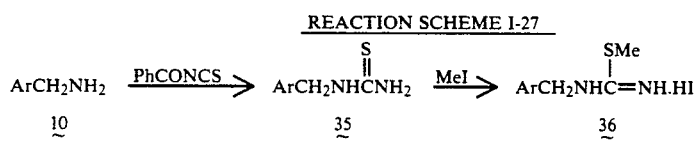

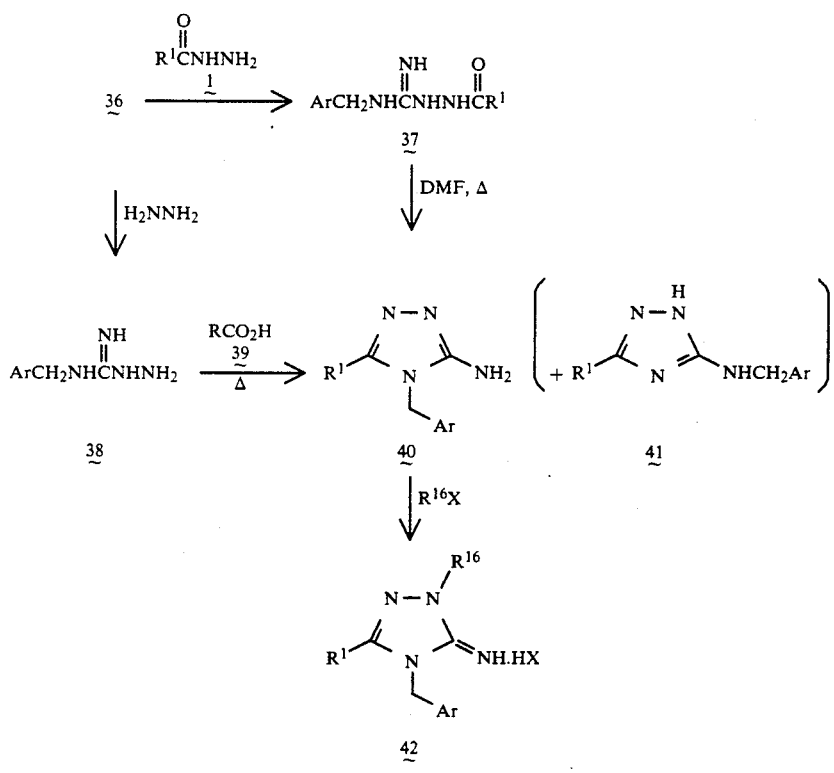

A route to 2,4,5-trisubstituted-2,4-dihydro-3H-1,2,4-triazol-3-imines (2,4,5-trisubstituted-1,2,4-triazolin-3(4H)-imines) is outlined in Reaction Scheme I-27. Reaction of the (arylmethyl)amine 10 with benzoyl isothiocyanate (or by the other means) gives the substituted thiourea 35, which is methylated to prepare the isothiourea derivative 36. Compound 36 can be transformed to the acrylaminoguanidine 37 by reacting with the hydrazide 1 or to the aminoguanidine 38 by reacting with hydrazine. Ring closure of 37 by heating in DMF or cyclization of 38 with carboxylic acid 39 at elevated temperature affords the aminotriazole 40, which can be separated from the isomer 41. Such pathways have been described by G. J. Durant, G. M. Smith, R. G. W. Spickett, and S. H. B. Wright, *J. Med. Chem.*, 9, 22 (1966) and E. Akerblom, *Acta Chem. Scand.*, 19, 1135 (1965). Finally, alkylation of 40 with the appropriate Ar—CH$_2$—Q (where Q is a leaving group such as iodo, bromo, chloro, p-toluenesulfonate, or methanesulfonate) leads to the triazolinimine 42, which can be separated from any other isomers or by-products formed during the reaction. This method has been described by E. B. Akerblom and D. E. S. Campbell, *J. Med. Chem.*, 16, 312 (1973).

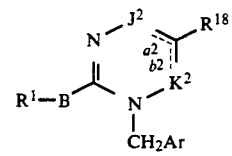

Pyrimidinones of formula Ic (wherein J$^2$ is —C(O)—) substituted in the 1,2,5, and 6-positions may be synthesized as shown in Scheme I-29. Amidines with an R$^1$ substituent may be reacted with a β-carbonyl ester to give a 4-hydroxypyrimidine. Conversion of the hydroxy group to a chloride then to an amine can be achieved by first treating the 4-hydroxypyrimidine with POCl$_3$ then with ammonia.[1] Reaction of the 4-aminopyrimidine with the appropriate alkyl halide followed by treatment with aqueous hydroxide gives the substituted pyrimidin-4(1H)-one.

REACTION SCHEME I-28

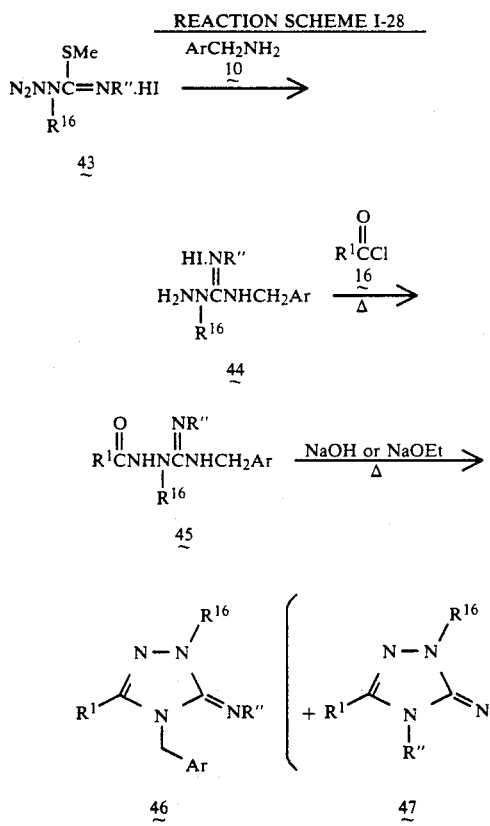

The route shown in Reaction Scheme I-28 utilizes chemistry reported by E. Akerblom, *Acta Chem., Scand.*, 19, 1135 (1965). The substituted isothiourea 43 is treated with amine 10 to give the aminoguanidine derivative 44. Acylation of 44 with the acid chloride 16 provides the intermediate 45, which can be cyclized by heating the hydroxide or alkoxide. The desired triazolinimine 46 is separated from the isomeric product 47.

C. Preparation of Pyrimidinones (Formula Ic)

The compounds of Formula Ic wherein either J$^2$ or K$^2$ is —C(O)— are synthesized as illustrated in Schemes I-29 to I-41 below.

SCHEME I-29

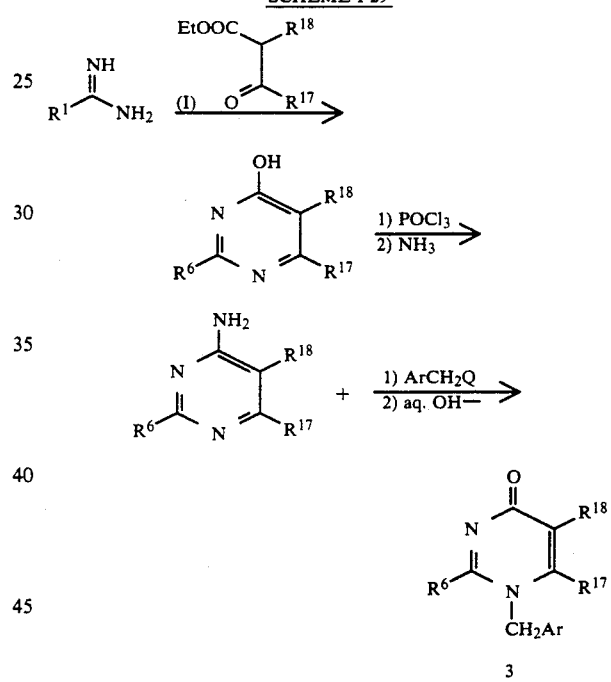

Q is a leaving group (—Cl, —Br, —I, —OTs, etc.).

Scheme I-30 provides the method by which the isomer (wherein K$^2$ is —C(O)—) 2,3,5, and 6-substituted pyrimidinones may be synthesized. A β-carbonyl ester is converted into its corresponding β-aminocrotonate with ammonia.[3] This is then acrylated with an R$^1$-containing acyl chloride (R$^1$COCl) and cyclized to a 3,1-oxazin-4-one. When the 3,1-oxazin-4-one is reacted with the substituted benzylamine, the desired fully substituted pyrimidione 4 results.[4]

SCHEME I-30

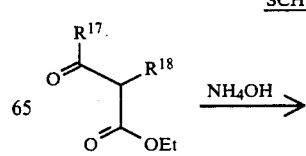

-continued
SCHEME I-30

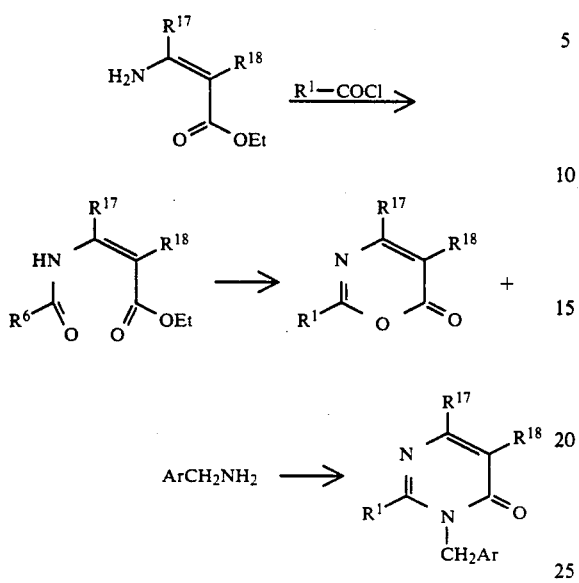

Alternatively, Scheme I-31 shows how an $R^6$ imidate may be converted to an amidine with the substituted benzylamine, followed by treatment with an appropriately substituted β-carbonyl ester to give the desired pyrimidinone 4.[5]

SCHEME I-31

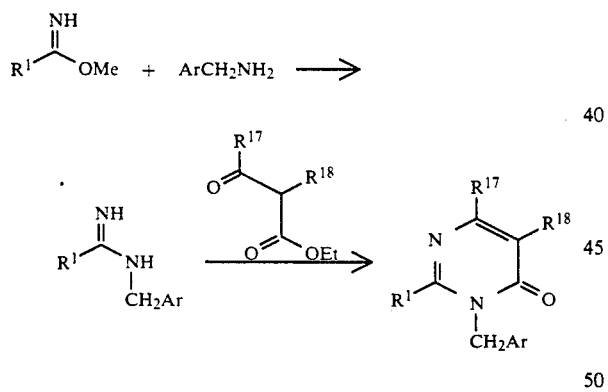

A third alternative is illustrated in Scheme I-52. A simple amidine can be reacted with an appropriately substituted β-carbonyl ester to give the 3-unsubstituted pyrimidinone. This can then be alkylated at the 3-position with KOH is methanol (or with NaH in DMF) and the appropriately substituted alkyl halide to give 4.

SCHEME I-32

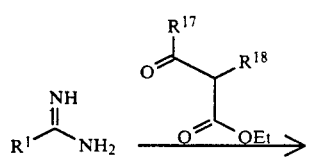

-continued
SCHEME I-32

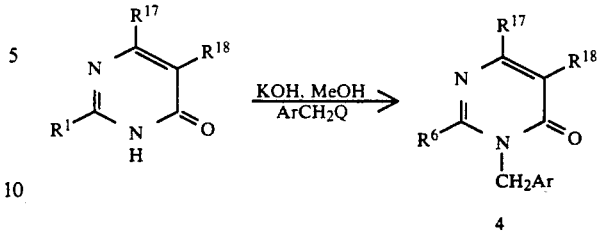

Scheme I-33 illustrates the general synthesis of pyrimidinones of Formula Ic in which B is a sulfur atom. Thiourea when condensed with a β-carbonyl ester gives the 2-thiouracil. This can be bis-trimethylsilylated using hexamethyldisilazane, then alkylated sequentially on the 1-nitrogen atom and then on the sulfur atom using chemistry developed by H. Vorbruggen and P. Strehlke.[6] By this method, one can then obtained compounds of Formula Ic wherein $J^2$ is —C(O)— and B is a sulfur atom.

SCHEME I-33

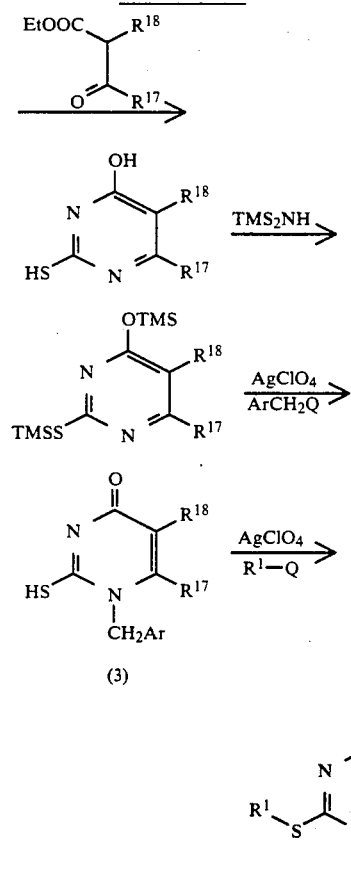

(3)

Q is Br, Cl, I, F, OTs, OTf, etc.

The isomeric 2,3-dialkylated thiouracils may be synthesized as shown in Scheme I-34. Thiourea can be condensed with an appropriately substituted β-carbonyl ester to give the 5,6-disubstituted-2-thiouracil.[7] This may then be alkylated sequentially at the sulfur with an $R^1$ halide, and then at the nitrogen atom with an appropriately substituted alkyl halide to give the desired tetrasubstituted pyrimidinone 4.

SCHEME I-34

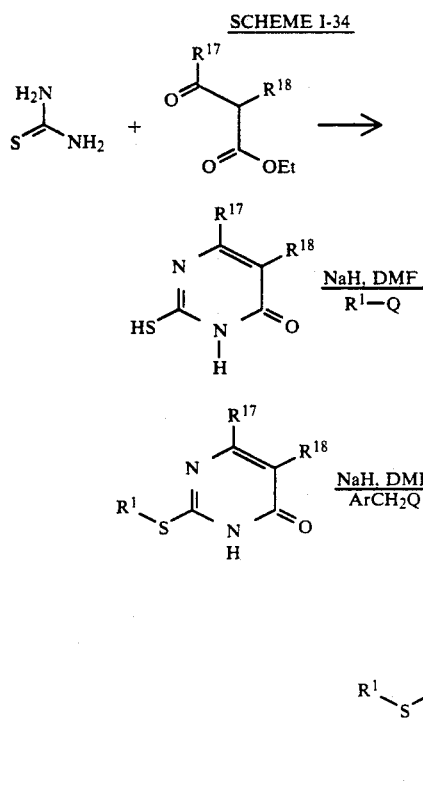

Alternatively, as illustrated in Scheme I-35, an isothiocyanate can be converted into a thiourea by the addition of ammonia.[8] This can then be condensed with the appropriately substituted β-carbonyl ester to give the 3,5,6-trisubstituted-2-thiouracil.[9] Alkylation at the sulfur atom with base and an $R^1$ halide then gives the desired pyrimidinone 4.

SCHEME I-35

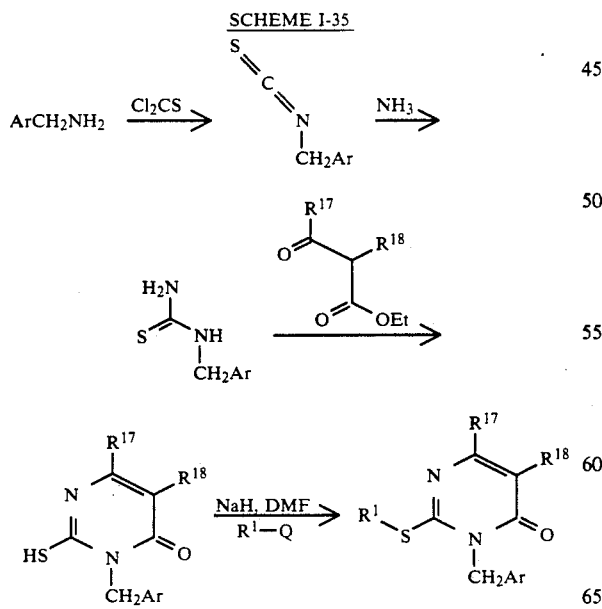

Scheme I-36 provides a method by which the 2-alkoxy-1-alkylpyrimidinones may be synthesized. An appropriately substituted β-keto amide[10] is cyclized with carbonyl diimidazole[11] and converted to the corresponding uracil upon treatment with the appropriately substituted primary amine.[12] The uracil can then be converted to the 2-alkoxy-1-alkylpyrimidinone by treatment with an $R^1$ orthoester.[13] Alternatively, Scheme I-37 shows how the methods of Wittenburg[14] might be employed to accomplish the same transformation.

SCHEME I-36

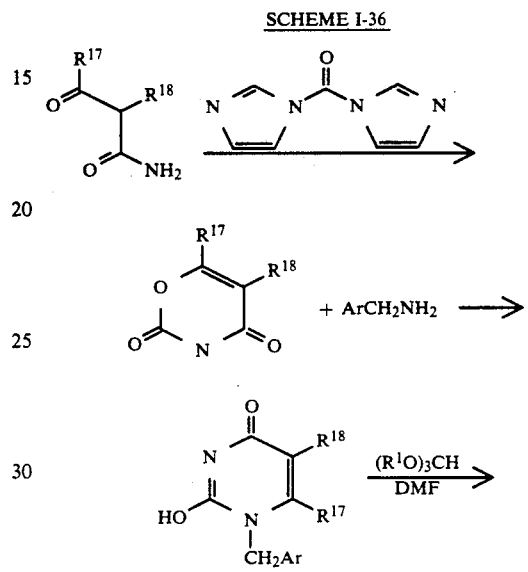

SCHEME I-37

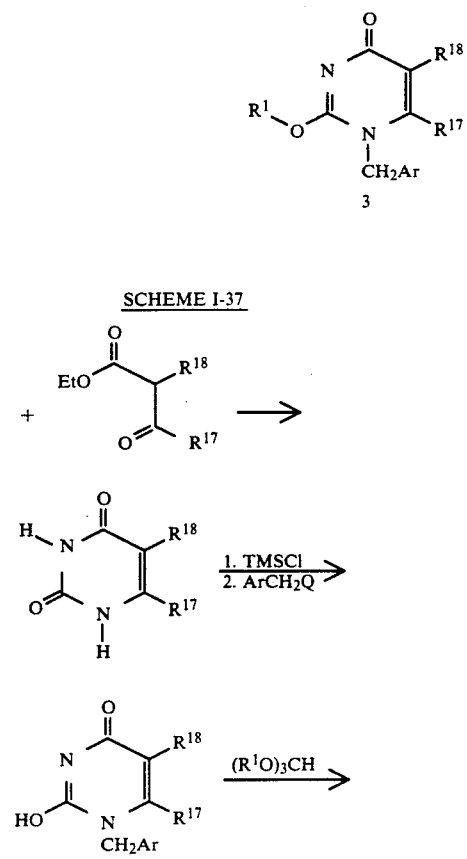

-continued
SCHEME I-37

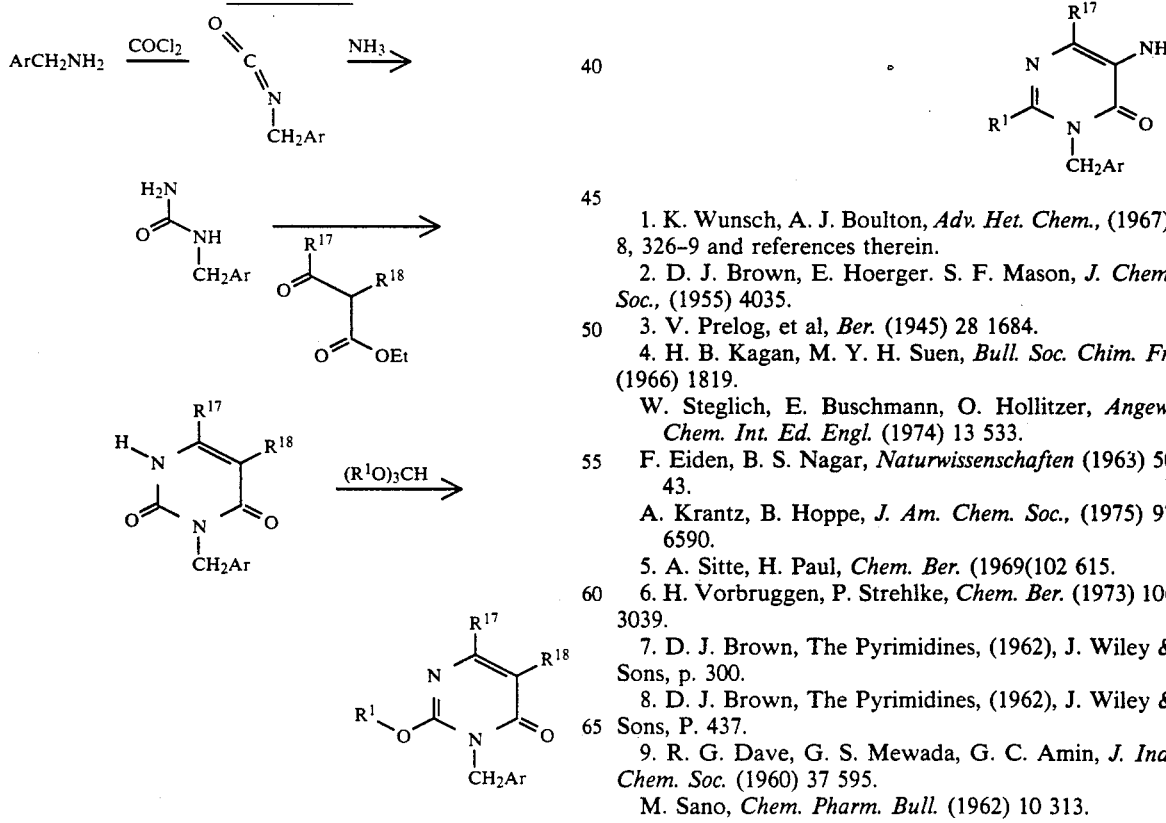

Scheme I-38 shows how the isomeric 2-alkoxy-3-alkylpyrimidinones can be prepared. The primary amine can be converted into an isocyanate[15], then converted to the corresponding urea by treatment with ammonia. Reaction of the urea with an appropriately substituted β-keto ester then gives the 3-substituted uracil.[16] Conversion of the uracil to the corresponding 2-alkoxy pyrimidinone is achieved using an $R^1$ orthoester.[17] Alternatively, a β-aminocrotonate can be reacted with the isocyanate, as shown in Scheme I-39[18], then alkoxylated with an $R^1$ orthoester.

The β-keto esters used in the preceding schemes can be synthesized readily from ethyl hydrogen malonate and an $R^{17}$ acid chloride as shown in Scheme I-40.[19] $R^{17}$ may be alkyl or aryl. Alkylation of this material with an alkyl halide ($R^{18}$-Q) is achieved using sodium hydride in DMSO or by other classical methods. $R^{18}$ may be alkyl or aralkyl suitable protected, if necessary, so as not to react with NaH. Scheme I-41 illustrates the preparation of the 5-alkoxycarbonyl moiety and the corresponding 5-amino derivatives.

SCHEME I-38

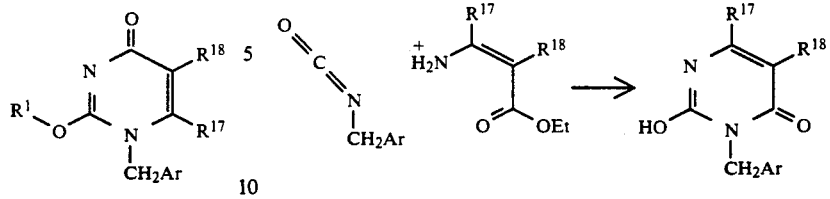

SCHEME I-39

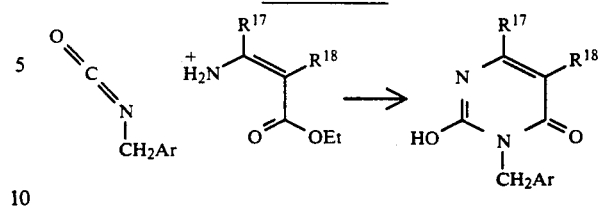

SCHEME I-40

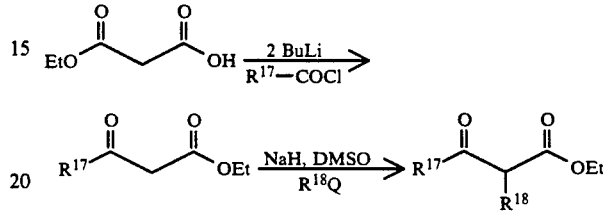

SCHEME I-41

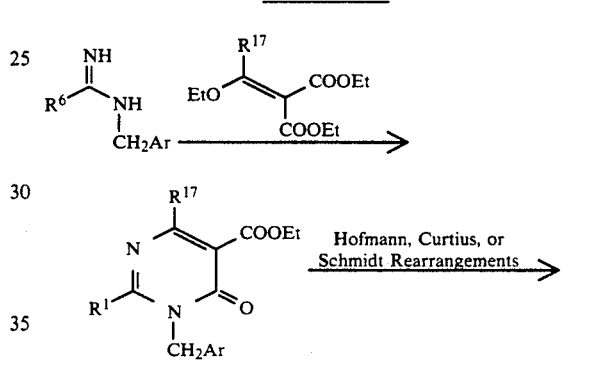

1. K. Wunsch, A. J. Boulton, *Adv. Het. Chem.*, (1967), 8, 326–9 and references therein.
2. D. J. Brown, E. Hoerger. S. F. Mason, *J. Chem. Soc.*, (1955) 4035.
3. V. Prelog, et al, *Ber.* (1945) 28 1684.
4. H. B. Kagan, M. Y. H. Suen, *Bull. Soc. Chim. Fr.* (1966) 1819.
   W. Steglich, E. Buschmann, O. Hollitzer, *Angew, Chem. Int. Ed. Engl.* (1974) 13 533.
   F. Eiden, B. S. Nagar, *Naturwissenschaften* (1963) 50 43.
   A. Krantz, B. Hoppe, *J. Am. Chem. Soc.*, (1975) 97 6590.
5. A. Sitte, H. Paul, *Chem. Ber.* (1969(102 615.
6. H. Vorbruggen, P. Strehlke, *Chem. Ber.* (1973) 106 3039.
7. D. J. Brown, The Pyrimidines, (1962), J. Wiley & Sons, p. 300.
8. D. J. Brown, The Pyrimidines, (1962), J. Wiley & Sons, P. 437.
9. R. G. Dave, G. S. Mewada, G. C. Amin, *J. Ind. Chem. Soc.* (1960) 37 595.
   M. Sano, *Chem. Pharm. Bull.* (1962) 10 313.

C. Piantadosi, V. G. Skulason, J. L. Irvin, J. M. Powell, L. Hall, *J. Med. Chem.* (1964) 7 337.

10. M. K. Jain, *Ind. J. Chem.* (1963) 1 274. P. C. Kuzma, L. E. Brown, T. M. Harris, *J. Org. Chem.* (1984) 49 2015.

11. S. De Bernardo, M. Weigele, *J. Org. Chem.* (1977) 42 109.

12. T. Kinoshita, H. Tanaka, S. Furukawa, *Chem. Pharm. Bull.* (1986) 34 1809.

13. F. Yoneda, T. Nagamatsu, M. Takamotor, *Chem. Pharm. Bull.* (1983) 31 344.

14. Wittenburg, *Angew, Chem.* (1965) 77 1043.

15. S. Osaki, *Chem. Rev.* (1972) 72 457.

16. Gabriel, Colman, *Ber.* (1904) 37 3657.

17. F. Yoneda, T. Nagamatsu, M. Takamoto, *Chem, Pharm. Bull.* (1983) 31 344.

18. R. Behrend, F. C. Meyer, Y. Buckholz, *Liebigs Ann. Chem.* (1901) 314 200.

19. W. Wierenga, H. I. Skulnick, *Org. Syn,* (91983) 61, 5.

PART II: Preparation of substituted methylphenylthiophenes and furan derivatives and alkylation with the heterocycles described in Part I.

The desired bromomethylphenyl thiophene necessary for the construction of 3,4-disubstituted thiophenes of formula I, where $X^1-X^2-X^3-X^4=-CH-S-CH-CZ-$ and Z=tetrazolyl are prepared as illustrated in scheme II-1. Palladium (0) catalyzed coupling of p-tolyltrimethyltin with 3,4-dibromothiophene in refluxing toluene or DMF at 70°-80° C. for 12 to 24 hours provides 3-bromo-4-tolylthiophene. This bromide could be displaced with cyanide using copper (I) cyanide in hot quinoline. The nitrile is converted to the trityl protected tetrazole in a three step procedure using trimethyltin azide in refluxing toluene followed by treatment with acid and finally protection with triphenylmethyl chloride in the presence of triethyl amine using $CH_2Cl_2$ or $CHCl_3$ as solvent. The protected tetrazole compound can be treated with N-bromosuccinimidein refluxing carbontetrachloride in the presence of a catalytic amount of AIBN or benzoylperoxide to provide the necessary bromoethylphenyl thiophenes. Substitution in the 2-position of the thiophene ring can be accomplished by reaction with nBuLi or tBuLi followed by quenching with an appropriate electrophile. Again reaction with N-bromosuccinamide, as before, provides the required bromomethylphenyl thiophenes.

SCHEME II-1

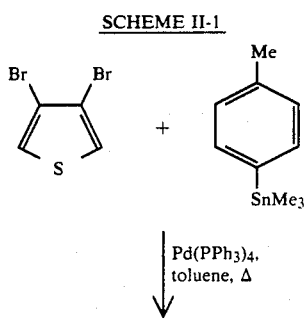

-continued
SCHEME II-1

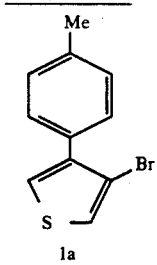
1a

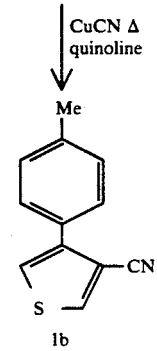
1b

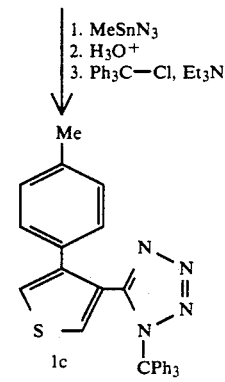
1c

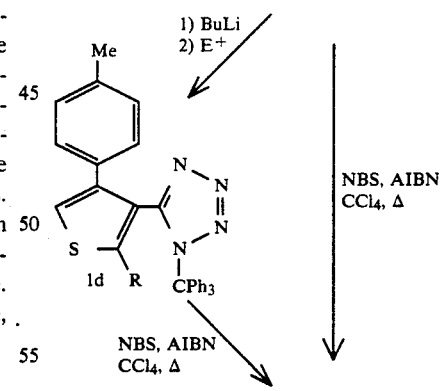
1d

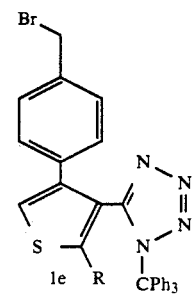
1e

The desired bromomethylphenyl thiophene necessary for the construction of 3,4-disubstituted thiophenes of Formula I, where $X^1-X^2-X^3-X^4=$ —CH—S—CH—CZ— and $Z=SO_2NHCOR^7$, are prepared as illustrated in scheme II-2. Sequential dianion formation of 2a with nBuII or tBuLi in THF at −20° C., followed by quenching with TMSCl provides 2. Treatment with strong base such as nBuLi, LDA or tBuLi, followed by quenching with $Br_2$ affords the bromo thiophene derivative 2c. Palladium catalyzed cross-coupling of 2c with p-tolyltrimethyltin using $PdCl_2(PPh_3)_2$ in hot DMF or $Pd(PPh_3)_3$ in hot toluene provides 2d. Biaryl compound 2d can be treated with N-bromosuccinimide in refluxing carbontetrachloride or benzene in the presence of a catalytic amount of AIBN or benzoylperoxide to provide the necessary bromomethylphenyl thiophenes.

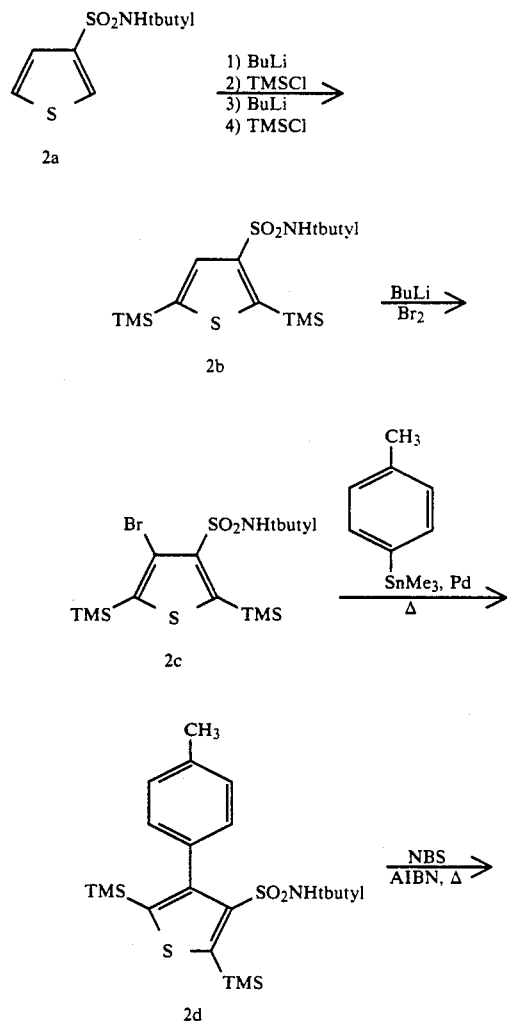

SCHEME II-2

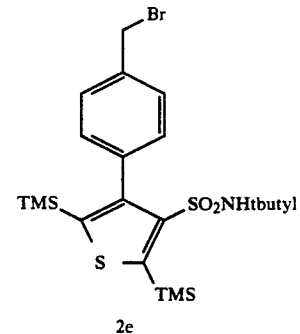

The desired methanesulfonylmethylphenyl thiophenes and furans necessary for the construction of 2,3-disubstituted thiophenes and furans (Y=O or S) of formula I, where $X^1-X^2-X^3-X^4=$ —CH—CH—S—CZ— and Z=tetrazolyl, are prepared as illustrated in scheme II-3. 2-Cyanothiophene and 2-cyanofuran are converted to their respective protected tetrazoles by reaction with trimethyltin azide in refluxing toluene followed by treatment with dilute mineral acid and finally protection with triphenylmethyl chloride in the presence of triethyl amine in a chlorinated solvent. Reaction of the heterocycle with a strong base such as nBuLi followed by quenching with trimethylsilyl chloride fixes a trimethyl silyl group in the 5-position. Again reaction with a strong base (tBuLi, nBuLi or LDA), this time, followed by quenching with trimethyltin chloride provides the protected tetrazolylaryltrimethyltin derivative. Palladium catalyzed cross coupling with methyl p-iodobenzoate in refluxing toluene or hot MDF for several hours is followed by lithium aluminum hydride reduction and conversion of the subsequent alcohol to the mesylate with methanesfulonyl chloride and treithyl amine.

SCHEME II-3

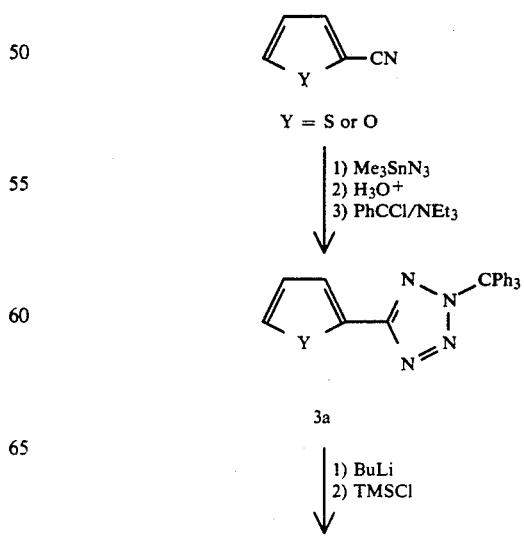

-continued
SCHEME II-3

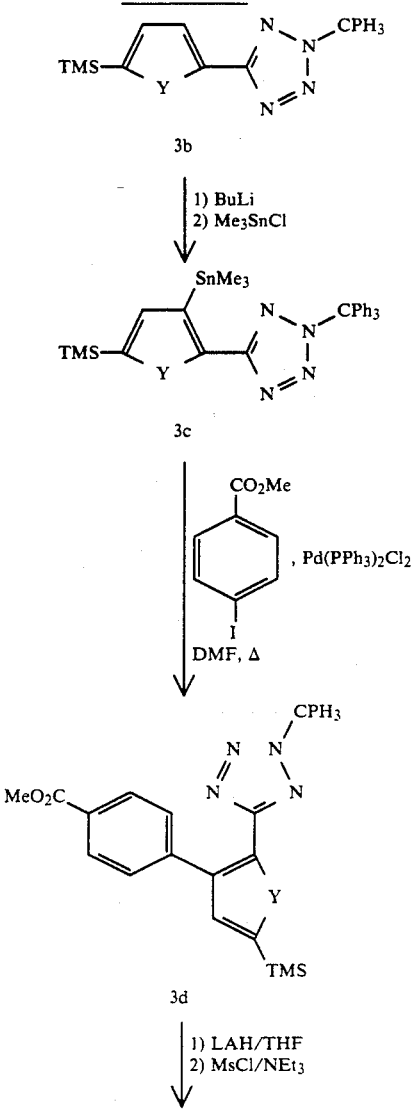

-continued
SCHEME II-3

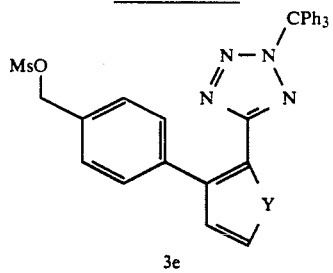

The desired bromomethylphenyl thiophenes and furans necessary for the construction of 2,3-disubstituted thiophenes and furans (Y=O or S) of formula I, where $X^1-Z^2-X^3-X^4=-CR^{12}-S-CZ-$ and $Z=SO_2NHCOR^7$ and $R^{11}=R^{12}=H$, are prepared as illustrated in scheme II-4. Palladium(O) catalyzed coupling of p-tolyltrimethyltin with a 3-bromothiophene or furan derivative in refluxing toluene provides the 3-tolylthiophene or 3-bromothiophene or furan. If the 5-position of the furan or thiophene is unsubstituted it is protected as was carried out in scheme II-3 with a trimethylsilyl group. Reaction with a strong base such as nBuLi, generating the anion at the 2-position, is followed by successive quenching with $SO_2(g)$ followed by N-chlorosuccinamide. The resultant sulfonyl chloride is reacted with tbutyl amine in $CH_2Cl_2$ and is followed by benzylic bromination with N-bromosuccinimide utilizing AIBN or benzoylperoxide as a radical intiator to afford the desired bromomethylphenyl thiophenes and bromomethylphenyl furans.

SCHEME II-4

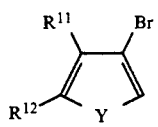

Y = S or O

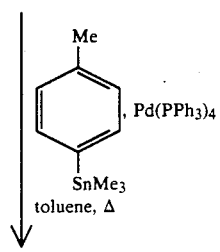

toluene, Δ

SCHEME II-4

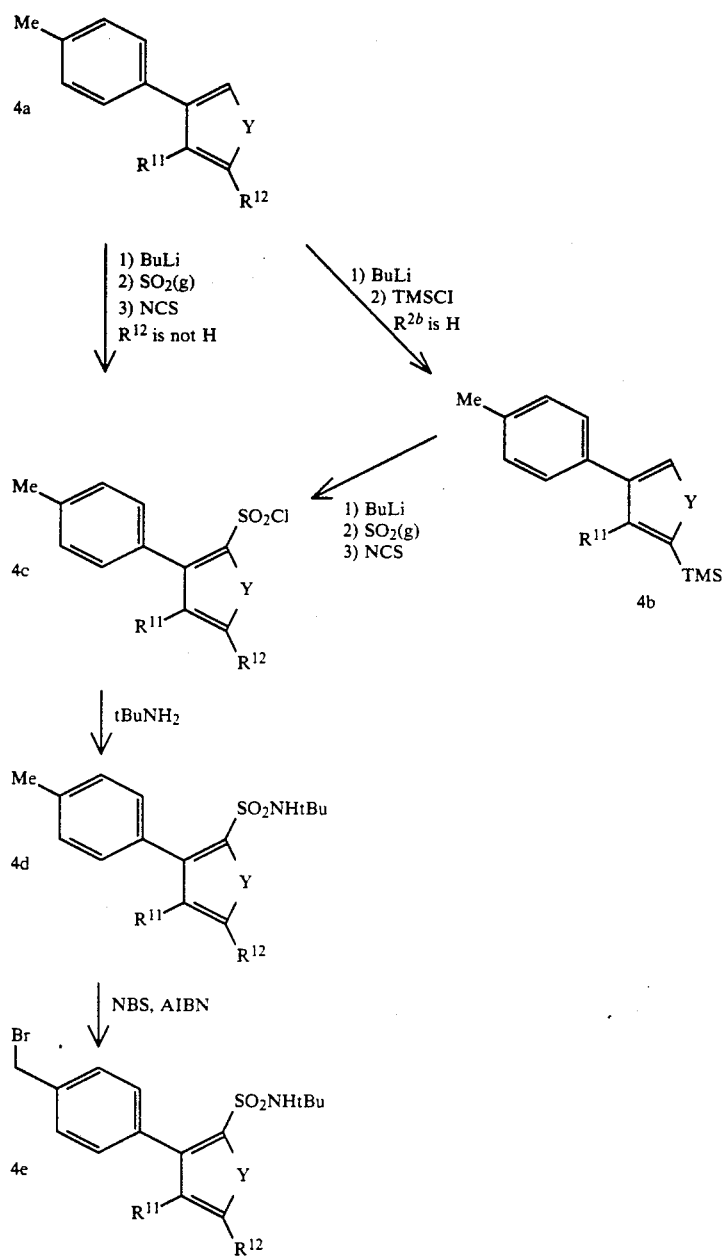

An alternative synthesis for the desired 3-(4-bromomethylphenyl) thiophenes and furans necessary for the constuction of 2,3-disubstituted thiophenes and furans of the 2,3-disubstituted thiophenes and furans (Y=O or S) of formula I, where $X^1$—$X^2$—$X^3$—$X^4$=—$CR^{11}$—$CR^{12}$—S—CZ— and Z=$SO_2NHCOR^7$ and $R^{11}$=$R^{12}$=H, is illustrated in scheme II-5, 2-Thiophenesulfonyl chloride and 2-furansulfonyl chloride are converted to their respective tbutyl sulfonamides by reaction with tbutylamine in $CH_2Cl_2$. The dianion is generated with two equivalents of a strong base such as nBuLi or tBuLi; this is followed by quenching with TMSCl, addition of another equivalent of strong base and finally quenching with $Br_2$. These bromo derivatives are coupled with p-tolyltrimethyl tin in the presence of a catalytic amount of palladium (0) in refluxing toluene or hot DMF. Benzylic bromination using N-bromosuccinimide provides the desired bromomethylphenyl thiophenes and bromomethylphenyl furans.

SCHEME II-5

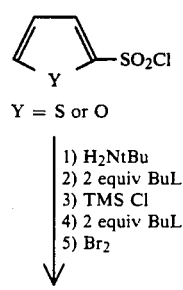

Y = S or O

1) $H_2NtBu$
2) 2 equiv BuLi
3) TMS Cl
4) 2 equiv BuLi
5) $Br_2$

↓

-continued
SCHEME II-5

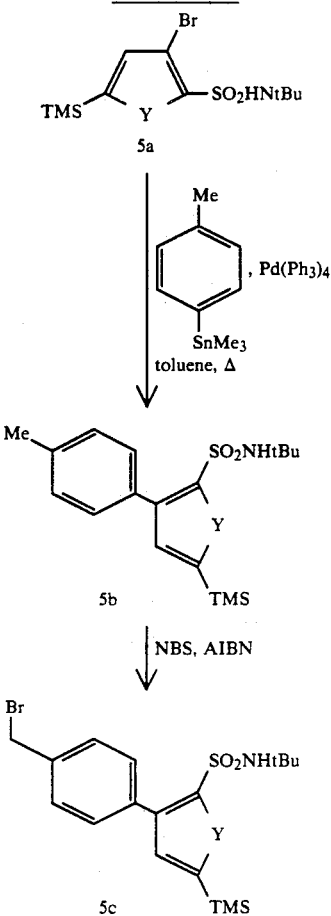

The desired methanesulfonylmethylphenyl thiophenes and furans necessary for the constuction of 2,3-disubstituted thiophenes and furans (Y=O or S) of formula I, where $X^1-X^2-X^3-X^4=-S-CH=CH-CZ-$ and Z=tetrazolyl, are prepared as illustrated in scheme II-6. 3-Cyanothiophene and 3-cyanofuran are converted to their respective protected tetrazole derivatives by reaction with trimethyltin azide in refluxing toluene followed by treatment with dilute mineral acid and finally protection with triphenylmethyl chloride in the presence of triethyl amine. Generation of the anion at the 2-position, using a strong base such as nBuLi, followed by quenching with trimethyltin chloride provides the desired protected tetrazolylaryltrimethyltin derivative. Palladium catalyzed cross coupling with methyl p-iodobenzoate using Pd(PPH$_3$)$_2$Cl$_2$ or Pd(PPh$_3$)$_4$ in refluxing toluene or hot DMF followed by lithium aluminum hydride reduction and treatment of the resultant alcohol with methanesulfonyl chloride and triethyl amine provides the desired methanesulfonylmethylphenyl thiophenes and methanesulfonylmethylphenyl furans.

SCHEME II-6

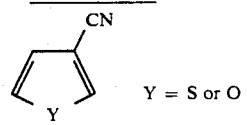
Y = S or O

-continued
SCHEME II-6

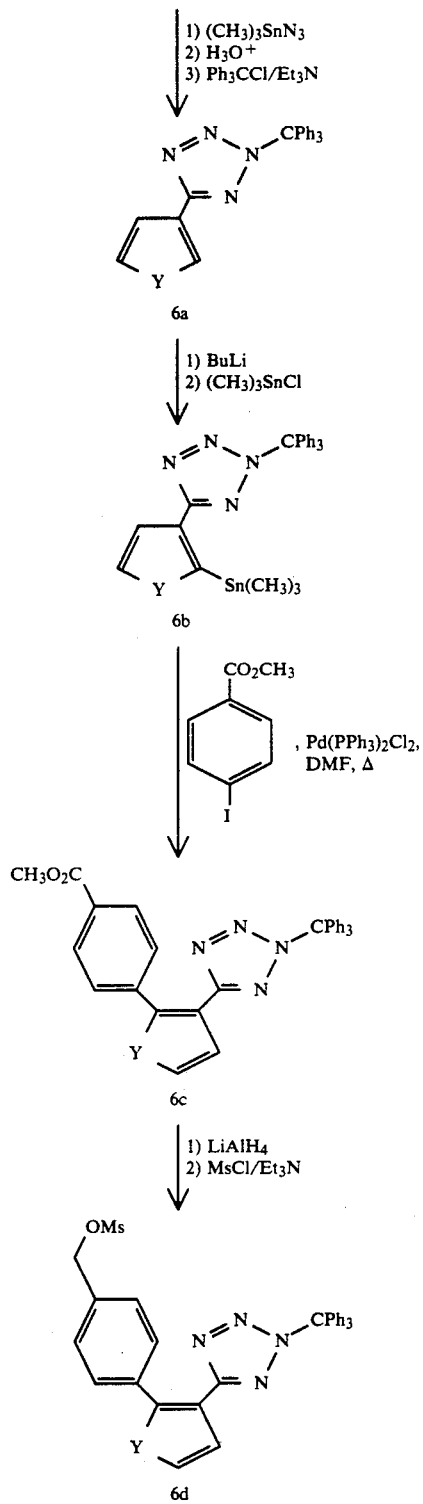

The desired bromomethylphenyl thiophenes and furans necessary for the construction of 2,3-disubstituted thiophenes and furans (Y=O or S) or formula I, where $X^1-X^2-X^3-X^4=-S-CH=CH-CZ-$ and $Z=SO_2NHCOR^7$, are prepared are illustrated in scheme II-7. 2,5-Dibromothiophene or 2,5-dibromofuran can be chlorosulfonylated with chlorosulfonic acid to provide sulfonyl chloride 7a. Reaction with tbutylamine, followed by reduction with zinc in acetic acid affords 7c. Dianion generation, using a strong base (nBuLi or tBuLi), followed by quenching with $Br_2$, provides bromo compound 7d. Palladium catalyzed coupling of p-tolytrimethyltin with the newly prepared arylbromide in hot DMF or refluxing toluene provides biaryl compound 7e. Treatment of 7e with N-bromosuccinimide in the presence of a catalytic amount of AIBN or benzoylperoxide in refluxing carbontetrachloride or benzene provides the desired bromomethylphenyl thiophenes and bromomethylphenyl furans.

SCHEME II-7

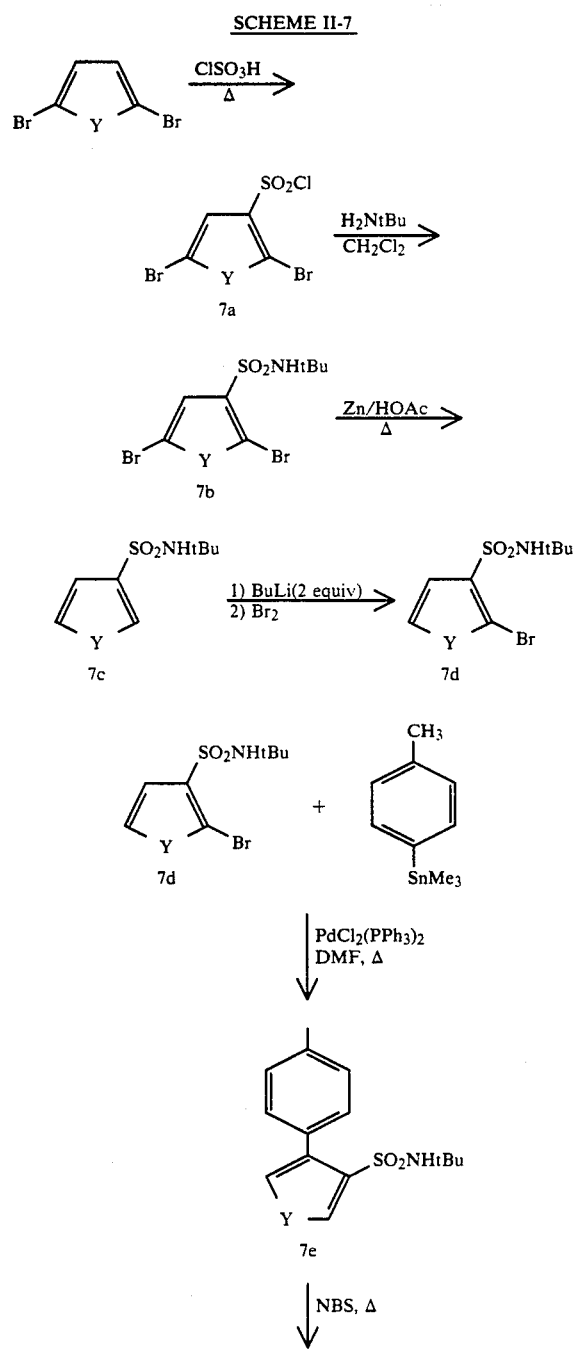

-continued
SCHEME II-7

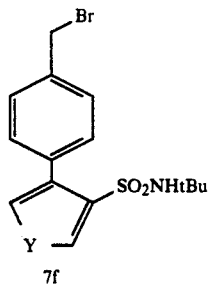

The desired antagonists of formula I (Z=tetrazolyl) are prepared, as illustrated in scheme II-8, by deprotonation of the desired heterocycle, for example 2-butyl-6-methylquinazolin-4(1H)-one, with sodium hydride in dimethylformamide to generate the sodium salt, 8a. Alkylation of the sodium salt with a derivative containing a good leaving group such as the bromomethyl derivative or the methanesulfonyl derivative, is followed by deprotection to provide the free tetrazole.

The desired antagonists of formula I (Z=$SO_2$NHCOR$^7$) are prepared, as illustrated in scheme II-9, by deprotonation of the desired heterocycle, for example 2-butyl-6-methylquinazolin-4-(1H)-one, with sodium hydride in dimethylformamide to generate the sodium salt. Alkylation of the sodium salt with the bromomethyl derivative or the methanesulfonyl derivative followed by deprotection with trifluoroacetic acid and coupling with an activated acid derivative completes the synthesis of the sulfonamide containing thiophene antagonists.

The desired antagonist of formula I, where $X^1$—$X^2$—$X^3$—$X^4$=—$CR^{11}$—$CR^{12}$—S—CZ—, Z=$SO_2$HNCOR$^7$, $R^{11}$ and $R^{12}$ are joined to form an aryl ring, and $R^7$=Ph, is prepared as illustrated in scheme II-10 by deprotonation of the desired heterocycle, for example 2-butyl-6-methylquinazolin-4(1H)-one, with sodium hydride in dimethyl formamide to generate the sodium salt. Alkylation of the sodium salt with the benzothiophene derivative, compound 4e, which is prepared using the chemistry illustrated in scheme II-4, affords 10a. As in scheme II-9, deprotection with TFA is followed by coupling to an activated acid derivative to complete the synthesis.

SCHEME II-8

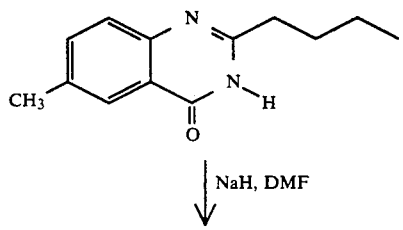

| NaH, DMF

SCHEME II-8
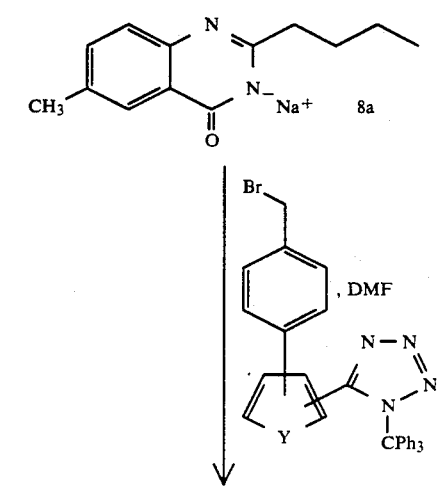
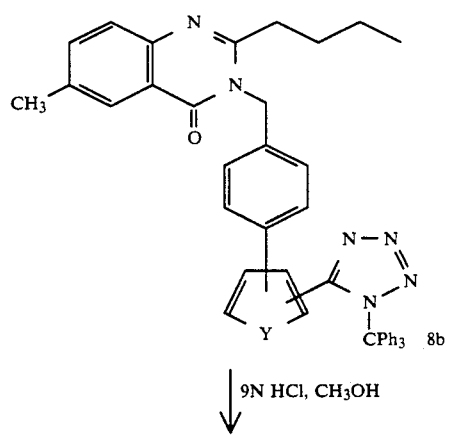
9N HCl, CH₃OH
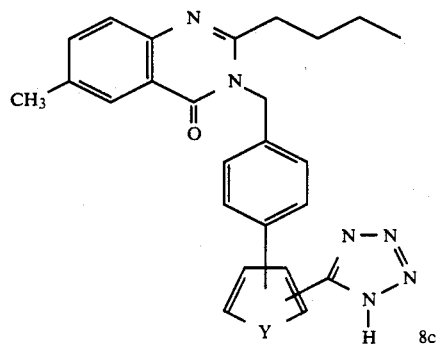
SCHEME II-9
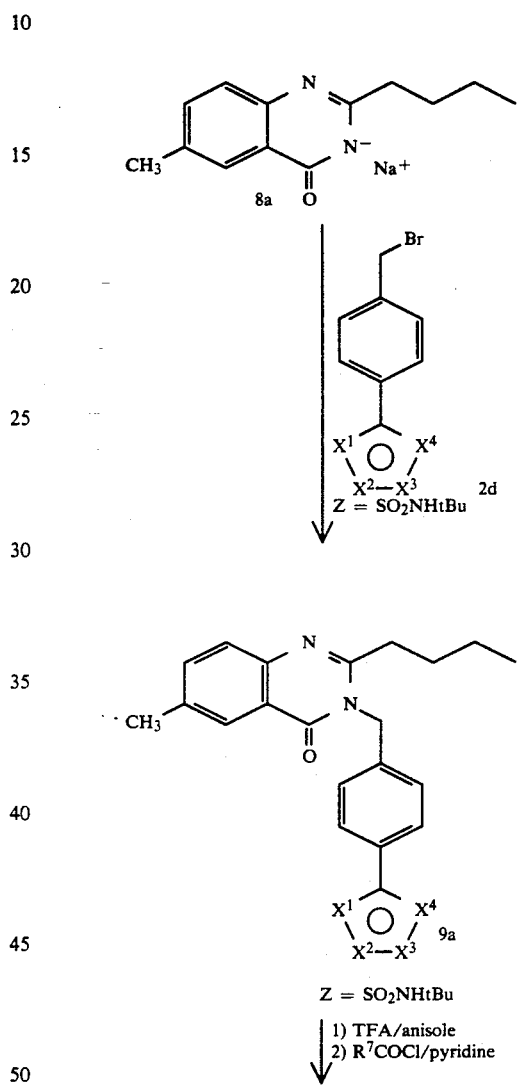
1) TFA/anisole
2) R⁷COCl/pyridine
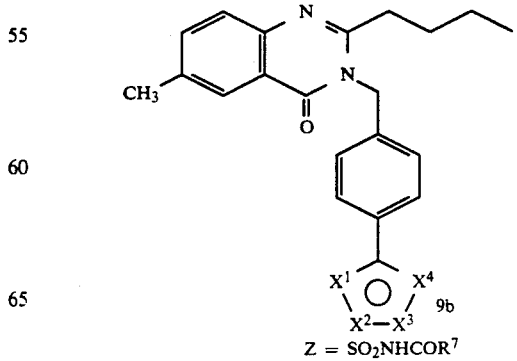

SCHEME II-10

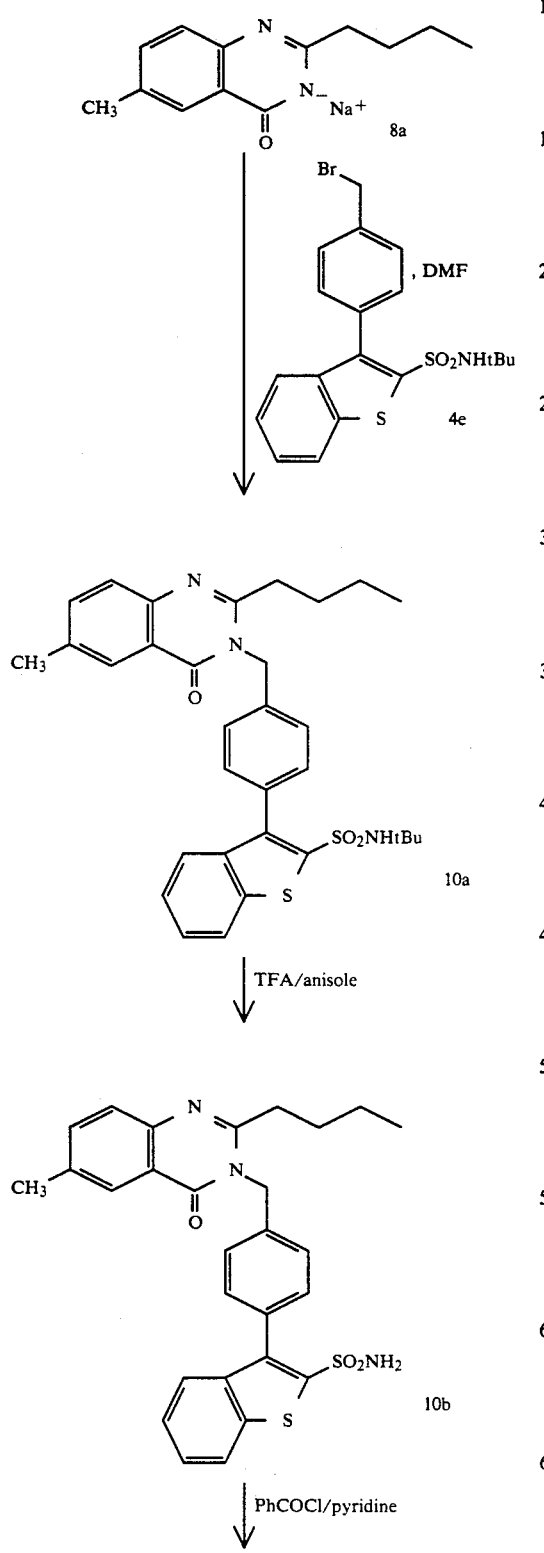

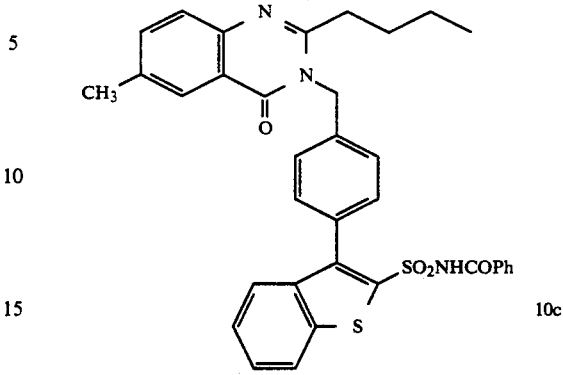

An alternative synthesis for the bromomethylphenyl thiophenes necessary for the construction of substituted thiophenes of formula I, where $X^1\text{---}X^2\text{---}X^3\text{---}X^4\text{=}\text{---}CH\text{=}C(R^{12})\text{---}S\text{---}CZ\text{=}$ and $Z\text{=}SO_2NHCOR^{14}$ is illustrated in scheme II-11. Alkylthiophene 11a is cleanly prepared by alkylation of the dianion of 2-(tbutylsulfonamido)thiophene, generated with two equivalents of BuLi or LDA, with an appropriate alkylhalide ($R^{12}X$). A second dianion generation, followed by quenching first with triisopropylborate, then with 2N HCl, affords the boronic acid derivative 11b. Palladium catalyzed coupling of the 11b with 4-bromobenzyl alcohol provides 11c. The benzyl alcohol is then cleanly converted to the corresponding bromide (11d) with $PB_3$ or $CBr_4/PPh_3$.

This benzyl bromide is used in place of compound 2d in scheme II-9 to complete the synthesis of the antagonist.

Scheme II-12 illustrates a more convergent approach to the synthesis of substituted thiophenes of formula I, where $X^1\text{---}X^2\text{---}X^3\text{---}X^4\text{=}\text{---}CH\text{=}C(R^{12})\text{---}S\text{---}CZ\text{-}$ $=$ and $Z\text{=}SO_2HNCOR^{14}$. Palladium catalyzed coupling of boronic acid 11b with a 4-bromobenzyl derivative, such as 12a, provides a nearly complete antagonist. Completion of the antagonist from 12b is illustrated in scheme II-9.

SCHEME II-11

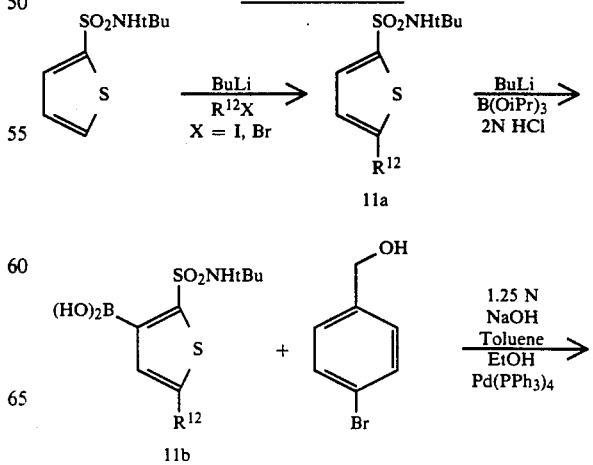

-continued
SCHEME II-11

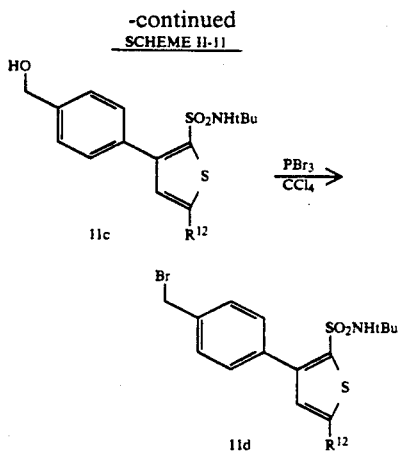

SCHEME II-12

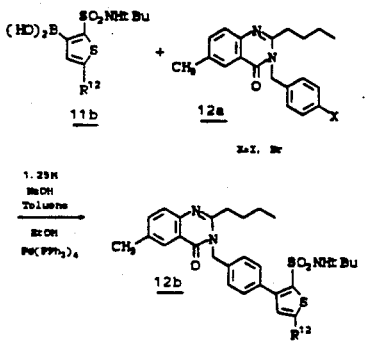

An alternative synthesis for the bromomethylphenyl thiophenes necessary for the construction of substituted thiophenes of formula I, where $X^1-X^2-X^3-X^4=-CH=C(R^{12})-S-CZ=$ and Z=tetrazolyl is illustrated in scheme II-13. alkylthiophene 13a is prepared by alkylation of the 2-(triphenylmentyltetrazolyl)-thiophene with an appropriate alkylhalide ($R^{12}X$). Directed metallation with BuLi, is followed by quenching with triisopropylborate. The borate ester is gently hydrolyzed with dilute acetic acid to afford the boronic acid derivative 13b. Palladium catalyzed coupling of 13b with 4-bromobenzyl alcohol provides 13c. The benzyl alcohol is then cleanly converted to the corresponding bromide (13d) with $PBr_2$ or $CBr_4/PPh_3$.

This benzyl bromide is used in place of compound 2d in scheme II-9 to complete the synthesis of the antagonist.

Scheme II-14 illustrates a more convergent approach to the synthesis of substituted thiophenes of formula I, where $X^1-X^2-X^3-X^4=-CH=C(R^{12})-S-CZ=$ and Z=tetrazolyl. Palladium catalyzed coupling of boronic acid 13b with a 4-bromobenzyl derivative, such as 12a, provides a nearly complete antagonist. Completion of the antagonist from 14b is illustrated in scheme II-9.

-continued
SCHEME II-13

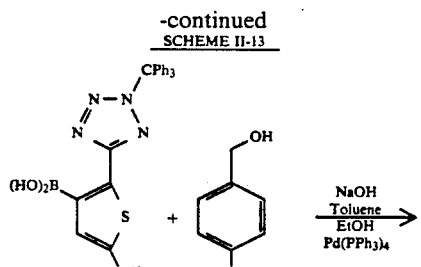

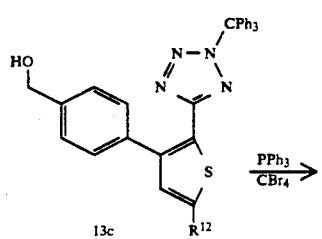

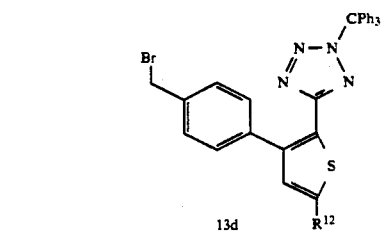

SCHEME II-14

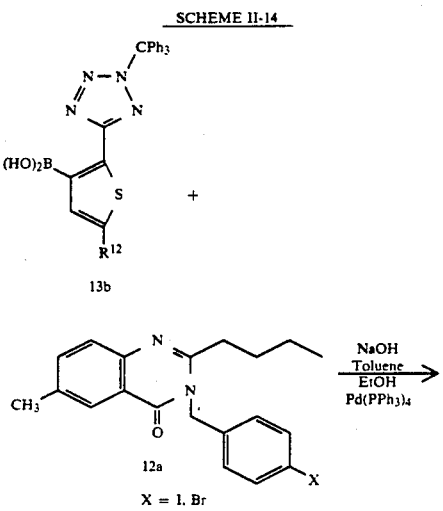

-continued
SCHEME II-14

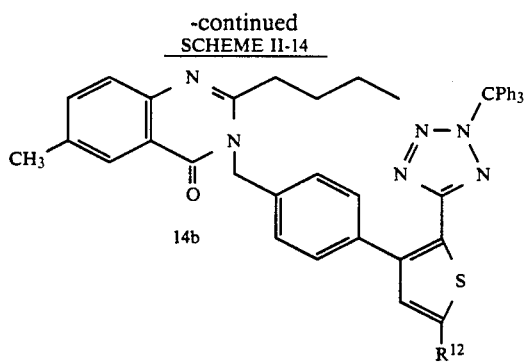

Compounds of formula I, where $X^1—X^2—X^3—X^4=$ —CH=C($R^{12}$)—S—CZ=, Z=$SO_2NHCOR^{14}$ and $R^{12}$=$CH_2NR^{2a}R^{2a}$ best prepared as illustrated in scheme II-15. Palladium catalyzed coupling of boronic acid 11b ($R^{12}$=TMS) with 4-bromotoluene provides 15a. Fluoride mediated removal of the trimethylsilyl group is cleanly accomplished using $nBu_4F$ in THF. Dianion formation of 15b followed by quenching with a formylating agent, such as DMF, provides the formyl derivative after acid work-up. Benzylic bromination is followed by coupling to the sodium salt of a heterocycle such as a substituted quinazolinone, triazolinone or pyrimidinone to afford 15e. Reductive amination of the aldehyde is then followed by the usual reactions to complete the synthesis of the antagonist.

Alternatively, bromomethyl derivative 16e (scheme II-16) can be prepared and coupled to a heterocycle using previously described synthetic methods. NBS bromination of 2-methyl-5-(tbutylsulfonamido)thiophene provides bromomethyl derivative 16a. The bromomethyl derivative is then reacted with excess amine (HNR$^{2a}$R$^{2a}$), such as morpholine, to afford 16b. Reaction of 16b with two equivalents of a strong base, such as LDA or nBuLi, is followed by addition of bromine to provide 16c. Palladium catalyzed coupling of 16c with 4-(t-butyldimethylsilyloxymethyl)-phenyltrimethyltin provides compound 16d. Silyl removal followed by conversion to the corresponding bromide affords 16e.

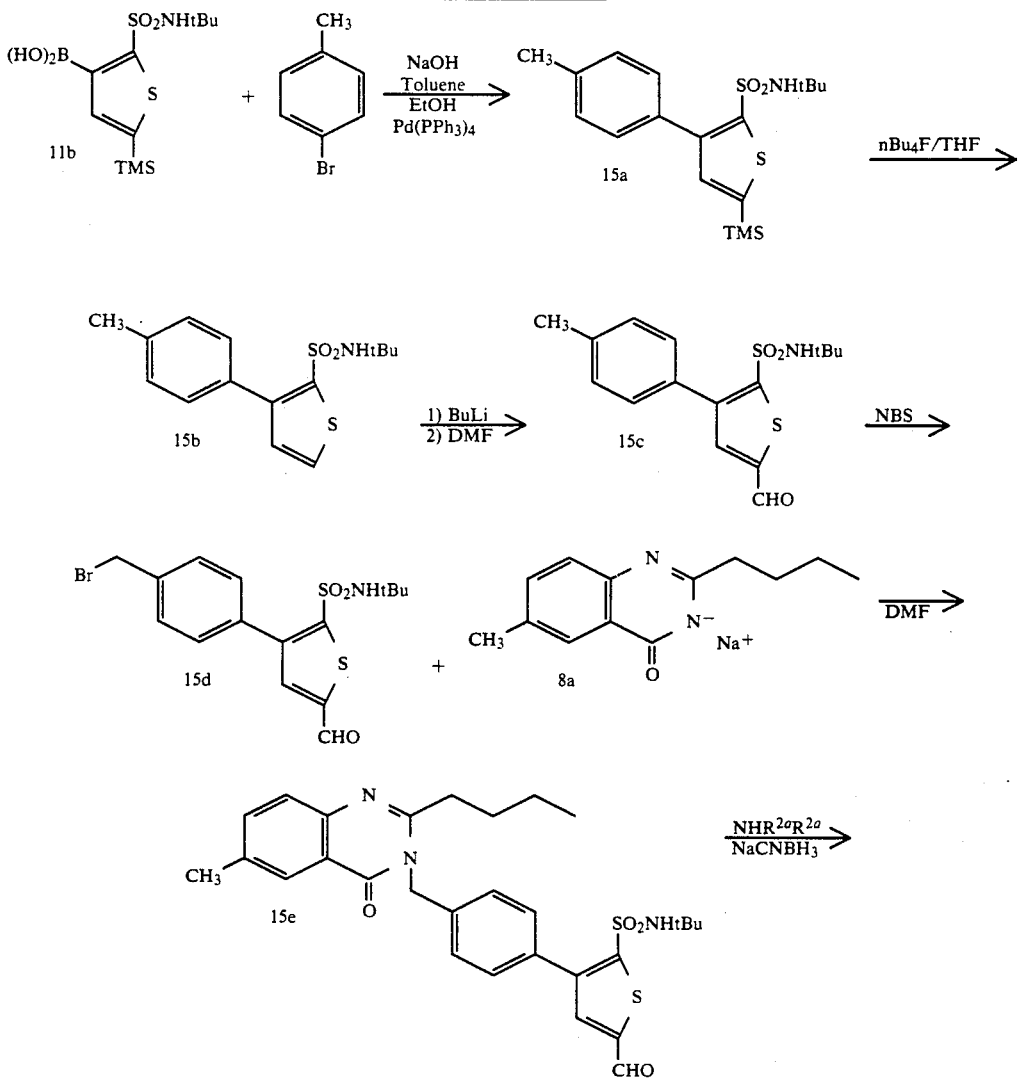

SCHEME II-15
-continued

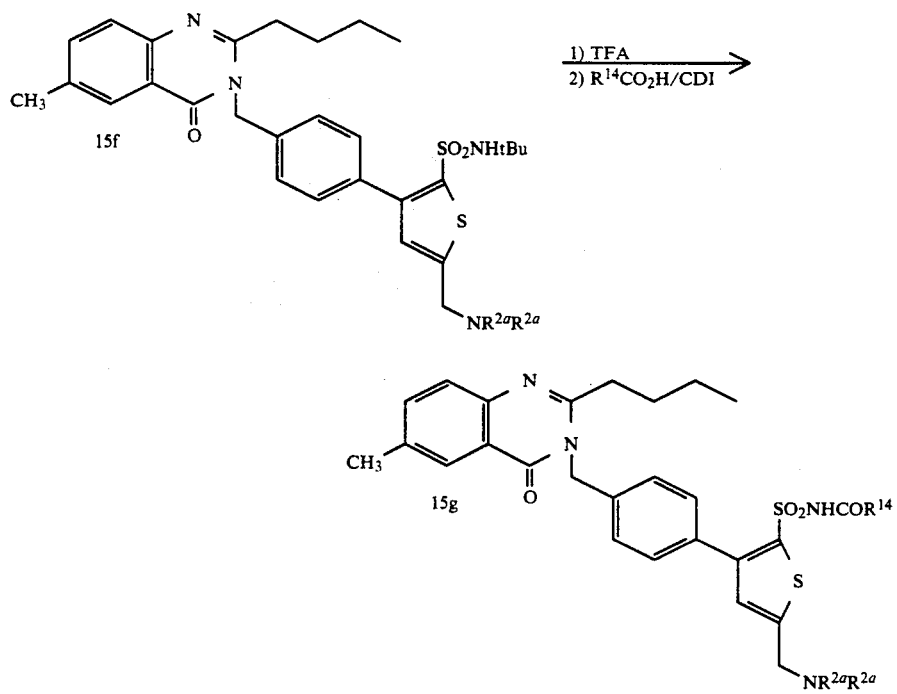

SCHEME II-16

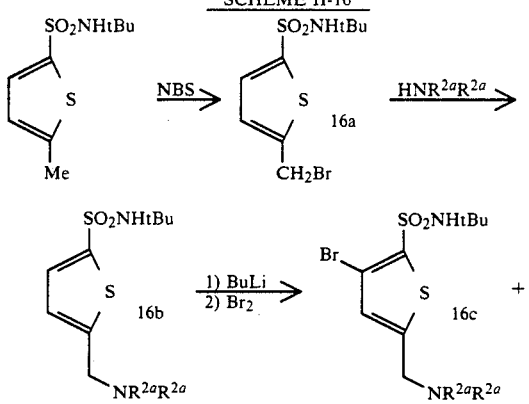

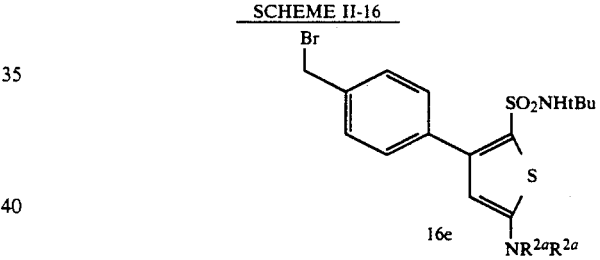

-continued
SCHEME II-16

Antagonists of formula I, where the heterocycle is a 2-alkyl-8-nitrogen substituted quinazoline-4(1H)-one, $X^1$—$X^2$—$X^3$—$X^4$ is —CH=CR$^{12}$—S—CZ=, and Z=SO$_2$NHCOR$^{14}$ are best prepared by the synthetic route outline in Scheme II-17. Hydrogenation of the 6-nitroquinazolinone cleanly produces the desired amino derivative. Acylation with an appropriate acid chloride in the presence of pyridine provided derivative 17c. Coupling of 17c with lid in DMF using K$_2$CO$_3$ affords the coupled product 17d. Deprotection with TFA is followed by acylation, with either and acid chloride (R$^{14}$COCl) in the presence of pyridine or an acid (R$^{14}$CO$_2$H) after prior activation with CDI, to complete the antagonist.

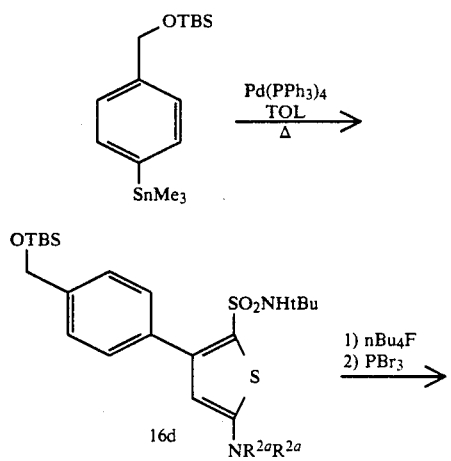

SCHEME II-17

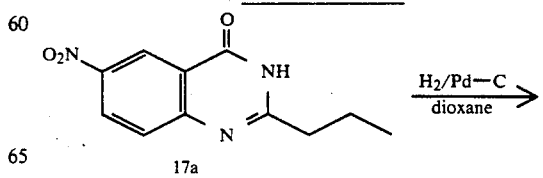

79
-continued
SCHEME II-17

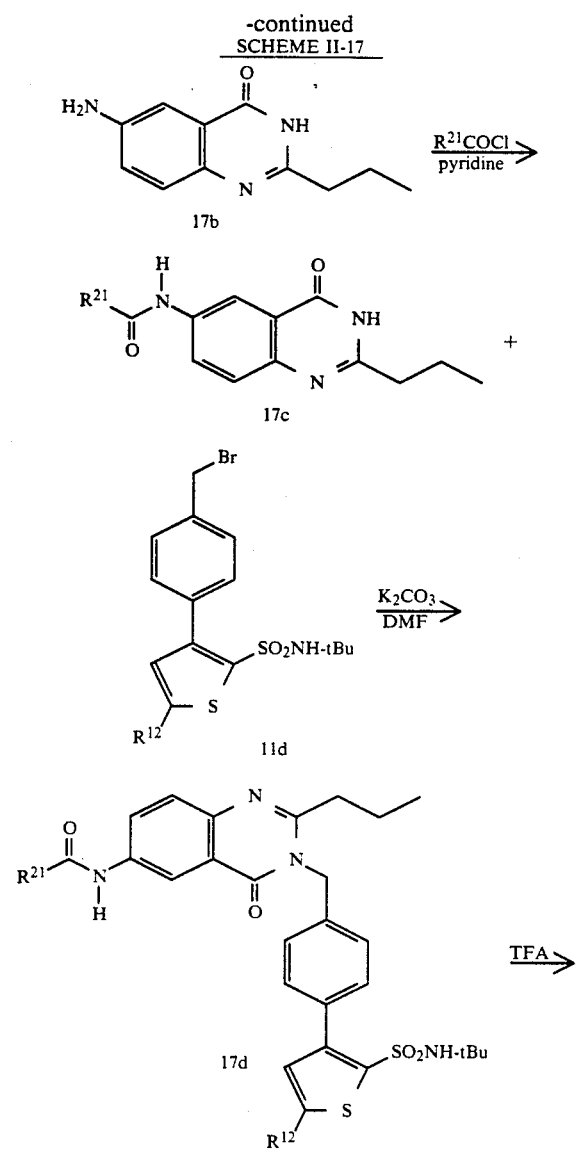

80
-continued
SCHEME II-17

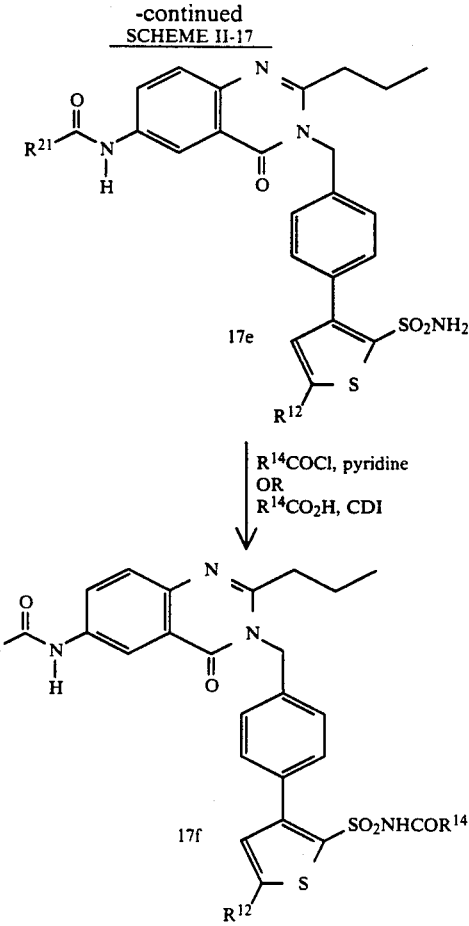

In some instances functionalization of the quinazolinone is best performed after coupling with the bromomethylphenylthiophene derivative (11d). This is most efficiently accomplished using the synthetic route outlined in Scheme II-18. Alkylation of 2-propyl-6-nitroquinazolinone with benzylbromide derivative 11d using $K_2CO_3$ in DMF provides 18a. Deprotection with TFA and hydrogenation provides the amino sulfonamide derivative 18b. The amine function can be reacted with a variety of electrophiles, such as an isocyanate, to afford, in this case, the urea derivative 18c. Acylation of the sulfonamide, using procedures previously described, completes the synthesis of the antagonist.

SCHEME II-18

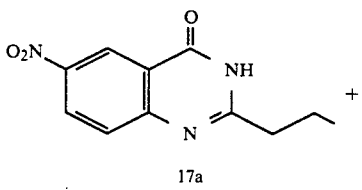

5,252,574
-continued
SCHEME II-18
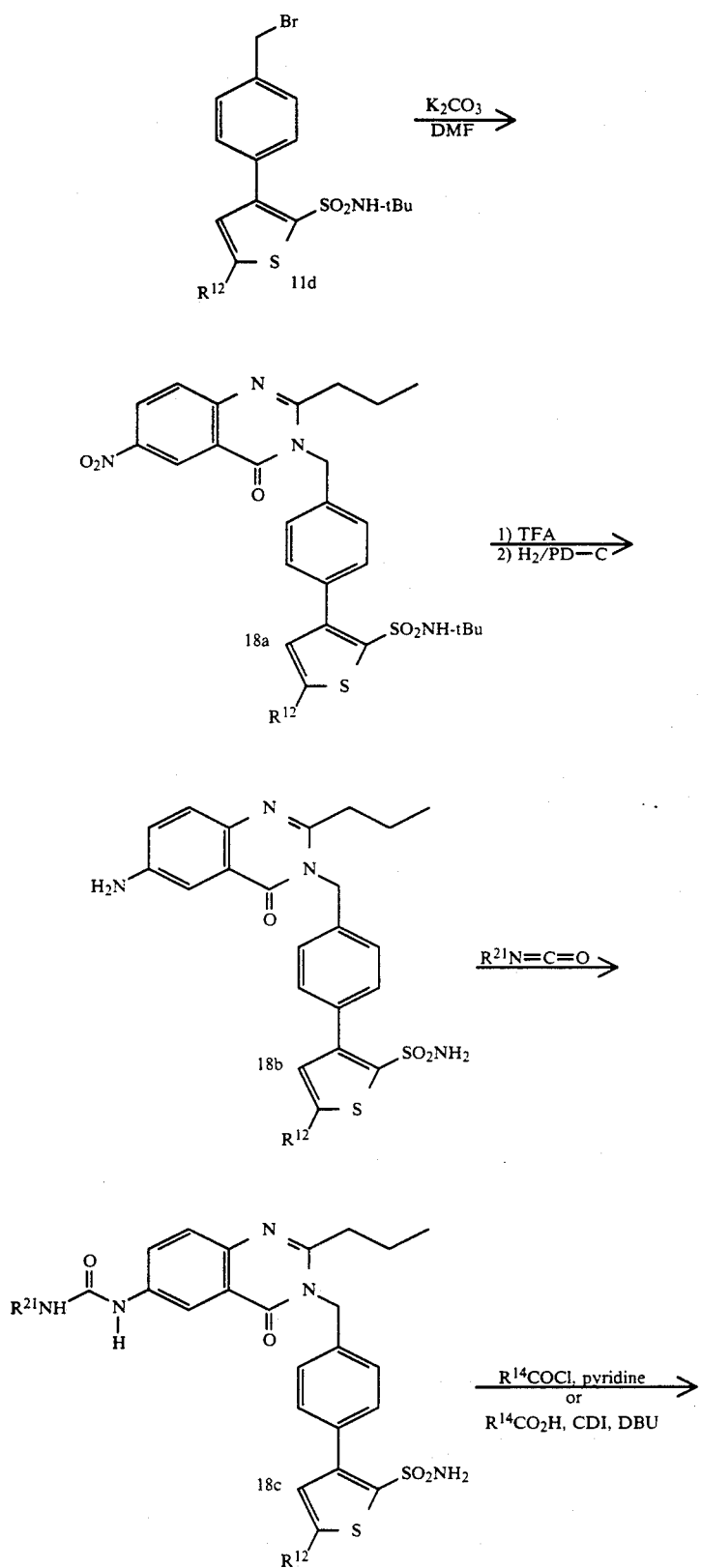

SCHEME II-18

-continued

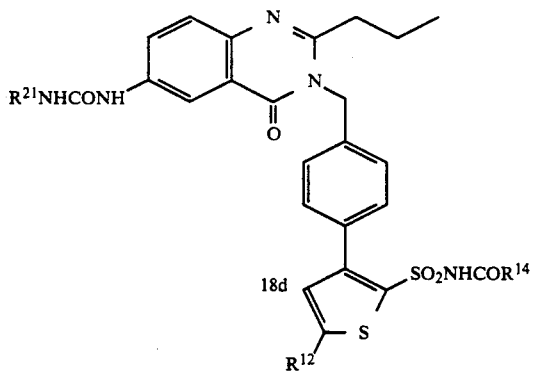

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 mL) homogenized, and then centifuged. The mixture was filtered through a cheesecloth and the supernatant was centrifuged for 30 minutes at 20,000 rpm at 4° C. The pellet thus obtained was resuspended in 30 mL of 50 mM Tris-5 mM $MgCl_2$ buffer containing 0.2% Bovine Serum Albumin and 0.2 mg/mL Bacitracin and the suspension was used for 100 assay tubes. Samples tested for screening were done in duplicate. To the membrane preparation (0.25 mL) there was added $^{125}$I-Sar$^1$Ile$^1$-angiotensin II [obtained from New England Nuclear] (10 mL; 20,000 cpm) with or without the test sample and the mixture was incubated at 37° C. for 90 minutes. The mixture was then diluted with ice-cold 50 mM Tris-0.9% NaCl, pH 7.4 (4mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris HCl (50 mM), pH 7.7 buffer and homogenized. The homogenate was centrifuged at 20,000 rpm for 15 minutes. Supernatant was discarded and pellets resuspended in buffer [$Na_2HPO_4$(10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation of (0.5 mL) there was added $^3$H-angiotensin II (50 mM) (10 mL) with or without the test sample and the mixture was incubated at 37° C. for 1 hour. The mixture was then diluted with Tris buffer (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

The potential antihypertensive effects of the compounds described in the present invention may be evaluated using the methodology described below: Male Charles river Sprague-Dawley rats (300–375 gm) were anesthetized with methohexital (Brevital: 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minutes, volume—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30 minute intervals and the increase in the diastolic blood pressure was recorded before and after drug or vehicle administration.

Using the methodology described above, representative compounds of the invention were evaluated and found to exhibit an activity of at least $IC_{50} < 50$ mM thereby demonstrating and confirming the utility of the compounds of the invention as effective AII antagonists.

Thus, the compounds of the invention are useful in treating hypertension. They are also of value in the management of acute and chronic congestive heart failure, in the treatment of secondary hyperaldosteronism, primary and secondary pulmonary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like.

Pharmaceutical formulations prepared to treat intraocular pressure would typically contain about 0.1% to 15% by weight, and preferably 0.5% to 2.0% by weight of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg per patient per day which can be administered in single or multiple doses. Perferably, the dosage range will be about 2.5 to 250 mg per patient per day; more preferably about 2.5 to 75 mg per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methylclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merthoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflunisal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg), chlorothiazide (125-2000 mg), ethacrynic acid (15-200 mg), amiloride (5-20 mg), furosemide (5-80 mg), propranolol (20-480 mg), timolol maleate (5-60 mg), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose rangers can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compounds for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it take for them to enter the darkened chamber is recorded. On entering the dark chamber, they receive a brief electric shock to the feet. The test animals are pretreated with 0.2 mg/kg of the muscarinic antagonist scopolamine with disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not allow this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antiphyschotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced sterotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and a nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered as limiting the invention set forth in the claims appended hereto.

PREPARATION OF 2-ALKYL-QUINAZOLIN-4-(1H)-ONES

EXAMPLE 1

2-Butyl-6-methylquinazolin-4(1H)-one

To a solution of 3.0 g (20 mmol) of 2-amino-5-methylbenzoic acid in 20 mL of dry DMF at 0° C. was added 200 mg of DMAP followed by 6.07 g (60 mmol) of triethyl amine and 5.02 g (40 mmol) of valeryl chloride. The resulting mixture was stirred at 0° C. for 30 minutes. The mixture was heated to 110° C. and monitored by TLC for the formation of the intermediate quinoxazolone (rf=0.8, 40% EtOAc/hexane). Following complete formation of the intermediate 10 g (100 mmol) of $NH_4CO_3$ was added cautiously. Heating was continued to ensure consumption of the quinoxazolone and formation of the polar (rf=0.4, 40% EtOAc/hexane) quinazolin-4(1H-one. The reaction mixture was concentrated in vacuo and the residue was taken up in 50 mL of ether and 50 mL of water. The mixture was filtered and the filtrate discarded after washing the residue with 20 mL of water. The residue was recrystallized from MeOH to give 1.07 g (5 mmol) of a white crystaline solid. 25% yield overall. $^1$H-NMR (CDCl$_3$): 0.94 (t, 3H, J=6.7 Hz), 1.50 (m, 2H), 1.83 (m, 2H), 2.49 (s, 3H), 2.78 (t, 2H), 7.60 (m, 2H), 8.05 (m, 1H). Anal ($C_{13}H_{16}N_2O$), C, H, N.

EXAMPLE 2

6-Methyl-2-propylquinazoline-4(1H)-one

The 2-propyl derivative was prepared in the identical fashion as the 2-butyl derivative through the use of butyryl chloride in place of valeryl chloride. The product was recrystallized from hexane/acetone to give white crystals. 32% yield. $^1$H-NMR (CDCl$_3$): 11.51 (bs, 1H), 8.08 (s, 1H), 7.60 (s, 2H), 2.78 (3 line m, 2H), 2.01 (s, 3H), 1.92 (m, 2H), 1.09 (t, 3H).

EXAMPLE 3

2-Butyl-7-methylquinazoline-4(1H)-one

Same procedure as in Example 1 with valeroyl chloride and 2-amino-4-methylbenzoic acid. The product was recrystallized from MeOH recovering 0.91 g (4.2 mmol). 21% yield overall. $^1$H-NMR (CDCl$_3$): 0.99 (t, 3H, J=7.4 Hz), 1.49 (m, 2; H), 1.86 (m, 2H), 2.50 (s, 3H), 2.76 (t, 2H, J=7.81 Hz), 7.28 (d, 1H, J=8.3 Hz), 7.49 (s, 1H), 8.15 (d, 1H, J=8.3 Hz). Anal ($C_{13}H_{16}N_2O$), C, H, N.

EXAMPLE 4

2-Butyl-naphtho[2,3-e]quinazoline-4(1H)-one

Same procedure as in Example 1 with valeroyl chloride and 2-aminonaphthoic acid. Product was recrystallized from MeOH. A contaminant co-crystallizes with the desired product. The contaminant is 25% of the product by $^1$H-NMR. Recovered 1.6 g (59% yield). $^1$H-NMR (CDCl$_3$): 0.97 (t, 3H, J=7.3 Hz), 1.42 (m, 2H), 1.75 (m, 2H), 2.48 (t, 2H, J=7.4 Hz), 7.42 (t, 1H, J=7.8 Hz), 7.54 (t, 1H, J=8.3 Hz), 7.77 (d, 1H, J=7.8 Hz), 7.82 (d, 1H, J=8.31 Hz), 8.07 (s, 1H), 9.08 (s, 1H), 10.89 (bs, 1H).

EXAMPLE 5

2-Butyl-5-methylquinazoline-4(1H)-one

Same procedure as in Example 1 with valeroyl chloride and 2-amino-6-methylbenzoic acid on a 16 mmol scale. The concentrated reaction mixture was diluted with 50 mL ether and 50 mL $H_2O$. The mixture was agitated for several minutes and then filtered in vacuo. On filtration further crystalline material formed in the filtrate. The filtrate was filtered again. This procedure was repeated a further two times. The precipitates were collected and combined. The ethereal phase was decanted from the aqueous phase, and concentrated to 15 mL. 25 mL of hexanes was then added and the mixture filtered. The combined precipitates were recrystallized from MeOH/$H_2O$ to give 0.73 g (3.37 mmol) of fluffy white crystals. 21% yield. $^1$H-NMR (CDCl$_3$): 0.98 (t, 3H, J=7.38 Hz), 1.48 (m, 2H), 1.87 (m, 2H), 2.75 (dd, 2H, J=8.09 Hz), 2.89 (s, 3H), 7.20 (d, J=6.73 Hz), 7.56 (m, 2H), 11.68 (bs, 1H).

EXAMPLE 6

2-Butyl-6,8-dimethylquinazoline-4(1H)-one

Same procedure as in Example 1 with valeroyl chloride and 2-amino-5,8-dimethylbenzoic acid on a 12 mmol scale. The product collected from filtration of the ether/water mixture was recrystalized from MeOH. $^1$H-NMR and TLC indicated that the product isolated was a 50% mixture of the desired quinazoline and a contaminant. An aliquot of 0.5 g of this material was concentrated onto 5 mL of flash silica and applied to the surface of a flash chromatography column. The column was eluted with 60% EtOAc/hexanes. The first eluted compound (0.14 g) was collected as a TLC homogeneous sample of the desired product. $^1$H-NMR (CDCl$_3$): 0.99 (t, 3H, J=7.32 Hz), 1.48 (m, 2H), 1.85 (m, 2H), 2.44 (s, 3H), 2.58 (s, 3H), 2.75 (dd, 2H, J=7.87, 7.87 Hz), 7.43 (s, 1H), 7.91 (s, 1H), 10.70 (bs, 1H).

EXAMPLE 7

2-Butyl-8-methylquinazoline-4(1H)-one

Same procedure as in Example 1 with valeroyl chloride and 2-amino-6-methylbenzoic acid on a 1 mmol scale. The concentrated reaction mixture was diluted with 20 mL ether/20 mL H$_2$O. The mixture was filtered. The ethereal phase was seperated, dried (MgSO$_4$), filtered and concentrated. The residue was flash chromatographed over silica eluting with 50% EtOAc/hexanes to give rise to 48 mg (0.22 mmol) of a fluffy yellow solid. 22% yield. $^1$H-NMR (CDCl$_3$): 1.02 (t, 3H), 1.52 (m, 2H), 1.88 (m, 2H), 2.62 (s, 3H), 2.79 (dd, 2H), 7.35 (dd, 1H), 1.61 (d, 1H), 8.12 (d, 1H). FABMS: 2.17 (M$^+$+1) calc for C$_{13}$H$_{16}$N$_2$O.

EXAMPLE 8

2-Butyl-6-isopropylquinazoline-4(1H)-one

Same procedure as in Example 1 with valeroyl chloride and 2-amino-5-isopropylbenzoic acid on a 16 mmol scale. The concentrated reaction mixture was partitioned between 20 mL water and 20 mL of ether. A fine white precipitate was removed by filtration and recrystallized from MeOH/water. The first crop gave rise to 0.56 g of fluffy white crystals. $^1$H-NMR (CDCl$_3$): 0.99 (t, 3H, J=7.3 Hz), 1.32 (d, 6H, J=6.89 Hz), 1.48 (m, 2H), 1.85 (m, 2H), 2.77 (3 line m, 2H, J=7.9 Hz), 3.06 (m, 1H), 7.65 (m, 2H), 8.11 (s, 1H), 11.22 (bs, 1H). FABMS: 245 (M$^+$+1) calc for C$_{15}$H$_{20}$N$_2$O.

EXAMPLE 9

2-Butyl-6-thiomethylquinazolin-4(1H)-one

Same procedure as that described in Example 1. However on addition of ether/water to the reaction mixture a precipitate of the quinazolinone was not formed. The aqueous phase was extracted with ether and the combined ethereal extracts were washed with brine and dried over MgSO$_4$. The mixture was filtered and concentrated in vacuo to give a mixture of the desired product and 2-(N-valeroyl-amino)-5-thiomethylbenzamide. This mixture was heated with 2 equivalents of 1N NaOH solution in water at 100° C. until a clear solution was obtained. The solution was cooled, acidified, and filtered to give a pale yellow precipitate. The product was recrystalized from MeOH to give a 73% overall yield of the title compound. $^1$H-NMR (CDCl$_3$-300 MHz): 1.00 (t, 3H, J=7.3 Hz), 1.50 (m, 2H), 1.86 (m, 2H), 2.58 (s, 3H), 2.76 (3line m, 2H, J=7.9 Hz), 7.62 (m, 2H), 8.03 (d, 1H, J=1.9 Hz), 11.11 (bs, 1H).

EXAMPLE 10

2-Butyl-6-nitroquinazolin-4(1H)-one

To a mixture of 326 mg (2 mmol) of 2-cyano-4-nitroaniline in 10 mL of CH$_2$Cl$_2$ at 0° C. was added 0.34 mL (2.4 mmol) of triethylamine and 25 mg of DMAP. To this mixture was added 0.26 ml of valeryl chloride dropwise. The reaction mixture was allowed to warm to room temperature over 1.5 hours and then concentrated in vacuo. The residue was dissolved in 40 ml of EtOAc and washed with 25 ml of water, 25 ml of saturated NaHCO$_3$ and 25 ml of brine. The organic phase was dried over Na$_2$SO$_4$, filtered and concentrated. The residue (0.46 g) was purified by flash chromatography. The residue was absorbed onto 0.6 g of silica which was applied to the surface of a 5.5"×0.75" silica flash chromatography column. The product was eluted with 20% EtOAc/hexanes to give 0.21 g of N-valeryl-2-cyano-4-nitro-anilide (44% yield). 0.1 g (0.42 mmol) of the amide was dissolved in 1.5 mL of MeOH. To this solution was added 138 μL of a 30% hydrogen peroxide solution followed by 330 μL of a 3N NaOH solution. The solution was refluxed for 1.5 hours, cooled and concentrated in vacuo. The residue was dissolved in 10 mL of water. Dropwise addition of a saturated solution of NH$_4$Cl caused the product to precipitate out as 90 mg (0.36 mmol) of a yellow powder. (87% yield. $^1$H-NMR (CDCl$_3$): 1.02 (t, 3H, J=7.32 Hz), 1.52 (m, 2H), 1.90 (m, 2H), 2.82 (dd, 2H, J=8.03 Hz), 7.82 (d, 1H, J=9.01 Hz), 8.56 (dd, 1H, J=2.6, 8.9 Hz), 9.14 (d, 1H, J=2.71 Hz).

EXAMPLE 11

2-Butylquinazolin-4(1H)-one

To a solution of 500 mg 2-aminobenzonitrile (4.23 mmol), 514 mg triethylamine (5.08 mmol), and 50 mg DMAP (0.41 mmol) in 6 mL CH$_2$Cl$_2$ at 0° C. was added 562 mg valeryl chloride (4.66 mmol) dropwise over 1minute. The mixture was warmed to room temperature and stirred for twenty minutes. The mixture was then diluted with water and brine and then was extracted three times with ether. The combined organic material was dried over MgSO$_4$, stripped of solvent in vacuo, and was purified by flash chromatography eluting with 20% ethyl acetate in hexane to give 2-valerylamido-benzonitrile. R$_f$ 0.22 in 20% ethyl acetate in hexane. $^1$H-NMR (300 MHz, CDCl$_3$): 8.42 (d, 1H), 7.60–7.01 (m, 2H), 6.72 (m, 1H), 4.40 (br s, 1H), 2.46 (t, 2H), 1.74 (m, 2H), 1.43 (m, 2H), 0.97 (t, 3H).

To a solution of 5.1 g of the amide in 90 mL methanol were added 21 mL 3N NaOH and 10 ml 30% H$_2$O$_2$ at room temperature. The mixture was refluxed for 30 minutes and concentrated in vacuo. Water and sat. NH$_4$Cl was added and the mixture extracted 3 times with ether. The combined organic extracts were dried over MgSO$_4$, filtered and concentrated in vacuo and the residue was recrystallized from hexane/acetone to give two crops of the product as white needles. 2.2 g, 43% yield. R$_f$: 0.16 in 20% EtOAc in CH$_2$Cl$_2$. $^1$H-NMR (CDCl$_3$): 8.29 (m, 1H), 7.81–7.68 (m, 2H), 7.47 (m, 1H), 2.79 (3 line m, 2H), 1.87 (m, 2H), 1.51 (m, 2H), 1.00 (t, 1H).

EXAMPLE 12

6-Bromomethyl-2-butylquinazolin-4(1H)-one

To a suspension of 2.6 g (12 mmol) of the product of Example 2 in 100 mL of dry CCl$_4$ was added 2.56 g of N-bromosuccinimide followed by 200 mg of benzoyl peroxide. The reaction mixture was heated to reflux for 45 minutes at which time a precipitate formed throughout. The reaction mixture was concentrated in vacuo and the residue partitioned between 150 mL of EtOAc and 100 mL of water. The mixture was shaken and then filtered to give 1.59 g of the title compound (45% yield). The filtrate was seperated into two phases and the organic phases was washed with 75 mL of sat. NaHCO$_3$ solution followed by 75 mL of water and 75 mL of brine. The organic phase was dried over MgSO₄, filtered and the filtrate was concentrated in vacuo. The residue was purified by recrystalization from EtOAc to give 0.52 g (1.76 mmol) of the same product as was recovered above. Total yield 60%. ¹H-NMR (CDCl₃): 1.00 (t, 3H, J=7.33 Hz), 1.49 (m, 2H), 1.84 (m, 2H), 2.77 (3 line m, 2H, J=7.7 Hz), 4.61 (s, 2H), 7.68 (d, 1H, J=8.4 Hz), 7.80 (dd, 1H, J=8.4, 2.1 Hz), 8.27 (d, 1H, J=2.1 Hz), 11.02 (bs, 1H).

EXAMPLE 13

5-Bromomethyl-2-butylquinazolin-4(1H)-one

The product of Example 5 was treated as in Example 13 to give a 71% yield of a white solid. ¹H-NMR (CDCl₃): 1.0 (t, 3H, J=7.3 Hz), 1.53, (m, 2H), 2.90 (m, 2H), 2.81 (3 line m, 2H, J=7.98 Hz), 5.31 (s, 2H), 7.45 (m, 1H), 7.71 (m, 2H), 11.28 (bs, 1H).

EXAMPLE 14

6-Acetoxymethyl-2-butylquinazolin-4(1H)-one

To a solution of 2.1 g (7.0 mmol) of the quinazolinone prepared in Example 12 in 15 mL of dry DMF was added 1.74 g (20.0 mmol) of sodium acetate. The mixture was heated to 60° C. for 3 hours. The reaction mixture was concentrated in vacuo and the residue dissolved in 100 mL of CH₂Cl₂. The solution was washed with water (3×20 mL), brine (1×20 mL) and dried over MgSO₄. The mixture was filtered and concentrated in vacuo. The residue was recrystallized from MeOH/H₂O to give 1.31 g (4.8 mmol) of a colorless solid. 68% yield. ¹H-NMR (CDCl₃): 0.99 (t, 3H, J=7.32 Hz), 1.50 m, 2H), 1.83 (m, 2H), 2.14 (t, 3H), 2.77 (3 line m, 2H, J=7.71 Hz), 5.23 (s, 2H), 7.69–7.78 (m, 2H), 8.25 (s, 1H), 10.90 (bs, 2H).

EXAMPLE 15

5-Acetoxymethyl-2-butylquinazolin-4(1H)-one

The product of Example 13 was treated as in Example 14 to give after recrystallization from EtOAc a 77% yield of the desired acetylated product.

¹H-NMR (CDCl₃): 0.98 (t, 3H, J=7.38Hz), 1.50 (m, 2H), 1.88 (m, 2H), 2.19 (s, 3H), 2.77 (3 line m, 2H, J=7.93 Hz), 5.85 (s, 2H), 7.48 (m, 1H), 7.70 (m, 2H), 11.65 (bs, 1H).

EXAMPLE 16

6-Nitro-2-propylquinazolin-4(1H)-one

To a solution of 16.3 g (0.1 mol) of 2-amino-5-nitrobenzonitrile in 200 ml of CH₂Cl₂ at 0° C. was added 21 ml (0.15 mol) of triethyl amine followed by 0.3 g of DMAP and 11.71 g (0.11 mol) of butyryl chloride. The reaction mixture was warmed to room temperature and then heated over night at 50° C. The solution was washed with 1N HCl (1×20 ml), water (1×20 ml), saturated NaHCO₃ (2×20 ml) and brine (1×20 ml) and dried over MgSO₄. The solution was filtered and concentrated in vacuo. The residue was dissolved in 200 ml of MeOH to which was added 44 ml (0.22 mol) of 5M NaOH solution followed by the dropwise addition of 25 ml (0.22 mol) 30% H₂O₂ and 50 ml of water. The mixture was refuxed for 4 hours, cooled and filtered. The filtrate was acidified with 1N HCl and the resulting precipitate recovered by filtration. The residue was recrystalized from MeOH to give 8.3 g (0.036 mol) of pale brown fluffy crystals. 36% yield.

¹H-NMR (CDCl₃): 1.10 (t, 3H, J=7.4Hz), 1.93 (m, 2H), 2.79 (3 line m, 2H, J=7.3Hz), 7.80 (d, 1H, J=8.9Hz), 8.55 (dd, 1H, J=2.5, 8.8Hz), 9.14 (bs, 1H).

PREPARATION OF
5-Alkyl-2-aryl-2,4-dihydro-3H-1,2,4-triazol-3-ones

EXAMPLE 17

2-(2-chlorophenyl)-5-Butyl-2,4-dihydro-3H-1,2,4-triazol-3-one

Step A: Preparation of ethyl valerimidate (Free Base)

A 12.7 g (76.7 mmol) sample of ethyl valerimidate hydrochloride (prepared from valeronitrile, ethanol, and hydrogen chloride gas as described in A. J. Hill and I. Rabinowitz, J. Am. Chem. Soc., 1926, 48, 734) was dissolved in 33% (w/w) potassium carbonate solution (made by dissolving 15 g of K₂CO₃ in 30 mL of H₂O) and immediately extracted with either (3×40 mL). The combined ether layers were dried over Na₂SO₄, filtered, and concentrated in vacuo to give 7.09 g (72%) of the product as a clear oil, which was used directly in the next step.

¹H NMR (300 MHz, CDCl₃, ppm): δ0.88 (t, J=7 Hz, 3H), 1.24 (t, J=7Hz, 3H), 1.31 (m, 2H), 1.50 (m, 2H), 2.19 (t, J=7.5 Hz, 2H), 4.06 (q, J=7 Hz, 2H), 6.84 (br s, 1H).

Step B: Preparation of ethyl N-carbethoxyvalerimidate

A solution of 6.5 g (50.3 mmol) of ethyl valerimidate (free base) in 90 mL of dry CH₂Cl₂ was treated with 7.71 mL (5.60 g, 55.3 mmol) of triethylamine. The resulting solution was stirred under N₂ at −10° C. in an ice-salt bath as a solution of 4.81 mL (5.46 g, 50.3 mmol) of ethyl chloroformate in 10 mL of CH₂Cl₂ was added dropwise over 25 minutes. Upon completion of the addition, the cooling bath was removed, and the mixture was stirred at room temperature for 2 hours. Next, the solvent was removed by evaporation in vacuo. The residue was taken up in hexane and filtered to remove triethylamine hydrochloride. Concentration of the filtrate yielded 7.08 g (70%) of the product as a yellow oil, suitable for use in the next step without further purification. NMR indicated a mixture of syn and anti isomers. TLC (98:2 CH₂Cl₂-MeOH) showed a close pair of spots, R_f 0.48, 0.52.

¹H NMR (200 MHz, CDCl₃, ppm): δ0.86 (distorted t, J=7.5 Hz, 3H), 2.15–2.35 (m, 8H), 2.4–2.65 (m, 2H), 2.19, 2.35 (t, J=7.5 Hz, 2H total), 4.0–4.2 (m, 4H). EI-MS: m/e 201 (M+).

Step C: Preparation of 5-butyl-2-(2-chlorophenyl)-2,4-dihydro-3H-1,2,4-triazol-3-one To a solution of 285 mg (2 mmol) of (2-chlorophenyl)hydrazine (generated from the hydrochloride by partitioning between ether and 1N Na₂CO₃) in 3 mL of toluene was added 442 mg (2.2 mmol) of ethyl -carbethoxyvalerimidate (Example 4 Step B). The mixture was heated at 45°–50° C. for 45 minutes. At this time the mixture was treated with 307 mL (223 mg, 2.2 mmol) of triethylamine and then heated overnight at 95° C. The mixture was cooled and concentrated in vacuo. Flash chromatography of the residue on silica gel (gradient elution with 0.6–2% methanol in CH₂Cl₂) gave 257 mg (51%) of the product as an off-white solid, mp 103°–104° C. homogeneous by TLC in 19:1 CH₂Cl₂-MeOH.

¹H NMR (200 MHz, CDCl₃, ppm): δ0.92 (t, J=7 Hz, 3H), 1.38 (m, 2H), 1.68 (m, 2H), 2.57 (t, J=7.5 Hz, 2H), 7.3–7.55 (m, 4H), 12.04 (br s, 1H).

FAB-MS: m/e 252 (M+1).
Analysis for C₁₂H₁₄ClN₃O
Calcd: C, 57.26; H, 5.61; N, 16.69.
Found: C, 57.31; H, 5.69; N, 16.58.

PREPARATION OF 5.6 DIALKYL PYRIMIDIN-4(3H)-ONE

EXAMPLE 18

2-n-Butyl-5-ethyl-6-methylpyrimidin-4(3H)-one

A solution of 3.0 g valeramidine hydrochloride, 3.47 g ethyl 2-ethylacetoacetate, and 5.8 mL triethylamine in 20 mL DMF was heated to 120° C. for 18 hours. The mixture was diluted with brine and extracted three times with ether. The combined organic material was washed with brine, was dried over MgSO₄, was stripped of solvent in vacuo, and then was still flash chromatographed in 3% MeOH in CH₂Cl₂ to give the title compound as a white solid.

¹H NMR (300 MHz, CDCl₃) §2.62 (3 line n, 2H), 2.51 (4 line m, 2 H), 2.32 (s, 3), 1.75 (m, 2H), 1.42 (6 line m, 2H), (1.10 (3 line m, 3H), 0.95 (3 line m, 3H).

EXAMPLE 19

2-n-Butyl-5,6-dimethylpyrimidin-4(3H)-one

The title compound is prepared using the procedure in Example 18 and ethyl 2-methylacetoacetate in place of ethyl 2-ethylacetoacetate.

PREPARATION OF 3-N-ALKYL-2-ALKYLQUINAZOLIN-4(3H)-ONE

A general procedure for the synthesis of 3-N-alkylated-quinazolin-4(3H)-ones is given below.

A suspension of 1.1 mmol of NaH in 2 mL of dry DMF at 0° C. under nitrogen is treated with 1 mmol of the quinazolin-4(1H)-one as a solid (most quinazolin-4(1H)-ones prepared were insoluble in DMF). Immediate evolution of hydrogen could be observed as the quinazolin-4(1H)-one is deprotonated and dissolves. After 30 minutes the solution was warmed to room temperature for a further 30 minutes. To this solution cooled to 0° C. is added a solution of 1 mmol of the appropriate bromomethylphenyl/methanesulfonylmethylphenyl thiophene, benzothiophene or furan, as prepared below, in 1.5 mL of DMF. After 30 minutes, the reaction mixture is warmed to room temperature and stirred overnight. The solution is concentrated in vacuo, and the residue dissolved in 50 mL of EtOAc. The solution is washed with water (3×10 mL) and brine (2×10 mL). The organic phase is dried over MgSO₄, filtered and concentrated in vacuo. The residue is then chromatographed on a silica gel column.

The procedure herein described can be used to generate 5-alkyl-2-aryl-3-N-alkyl-'2,4-dihydro-1,2,4-triazol-3-ones and 2,5,6-trialkyl-3-N-alkylpyrimidin-4-(3H)-one. The general procedures for preparing the methanesulfonylmethylphenyl bromomethylphenyl thiophenes, benzothiophenes and furans are described below using quinaolinones and 2,4-dihydro-1,2,4-triazol-3-ones.

EXAMPLE 20

2-Butyl-6-methyl-3-[[4-[3-(1H-tetrazol-5-yl)-4-thienyl]-phenyl]methyl]quinazolin-4(3H)-one (Compound 2 of Table VII)

Step A: Preparation of 3-bromo-4-(4-methylphenyl)thiophene (scheme II-1. compound 1a)

Through a solution of p-tolyltrimethyltin (3.17 g, 12.4 mmol) in dry toluene (8 mL) was bubbled N₂ for 5 min to degas the solution. To this was added 3,4-dibromothiophene (2.31 g, 9.56 mmol) and a catalytic amount of Pd(PPh₃)₄ (552 mg, 5 mol %). The reaction mixture was brought to reflux (120° C.) and left overnight. The reaction was cooled to rt and the toluene was replaced by EtOAc. The insoluable salts were removed by filtration through a plug of celite. The product was purified by flash chromatography on a silica column eluting with hexane to afford 1.09 g (45%) of the titled compound as a clear, colorless oil.

¹H NMR (300 MHz, CDCl₃) δ2.39 (s, 3H), 7.21–7.26 (m, 4H), 7.33 (d, 1H), 7.38 (d, 1H); FAB mass spectrum, m/e 252/254 (m+, calcd for C₁₁H₉SBr, 253).

Step B: Preparation of 3-cyano-4-(4-methylphenyl)thiophene (scheme II-1, compound 1b)

To a solution of the product of Step A (329 mg, 1.30 mmol) in quinoline (3 mL) was added CuCN (233 mg, 2.60 mmol) and the solution heated to reflux (235° C.) overnight. The reaction was cooled and Et₂O was added. The solution was washed with 9N HCl and brine, dried over anhydrous MgSO₄, and filtered. The product was purified by flash chromatography on a silica column using Hex/EtOAc (35:1) to afford 174 mg (67%) of the titled compound as a light yellow solid.

¹H NMR (200 MHz, (CDCl₃) δ2.42 (s, 3H), 7.28 (d, 2H), 7.36 (d, 1H), 7.53 (d, 2H), 8.04 (d, 1H); FAB mass spectrum, m/e 199 (m+, calcd for C₁₂H₉SN, 199).

Step C: Preparation of 3-N-triphenylmethyltetrazolyl-4-(4-methylphenyl)thiophene (scheme II-1. compound 1c)

To a solution of the product of Step B (174 mg, 0.873 mmol) in dry toluene (7 ml) was added Me₃SnN₃ (1.07 g, 5.22 mmol) and the solution brought to reflux (130° C.). A white solid that is product precipitates. The reaction was left overnight. There was still starting material present and another 363 mg of Me₃SnN₃ was added. After an additional 5 hours the reaction was cooled to RT. To the reaction was added CH₂Cl₂ and the reaction was washed with 2N HCl and water, dried over MgSO₄ and filtered. The volume was reduced and NEt₃ (244 μl, 1.75 mmol) and Ph₃CCl (219 mg, 0.787 mmol) were added. After 2 hours Et₂O/EtOAc was added to the reaction and the solution was washed with 10% citric acid, 1N NaOH and water, dried over MgSO₄ and filtered. The titled compound was isolated in 94% yield, Rf=0.33 (10:1 hex/EtOAc).

¹H NMR (300 MHz, CDCl₃) δ2.31 (s, 3H), 6.95 (d, 8H), 7.09 (d, 2H), 7.21–7.34 (m, 10H), 8.00 (d, 1H); FAB mass spectrum, m/e 485 (m+1, calcd for C₃₁H₂₄SN₄, 485).

Step D: Preparation of 3-N-triphenylmethyltetrazolyl-4-(4-bromomethylphenyl)thiophene (scheme II-1. compound 1e, R=H)

To a solution of the product of Step C (329 mg, 0.680 mmol) in dry CCl$_4$ (3 mL) was added NBS (133 mg, 0.749 mmol) and a catalytic amount of AIBN. The mixture was heated to reflux (100° C.). After 2 h the reaction was cooled to rt and the insoluable succinimide removed by filtration. The solvent was replaced by EtOAc and washed with 1N NaOH and brine, dried over MgSO$_4$ and filtered. The solvent was removed to afford 428 mg (100%) of the crude product as a yellow foam. Rf=0.32 (10:1/Hex:EtOAc).

Step E: Preparation of 2-butyl-6-methyl-3-[[4-[3-(N-triphenylmethyltetrazole)-4-thienyl]phenyl]methyl]quinazolin-4-(3H)-one (Scheme II-8, compound 8b)

To a solution of 2-butyl-6-methylquinazolinone (105 mg, 0.487 mmol) in dry DMF (2 mL) under N$_2$ was added NaH (25.3 mg, 0.843 mmol). The reaction was allowed to stir for 30 min. To this was added a solution of the product of Step D (0.340 mmol, crude) in dry DMF (1 mL). After 5 h the reaction was quenched with sat'd NH$_4$Cl solution. The DMF was replaced with CH$_2$Cl$_2$ and the mixture filtered. The product was purified by flash chromatography on a silica column using a gradient of Hex/EtOAc (15:1-7) to yield 74.0 mg (29% 2 steps) of the major product, Rf=0.33 (3:1 Hex/EtOAc).

$^1$H NMR (300 MHz, CDCl$_3$) δ0.87 (t, 3H), 1.31–1.38 (sextet, 2H), 1.68–1.73 (quintet, 2H), 2.48 (s, 3H), 2.65 (t, 2H), 5.33 (s, 2H), 6.90–7.28 (m, 24H), 7.57 (s, 2H), 8.02 (dd, 1H), 8.10 (s, 1H).

Step F: Preparation of 2-butyl-6-methyl-3-[[-[3-(1H-tetrazol-5-yl)-4-thienyl]-phenyl]methyl]quinazolin-4-(3H)-one. (Compound 2 of Table VII)

To a solution of the product of Step E (74.0 mg, 0.106 mmol) in methanol (3 mL) was added 9N HCl (10 drops). Within 30 min the reaction was completed. The methanol was removed and the product triturated with Et$_2$O to yield 45.9 mg (88%) of the titled product, Rf=0.73 (50:10:1 CHCl$_3$/MeOH/HOAc). FAB mass spectrum, m/e 457 (M+1, calcd for C$_{25}$H$_{24}$SON$_6$ 457).

$^1$H NMR (300 MHz, CD$_3$OD) δ0.97 (t, 3H), 1.48–1.70 (sextet, 2H), 1.71–1.75 (quintet, 2H), 2.61 (s, 3H), 3.15 (t, 2H), 5.61 (s, 2H), 7.28–7.46 (m, 4H), 7.68 (d, 1H), 7.73 (d, 1H), 7.95 (dd, 1H), 8.09 (d, 1H), 8.23 (s, 1H).

EXAMPLE 21

2-Butyl-6-methyl-3-[[4-[2-bromo-3-[1H-tetrazol-5-yl)-4-thienyl]phenyl]methyl]quinazolin-4-(3H)-one (Compound 17 of Table VII)

Step A: Preparation of 2-bromo-3-(N-triphenylmethyltetrazol-5-yl)-4-(4-methylphenyl)thiophene (scheme II-1, compound 1d R=Br)

To a solution of the product of Example 20 Step C (101 mg, 0.208 mmol) in dry THF (2 ml) cooled to −78° C. with a dry ice/acetone bath under N$_2$ was added a 1.7M tBuLi solution (0.190 ml, 0.323 mmol). The reaction turned slowly from orange to red then the color dissipated. Another 0.190 ml of tBuLi was added to the reaction. As soon as the red color persisted Br$_2$ (0.40 ml, 0.42 mmol) was added. The product was purified by flash chromatography on a silica column using Hex/EtOAc (35:1). Removal of the solvent afforded 60 mg (51%) of the crude titled product. Rf=0.48 (10:1 Hex/EtOAc).

Step B: Preparation of 2-bromo-3-N-triphenylmethyltetrazol-5-yl-4-(4-bromomethylphenyl)thiophene (scheme II-1, compound 1e, R=Br)

To a solution of the product of Step A (22 mg crude) in dry CCl$_4$ (3 mL) was added NBS (7 mg, 0.0448 mmol) and a catalytic amount of AIBN. The reaction was brought to reflux (100° C.). After 2 h the reaction was cooled to rt and the insoluable succinimide was removed by filtration. The solvent was replaced by Et$_2$O/EtOAc and washed with 1N NaOH and brine, dried over MgSO$_4$ and filtered. Removal of the solvent afforded 43 mg (100%) of the crude titled compound. Rf=0.66 (3:1/Hex:EtOAc).

Step C & D: Alkylation and deprotection, following the procedure of e.g. 20, Steps E through F, provides the titled compound.

EXAMPLE 22

2-Butyl-6-methyl-3-[[4-[2-(1H-tetrazol-5yl)-3-thienyl]-phenyl]methyl]quinazolin-4(3H)-one (Compound 14 of Table VII)

Step A: Preparation of 2-[(N-triphenylmethyltetrazol-5-yl]thiophene (scheme II-3, compound 3a, Y=S)

To a solution of 2-cyanothiophene (1.4 g; 12.8 mmol) in dry toluene (10 ml) was added Me$_3$SnN$_3$ (2.8 g; 13.65 mmol). The mixture was stirred at reflux under N$_2$ for 12 hours. The reaction was cooled to room temperature diluted with CH$_2$Cl$_2$ and washed with 2N HCl soln and H$_2$O. The organic was dried over anhydrous MgSO$_4$ and concentrated in vacuo. The residue, containing the free tetrazole, was dissolved in CH$_2$Cl$_2$ (10 mL) and Ph$_3$CCl (3.2 g; 0.9 equiv.) and NEt$_3$ (3.6 mL) were added. After 20 minutes the mixture was diluted with Et$_2$O/EtOAc and washed with 1N NaOH, 10% citric acid and brine. The organic was dried over anhydrous MgSO$_4$ and concentrated in vacuo. The product was purified by recrystallization from hexanes. The titled compound was isolated in 80% yield, Rf=0.33 (10:1 hex/EtOAc).

$^1$H NMR (200 MHz, CDCl$_3$), δ7.12–7.21 (comp, 8H), 7.28–7.40 (comp, 8H), 7.42 (dd, 1H), 7.79 (dd, 1H).

Step B: Preparation of 2-trimethylsilyl-5-(N-triphenylmethyltetrazol-5-yl)thiophene (scheme II-3, compound 3b, Y=S)

A solution of the product of Step A (1.00 g, 2.54 mmol) in dry THF (10 ml) under N$_2$ was cooled to −20° C. with a dry ice/acetone bath. To this was added 1.6M nBuLi solution (2.38 ml, 3.81 mmol) by syringe. The reaction mixture turned orange then red and cloudy. The reaction was warmed to −10° C. and stirred for 45 min. The reaction was then cooled to −50° C. and TMSCl (0.322 mL, 2.54 mmol) was added by syringe. The reaction was warmed to 0° C. and quenched with sat'd NH$_4$Cl solution (5 drops). The solvent was replaced by Et$_2$O/EtOAc and washed with water and brine, dried over MgSO$_4$ and filtered. The product was purified by flash chromatography on a silica column eluting with Hex/EtOAc (40:1). Removal of the solvent affored 849 mg (72%) of the titled product as a slightly orange solid. Rf=0.40 (15:1/Hex:EtOAc).

¹H NMR (400 MHz, CDCl₃) δ0.32 (s, 9H), 7.13-7.15 (m, 5H), 7.22 (d, 1H), 7.31-7.33 (m, 10H), 7.82 (d, 1H).

Step C: Preparation of 2-trimethylsilyl-4-trimethyltin-5-(N-triphenylmethyltetrazol-5-yl)thiophene (scheme II-3l, compound 3c, Y=S).

A solution of the product of Step B (752 mg, 1.61 mmol) in dry THF (6 mL) under N₂ was cooled to −20° C. with a dry ice/acetone bath. To this was added a 1.6M nBuLi solution (1.53 ml, 2.45 mmol) by syringe. The reaction turned red. As the reaction was warmed to −10° C., the color began to return to orange indicating quenching. The reaction was cooled again to −20° C. and another 1.53 ml of the nBuLi solution was added. The solution turned dark red. The reaction was warmed to −10° C. and allowed to stir at this temperature for 45 min. The reaction was cooled to −60° C. and a solution of Me₃SnCl (844 mg, 4.24 mmol) in dry THF (2 ml) was added by cannula.

The reaction was warmed to rt and quenched with sat'd NH₄Cl solution. To the flask was added Et₂O/EtOAc and the solution washed with 1N NaOH and brine, dried over MgSO₄ and filtered. The product was purified by flash chromatography on a silica column eluting with Hex/EtOAc (50:1). Removal of the solvent affored 879 mg (87%) of the titled compound as a white solid. Rf=0.54 (10:1/Hex:EtOAc).

¹H NMR (200 MHz, CDCl₃) δ0.13 (s, 9H), 0.35 (s, 9H,) 7.12-7.35 (m, 16H).

Step D: Preparation of 2-trimethylsilyl-4-(4-(1-methoxycarbonyl)phenyl)-5-(N-triphenylmethyltetrazol-5-yl)thiophene (scheme II-3, compound 3d, Y=S)

To a concentrated solution of the product of Step C (194 mg, 0.308 mmol) in dry DMF (1.5 ml) was added p-iodomethylbenzoate (153 mg, 0.583 mmol) and Pd(PPh₃)₂Cl₂ (22 mg, 10 mol %). The reaction was heated at 75° C. for several hrs. Because some trityl had been removed by the heat, NEt₃ (0.0645 mL, 0.463 mmol) and Ph₃CCl (59 mg, 0.21 mmol) were added. The DMF was replaced by EtOAc and the product was purified by flash chromatography on a silica column eluting with Hex/EtOAc (15:1). Removal of the solvent affored 116 mg of the titled compound as a white solid. Rf=0.32 (10:1/Hex:EtOAc).

Step E: Preparation of mesylate 3e (scheme II-3, compound 3e, Y=S)

To a solution of the product of step D (116 mg crude) in dry THF (2 ml) under N₂ and cooled to 0° C. was added an LAH solution (0.580 ml, 0.580 mmol) by syringe. When the gas evolution subsided, about 5 min, the ice bath was removed and the reaction warmed to RT. To the reaction was added Et₂O then 1 drop water, 1 drop 5.0N NaOH, and 1 drop water. The insoluable salts precipitated. MgSO₄ was added and the solids were removed by filtration. Removal of the solvent afforded 142 mg (100% 2 steps) of the crude primary alcohol. Rf=0.41 (2:1/Hex: EtOAc). The primary alcohol (142 mg crude) was dissolved in dry CH₂Cl₂ (1.5 mL) under N₂ and was cooled to 0° C. To this solution was added NEt₃ (0.0595 mL, 0.429 mmol), CH₃SO₂Cl (0.030 mL, 0.388 mmol), and a catalytic amount of 4-dimethylaminopyridine (2 mg, 9 mol %). The reaction was kept at 0° C. After an hour the reaction was warmed to rt and Et₂O/EtOAc was added to the reaction. The solution was washed with 10% citric acid, 1N NaOH and brine, dried over MgSO₄, and filtered. Removal of the solvent afforded 113 mg (90% for steps D through E) of the crude titled compound. Rf=0.42 (2:1/Hex: EtOAc). The mesylate was used crude without further purification.

Steps F and G: Alkylation with the product of example 19, Step E, following the procedure of Example 17, Steps E through F provides the titled compound

EXAMPLE 23

2-Butyl-6-methyl-3-[[4-[2-(1H-tetrazol-5yl)-3-furanyl]-phenyl]methyl]quinazolin-4-(3H)-one (Compound 27 of Table VII)

Step A: Preparation of 2-[(N-triphenylmethyl)tetrazol-5-yl]furan (scheme II-3, compound 3a, Y=O)

To a solution of 2-cyanofuran (3.84 g; 41.3 mmol) in dry toluene (30 mL) was added Me₃SnN₃ (10 g; 1.2 equiv.). The mixture was stirred at reflux under N₂ for 12 hours. The reaction mixture was diluted with CH₂Cl₂ and washed with 2N HCl soln and H₂O. The organic was dried over anhydrous MgSO₄ and concentrated in vacuo. The residue was dissolved in CH₂Cl₂ (20 mL) and NEt₃ (11.0 mL; 2 equiv.) and Ph₃CCl (10.3 g; 0.9 equiv.) were added. After 1 hour the mixture was diluted with Et₂O/EtOAc and washed with 10% citric acid, 1N NaOH and brine. The organic was dried over MgSO₄ and concentrated in vacuo. The product was crystallized from hexanes. The title compound was isolated in 35% yield, Rf=0.30 (10:1 hex/EtOAc).

¹H NMR (200 MHz, CDCl₃) δ6.53 (dd, 1H), 7.08-7.18 (comp, 6H), 7.21-7.40 (comp, 10H), 7.57 (dd, 1H).

Step B: Preparation of 2-trimethylsilyl-5-(N-triphenylmethyltetrazol-5-yl)furan (scheme II-3, compound 3b, Y=O)

A solution of the product of Step A (1.00 g, 2.65 mmol) in dry THF (10 mL) under N₂ was cooled to −20° C. with a dry ice/acetone bath. To this was added 1.6M n BuLi solution (2.5 mL, 4.0 mmol). The reaction slowly turned red in color. As the reaction was warmed to −10° C., the color changed to brown and the reaction became cloudy. The reaction was cooled to −50° C. and TMSCl (0.335 mL, 2.64 mmol) was added by syringe. The reaction was warmed to 0° C. and quenched with sat'd NH₄Cl solution (6 drops). The solvent was replaced by EtOAc and washed with brine, dried over MgSO₄ and filtered. The product was purified by flash chromatography on a silica column eluting with Hex/EtOAc (40:1). Removal of the solvent affored 590 mg (50%) of the titled product as a white solid. Rf=0.32 (15:1/Hex:EtOAc).

¹H NMR (400 MHz, CDCl₃) δ0.29 (s, 9H), 6.69 (d, 1H), 7.04 (d, 1H), 7.12-7.35 (m, 15H).

Step C: Preparation of 2-trimethylsilyl-4-trimethyltin-5-(N-triphenylmethyltetrazol-5-yl)furan (scheme II-3, compound 3c, Y=O)

A solution of the product of Step B (532 mg, 1.18 mmol) in dry THF (5 mL) under N₂ was cooled to −20° C. with a dry ice/acetone bath. To this was added 1.6M nBuLi solution (1.13 mL, 1.81 mmol) by syringe. A light red color developed. The reaction was warmed to −10° C. and allowed to stir at this temperature for 45 min. Because the color faded another 1.13 ml of 1.6M nBuLi was added. The reaction was cooled to −60° C. and a solution of Me$_3$SnCl (500 mg, 2.5 mmol) in dry THF (1.5 mL) was added by cannula. The reaction was warmed to rt. To the flask was added Et$_2$O/EtOAc and the solution washed with 1N NaOH, water, and brine, dried over MgSO$_4$ and filtered. The product was purified by flash chromatography on a silica column eluting with Hex/EtOAc (50:1). Rf=0.54 (10:1/Hex:EtOAc). Removal of the solvent affored 520 mg (72%) of the titled compound as a white solid.

$^1$H NMR (400 MHz, CDCl$_3$) δ0.05 (s, 9H), 0.30 (s, 9H), 6.68 (s, 1H), 7.10–7.13 (m, 5H), 7.30–7.32 (m, 10H).

Step D: Preparation of 2-trimethylsilyl-4-(4-(1-methoxycarbonyl)phenyl)-5-(N-triphenylmethyltetrazol-5-yl)furan (scheme II-3, compound 3d, Y=O)

To a concentrated solution of the product of Step C (187 mg, 0.305 mmol) in dry DMF (1.5 mL) was added p-iodomethylbenzoate (160 mg, 0.612 mmol) and Pd(PPh$_3$)$_2$Cl$_2$(22 mg, 10 mol %). The reaction was heated at 75° C. for several hrs. Because some trityl had been removed by the heat, NEt$_3$ (0.043 mL, 0.31 mmol) and Ph$_3$CCl (41 mg, 0.15 mmol) were added. The DMF was replaced by EtOAc and the product was purified by flash chromatography on a silica column eluting with a gradient of Hex/EtOAc (30:1-15:1). Removal of the solvent affored 100 mg (56%) of the titled compound. Rf=0.23 (10:1/Hex:EtOAc).

$^1$H NMR (400 MHz, CDCl$_3$) δ0.34 (s, 9H), 3.93 (s, 3H), 6.86 (s, 1H), 7.05–7.07 (m, 6H), 7.24–7.34 (m, 9H), 7.54 (d, 2H), 7.86 (d, 2H).

Step E: Preparation of 3-(4-(1-methanesulfonyloxymethyl)phenyl)-2-(N-triphenylmethyltetrazol-5-yl)furan (scheme II-3, compound 3e, Y=O)

To a solution of the product of Step D (100 mg, 0.172 mmol) in dry THF (2 mL) under N$_2$ and cooled to 0° C. was added an 1.0M LAH solution (0.520 mL, 0.520 mmol) by syringe. When the gas evolution subsided the ice bath was removed and the reaction warmed to rt. To the reaction was added Et$_2$O then 1 drop water, 1 drop 5.0N NaOH, and 1 drop water. The insoluable salts precipitated and MgSO$_4$ was added and the solids removed by filtration. The solvent was removed in vacuo and the crude alcohol, Rf=0.35 (2:1/Hex:EtOAc), was used in the next step without further purification. A solution of the primary alcohol in dry CH$_2$Cl$_2$ (1.5 mL) under N$_2$ was cooled to 0° C. To this solution was added NEt$_3$ (0.0527 mL, 0.378 mmol), CH$_3$SO$_2$Cl (0.0266 mL, 0.344 mmol), and a catalytic amount of 4-dimethylaminopyridine (3 mg, 15 mol %). The reaction was kept at 0° C. After an hour the reaction was warmed to rt and Et$_2$O/EtOAc was added to the reaction. The solution was washed with 10% citric acid, 1N NaOH and brine, dried over MgSO$_4$, and filtered. Removal of the solvent afforded 105 mg (96% 2 steps) of the crude titled compound as a bright yellow solid. Rf=0.43 (2:1/Hex:EtOAc). The mesylate was used crude without further purification.

Steps F & G: The titled compound was completed by alkylation followed by deprotection, following the procedures of Example 20, Steps E through F

EXAMPLE 24

2-Butyl-6-methyl-3-[[4-[2-(N-benzoylsulfonamido)-3-benzothienyl]phenyl]methyl]quinazolin-4-(3H)-one (Compound 38 of Table VII)

Step A: Preparation of 3-(4-methylphenyl)benzothiophene (scheme II-4, compound 4a, Y=S, where R$^{11}$ and R$^{12}$ are joined to form a phenyl ring)

To a solution of 3-bromobenzothiophene (709 mg, 3.33 mmol) and p-tolytrimethyltin (850 mg, 1.0 equiv) in dry toluene (12 mL) under N$_2$ was added Pd(PPh$_3$)$_4$ (192 mg, 5 mol %). The mixture was strirred at reflux for 12 h. The solvent was removed in vacuo and the residue was partially dissolved in hex/EtOAc (10:1) and filtered through a plug of silica. The solvent was removed to afford 658 mg (88%) of crude titled compound. Rf=0.56 (25:1 hex/EtOAc).

Step B: Preparation of 3-(4-methylphenyl)-2-chlorosulfonylbenzothiophene (scheme II-4, compound 4c, Y=S, where R$^{11}$ and R$^{12}$ are joined to form a phenyl ring To a solution of the product of Step A (293 mg, 1.308 mmol) in dry THF (5 mL) cooled to −20° C. under N$_2$ was added 1.6M nBuLi (2.44 mL, 3.0 equiv). The reddish-brown anion was stirred at −20° C. for 50 min then cooled to −70° C. and SO$_2$(g) was bubbled in until the anion color disappeared (ca. 5 min). To the now slightly yellow solution was added N-chlorosuccinamide (350 mg, 2 equiv) and the mixture was stirred for 1 h and warmed to rt by removing the ice bath. The reaction mixture was diluted with Et$_2$O/EtOAc and washed with H$_2$O, 5% NaHO$_3$ soln, and brine. The organic was dried over anhydrous MgSO$_4$ and concentrated in vacuo to afford crude titled compound. Rf=0.45 (25:1 hex/EtOAc).

Step C: Preparation of 3-(4-methylphenyl)-2-(N-t-butylsulfonamido)benzothiophene (scheme II-4, compound 4d, Y=S, where R$^{11}$ and R$^{12}$ are joined to form a phenyl ring)

To a solution of the entire crude product of Step B in dry CH$_2$Cl$_2$ (5 mL) was added tbutylamine (2 mL). The mixture was stirred for 2 days and then diluted with CH$_2$Cl$_2$ and washed with 1N HCl, H$_2$O and brine. The organic was dried over anhydrous MgSO$_4$ and concentrated in vacuo. The product was purified by flash chromatography by first eluting with hex/EtOAc (6:1) and then with CH$_2$Cl$_2$ to afford 115 mg (25% for step B and C) of the tiltled compound. Rf=0.23 (6:1 hex/EtOAc).

$^1$H NMR (400 MHz, CDCl$_3$) δ1.04 (s, 9H), 2.44 (s, 3H), 4.01 (s, 1H), 7.33 (d, 2H), 7.36 (m, 1H), 7.43–7.48 (comp m, 3H), 7.55 (dd, 1H), 7.87 (ddd, 1H); FAB mass spectrum, m/e 360 (m+H, calcd for C$_{19}$H$_{21}$NO$_2$S$_2$, 360).

Step D: Preparation of 3-(4-bromomethylphenyl)-2-(N-t-butylsulfonamido)-benzothiophene (scheme (II-4, compound 4e, Y=S, where R$^{11}$ and R$^{12}$ are joined to form a phenyl ring)

To a solution of the product of Step C (115 mg, 0.3203 mmol) in dry benzene (5 mL) was added a catalytic amount of AIBN and N-bromosuccinamide (68 mg, 1.2 equiv). The mixture was stirred at reflux under N₂ for 3 h. After cooling to rt the reaction mixture was diluted with Et₂O/EtOAc and washed with H₂O and brine. The organic was dried over anhydrous MgSO₄ and concentrated in vacuo to afford 147 mg (100%) of the titled compound. Rf=0.18 (6:1 hex/EtOAc). The bromomethyl compound was used crude without further purification.

Step E: Preparation of 2-butyl-6-methyl-3-[[4-[2-(N-t-butylsulfonamido)-3-benzothienyl]phenyl]methyl]quinazolin-4-(3H)-one (scheme II-10, compound 10a)

To a solution of 2-butyl-6-methylquinazolin-4-(3H)-one from Example 1 in dry DMF was added 80% NaH in oil (1.5 equiv). When H₂ evolution ceased a solution of the product of Step D in DMF was added. The mixture was stirred at rt for 3 h then quenched with satd NH₄Cl soln and concentrated in vacuo. The residue was dissolved in CH₂Cl₂ dried over anhydrous MgSO₄, filtered and concentrated in vacuo. A small sample of the reaction mixture was purified by flash chromatography eluting with hex/EtOAc to provide the titled compound in pure form.

Step F: Preparation of 2-butyl-6-methyl-3-[[4-[2-(sulfonamido)-3-benzothienyl]phenyl]methyl]quinazolin-4-(3H)-one (scheme II-10, compound 10b)

A solution of the entire product of Step E in TFA and anisole (2 drops) was stirred for 24 h. The TFA was removed at high vacuum and crude sulfonamide remained.

Step G: Preparation of 2-butyl-6-methyl-3-[[4-[2-(N-benzoylsulfonamido)-3-benzothienyl]phenyl]methyl]quinazolin-4-(3H)-one (scheme II-10, compound 10c)

To a solution of the product of Step F in dry pyridine was added a catalytic amount of DMAP and benzoyl chloride (10 equiv). After stirring for 3 h the pyridine was removed at high vacuum and the residue was taken up in CH₂Cl₂ and washed with 5% citric acid soln and H₂O. The organic was dried over anhydrous MgSO₄ and concentrated in vacuo. The product was purified by flash chromatography.

EXAMPLE 25

2-Butyl-6-methyl-3-[[4-[2-(N-benzoylsulfonamido)-3thienyl]phenyl]methyl]quinazolin-4-(3H)-one (Compound 12 of Table VII) and 2-Butyl-6-methyl-3-[[4-[5-trimethylsilyl-2-(N-benzoylsulfonamido)-3-thienyl]methyl]quinazolin-4-(3H)-one Step A: Preparation of 3-bromo-2-t-butylsulfonamido-5-trimethylsilylthiophene. (scheme II-5, compound 5a, Y=S)

Part 1: To a solution of 2-thiophenesulfonyl chloride (1.22 g, 6.70 mmol) in dry CH₂Cl₂ (25 mL) at rt was added tBuNH₂ (1.55 mL, 2.2 equiv). After stirring at rt overnight the mixture was diluted with ether and washed with 1N HCl, a sat'd solution of NaHCO₃ and brine. The organic was dried over anhydrous MgSO₄ and concentrated in vacuo to provide 1.42 g (97%) of t-butylsulfonamido-2-thiophene, Rf=0.50 (2:1 hex/EtOAc).

Part 2: To a solution of t-butylsulfonamido-2-thiophene (500 mg, 2.28 mmol) in dry THF (5 mL) cooled to 0° C. under a nitrogen atmosphere was added 1.6M nBuLi (4 mL, 6.4 mmol). After stirring for 30 min trimethylsilylchloride (0.64 mL, 2.2 equiv) was added via syringe. The mixture was stirred for 10 min then 1.6M nBuLi (1.5 mL, 2.4 mmol) was added. After stirring for 30 min Br₂ ((0.26 mL, 1.19 equiv) was added. The mixture was allowed to warm to rt and diluted with ether and washed with 1N NaOH and brine. The organic was dried over anhydrous MgSO₄ and concentrated in vacuo. The product was purified by flash chromatography eluting with hex/EtOAc (8:1) to afford 198 mg (26%) of the titled compound, Rf=0.32 (6:1 hex/EtOAc).

¹H NMR (200 MHz, CDCl₃) d 0.33 (s, 9H), 1.27 (s, 3H), 5.01 (bs, 1H), 7.11 (s, 1H).

Step B: Preparation of 3-p-tolyl-2-t-butylsulfonamido-5-trimethylsilylthiphene. (scheme II-5, compound 5b, Y=S)

To a solution of the product of Step A (176 mg, 0.536 mmol) and p-tolyltrimethyltin (205 mg, 1.5 equiv) in dry DMF (0.8 mL) under nitrogen was added PdCl₂(PPh₃)₂ (38 mg, 10 mol %). The mixture was stirred under nitrogen at 80° C. for 6 h. The DMF was removed at high vacuum and the residue was partially dissolved in EtOAc and filtered. The filtrate was concentrated in vacuo and the product was purified by flash chromatography eluting with hex/EtOAc (17.5:1) to afford 116 mg (62%) of the titled compound, Rf=0.31 (10:1 hex/EtOAc).

¹H NMR (200 MHz, CDCl₃) d 0.35 (s, 9H), 0.98 (s, 9H), 2.39 (s, 3H), 4.11 (bs, 1H), 7.12 (s, 1H), 7.26 (d, 2H), 7.50 (d, 2H).

Step C: Preparation of 3-(4-Bromomethylphenyl)-2-t-butylsulfonamido-5-trimethylsilylthiophene. (scheme II-5, compound 5c, Y=S)

To a solution of the product of Step B (207 mg, 0.542 mmol) in dry CCl₄ (3 ml), heated to dissolve the reagent, was added NBS (116 mg, 0.651 mmol) and a catalytic amount of AIBN. The reaction was refluxed (110° C.) for 3 h then cooled to rt and the insoluable succinimide was removed by filtration. The solvent was diluted with Et₂O/EtOAc and washed with water (2×) and brine, dried over MgSO₄ and filtered. The solvent was removed and the crude titled product product (250 mg) dried thoroughly overnight.

Step D: Preparation of 2-Butyl-6-methyl-3-[[4-[2-(N-tbutylsulfonamido)-3-thienyl]phenyl]methyl]quinazolin-4(3H)-one [compound 9b, (scheme II-9) where X¹—X²—X³—X⁴=—CH—CH—S—CZ— and Z=SO₂NHtBu] and 2-butyl-6-methyl-3-[[4-[5-trimethylsilyl-2-(N-butylsulfonamido)-3-thienyl]phenyl]methyl]quinazolin-4(3H)-one [compound 9a, (scheme II-9) where X¹—X²—X³—X⁴=—CH—C(TMS)—S—CZ— and Z=SO₂NHtBu]

To a solution of 2-butyl-6-methylquinazolin-4(1)-one, the product of Example 1, in dry DMF under N₂ is added NaH. The reaction is allowed to stir for 30 min. To this is added a solutio nfo the product of step C in dry DMF. After 3 h th ereaction was quenched with sat'd NH₄Cl solution. The DMF was replaced with EtOAc, dried over MgSO₄ and the insoluable salts removed by filtration. The products were purified by flash chromatography on a silica column isolating two products: one where $X^1-X^2-X^3-X^4=$—CH—C(TMS)—S—CZ— and $Z=SO_2NHtBu$ and the other where $X^1-X^2-X^3-X^4=$—CH—CH—S—CZ— and $=SO_2NHtBu$.

Step E: Preparation of 2-butyl-6-methyl-3-[[4-[2-(N-benzoylsulfonamido)-3-thienyl]phenyl]methyl]quinazolin-4(3H)-one (Compound 12 of Table VII) [compound 9b, (scheme II-9) where $X^1-X^2-X^3-X^4=$—CH—CH—S—CZ— and $Z=SO_2NHCOPh$] and 2-butyl-6-methyl-3-[[4-[5-trimethylsilyl-2-(N-benzoylsulfonamido)-3-thienyl]methyl]quinazolin-4(3H)-one [compound 9a, (scheme II-9) where $X^1-X^2-X^3-X^4=$—CH—C(TMS—S—CZ— and $Z=SO_2NHCOPh$]

Part 1: To the dry product (containing a the TMS group) of Step D was added a catalytic amount of anisole and TFA (2 ml) and the reaction is allowed to stir overnight. The next day when the TFA was removed the reaction became a deep red color. The two products, with and without the TMS group present, were free based by eluting through silica column using $CHCl_3/MeOH/NH_4OH$ eluant. The two products can be difficult to separate. The mixture can be used in the following step.

Part 2: To the mixture obtained in part 1 (crude) in dry pyridine is added benzoylchloride and a catalytic amount of DMAP.

After about 2 h the sides of the flask can be rinsed with additional pyridine and the reaction is allowed to stir another 30 min. The reaction is concentrated then diluted with $CH_2Cl_2$ and washed with 10% citric acid (2×) and water, dried over $MgSO_4$, filtered and the solvent removed. The products can be purified by flash chromatography on a silica column or HPLC.

EXAMPLE 26

2-Butyl-6-methyl-3-[[4-[3-(N-benzoylsulfonamido)-2-thienyl]phenyl]methyl]quinazolin-4-(3H)-one (Compound 11 of Table VII) [compound 9b, scheme II-9, where $X^1-X^2-X^3X^4=$—S—CH—CH—CZ— and $Z=SO_2NHCOPh$]

Step A: Preparation of 2,5-dibromo-3-t-butylsulfonamidothiophene (scheme II-7, compound 7b, Y=S)

To chlorosulfonic acid (4.5 mL) was added 2,5-dibromothiophene (0.505 g, 2.09 mmol) by syringe. On mixing the reaction turned dark orange-brown. After 10 min the reaction was poured very carefully over ice (100 ml). The solution turned bright yellow. The product was extracted from the water layer using EtOAc/$Et_2O$ (3×). The combined organic layers were washed with water and brine, dried over $MgSO_4$ and filtered. The solvent was replaced with dry $CH_2Cl_2$ (4.5 ml) and t-butylamine (0.659 mL, 6.27 mmol) was added. The reaction was stirred overnight. The next day the reaction was diluted with more $CH_2Cl_2$ and washed with 1N HCl (3×), dried over $MgSO_4$ and filtered. The product was purified by flash chromatography on a silica column eluting with Hex/EtOAc (20:1) to afford 470 mg (60%) of the titled compound, Rf=0.16 (10:1Hex/EtOAc).

$^1H$ NMR (400 MHz, $CDCl_3$) $\delta 1.25$ (s, 9H), 4.75 (s, 1H), 7.30 (s, 1H).

FAB mass spectrum, m/e 378 (M+1, calcd for $C_4H_{11}S_2O_2NBr_2$; 378).

Step B: Preparation of 3-t-butylsulfonamidothiophene (scheme II-7, compound 7c, Y=S)

To a solution of the product of Step A (1.70 g, 4.52 mmol) in 24% by volume glacial acetic acid/water (5 mL) was added Zn dust (1.73 g, 26.6 mmol). The mixture was refluxed (120° C.) overnight. The next day the reaction was cooled, diluted with EtOAc and filtered. $Et_2O$/EtOAc was added and the solution washed with 6N HCl (3×), water, carefully with 5% $NaHCO_3$ (2×) and brine. The solution was dried over $MgSO_4$ and filtered. The solvent was removed to afford 851 mg (86%) of the titled compound, Rf=0.23 (10:1 Hex/EtOAc).

$^1H$ NMR (200 MHz, $CDCl_3$) $\delta 1.25$ (s, 9H), 4.42 (s, 1H), 7.31-7.40 (m, 2H), 7.92-7.95 (dd, 1H).

Step C: Preparation of 2-bromo-3-t-butylsulfonamidothiophene (scheme II-7, compound 7d, Y=S)

To a solution of the product of Step B (230 mg, 1.05 mmol) in dry THF (5 mL) cooled to −78° C. in a dry ice/acetone bath under $N_2$ was added 1.6M n-butyllithium (3.28 ml, 5.25 mmol) dropwise. The reaction was warmed to −50° C. then cooled back to −78° C. and $Br_2$ (269 ml, 5.24 mmol) was added. The bath was removed and the reaction was warmed to rt. The reaction was quenched with sat'd $NH_4Cl$ solution. The solvent was replaced with $Et_2O$/EtOAc and the reaction solution washed with water, 1N NaOH, and brine. The solution was dried over $MgSO_4$, filtered and the solvent removed to afford 298 mg (95%) of the titled compound, Rf=0.53 (2:1 Hex/EtOAc).

$^1H$ NMR (400 MHz, $CDCl_3$) $\delta 1.22$ (s, 9H), 4.89 (s, 1H), 7.24 (d, 1H), 7.31 (d, 1H).

Step D: Preparation of 2-p-tolyl-3-t-butylsulfonamidothiophene (scheme II-7, compound 7e, Y=S)

To solution of the product of Step C (4.59 mmol, crude) in dry DMF (1 mL) was added p-tolyltrimethyltin (1.77 g, 6.95 mmol) and a catalytic amount of $Pd(PPh_3)_2Cl_2$ (325 mg, 0.463 mmol). The reaction was heated at 75°-80° C. for 5 h. The reaction was cooled to rt and the solvent replaced with EtOAc and filtered. The product was purified by flash chromatography on a silica column eluting with a gradient of Hex/EtOAc (25:1-15:1) to afford 1.01 g (71%) of the titled compound, Rf=0.49 (3:1 Hex/EtOAc).

$^1H$ NMR (200 MHz, $CDCl_3$) $\delta 0.98$ (s, 9H), 2.40 (s, 3H), 4.01 (s, 1H), 7.24 (d, 1H), 7.26 (d, 1H), 7.48 (d, 2H), 7.54 (d, 2H); FAB mass spectrum, m/e 310 (M+1, calcd for $C_{15}H_{19}S_2O_2N$, 310)

Step E: Preparation of 2-(4-bromomethylphenyl)-3-t-butylsulfonamidothiophene (scheme II-7, compound 7f, Y=S)

To a solution of the product of Step D (201 mg, 0.651 mmol) under $N_2$ in dry $CCl_4$ (2.5 mL) was added NBS (130 mg, 0.730 mmol) and a catalytic amount of AIBN. The reaction mixture was brought to reflux (110° C.). After 5 h the reaction was cooled to rt and the insoluable succinimide was removed by filtration. The solvent was replaced with $Et_2O$/EtOAc and washed with water (2×) and brine, dried over $MgSO_4$ and filtered.

The solvent was removed and the crude reaction product dried thoroughly under vacuum.

Step F: Preparation of 2-Butyl-6-methyl-3-[[4-[3-(N-t-butylsulfonamido)-2-thienyl]phenyl]methyl]quinazolin-4(3H)-one [compound 9b, scheme II-9, where $X^1$—$X^2$—$X^3X^4$=—S—CH—CH—CZ—Z=$SO_2$NHtBu]

To a solution of 2-butyl-6-methylquinazolin-4(1H)-one, the product of Example 1, in dry DMF under $N_2$ is added NaH. The reaction is allowed to stir for 30 min. To this is added a solution of the product of Step E (crude) in dry DMF. After about 5 h the reaction is quenched with sat'd $NH_4Cl$ solution. The DMF is replaced with $Et_2O$/EtOAc, dried over $MgSO_4$ and the insoluable salts removed by filtration. The product was purified by flash chromatography on a silica column.

Step G: Preparation of 2-Butyl-6-methyl-3-[[4-[3-(N-t-benzoylsulfonamido)-2-thienyl]phenyl]methyl]quinazolin-4(3H)-one [compound 9b, scheme II-9, where $X^1$—$X^2$—$X^3X^4$=—S—CH—CH—CZ—Z=$SO_2$NHCOPh Part 1: To dry product of Step F is added anisole (2 drops) and TFA and the reaction is allowed to stir overnight. The next day the TFA is removed and the reaction became a deep red color. The product can be purified by flash chromatography on a silica column. Removal of the solvent affords the primary sulfonamide.

Part 2: Acylation with benzoylchloride was carried out following the procedure used in part 2, Step E of Example 25.

EXAMPLE 27

5-Butyl-2-(2-chlorophenyl)-4-[[4-[3-(N-benzoylsulfonamido)-2-thienyl]phenyl]methyl]-2,4-dihydro-3H-1,2,4-triazol-3-one (Compound 20 of Table V)

Step A: A preparation of 5-butyl-2-(2-chlorophenyl)-4-[[4-[3-(N-t-butylsulfonamido)-2-thienyl]phenyl]methyl]-2,4-dihydro-3H-1,2,4-triazol-3-one To a solution of 5-butyl-2-(2-chlorophenyl)-2,4-dihydro-3H-1,2,4-triazol-3-one the product of Example 17, (101 mg, 0.400 mmol) in dry DMF (1 mL) under $N_2$ was added NaH (16.0 mg, 0.400 mmol). The reaction was allowed to stir for 30 min. The reaction turned pink in color. To this was added a solution of the product of Example 26, Step E (0.415 mmol, crude) in dry DMF (1.5 mL). After 5 h the reaction was quenched with sat'd $NH_4Cl$ solution. The DMF was replaced with EtOAc, dried over $MgSO_4$ and the insoluable salts removed by filtration. The product was purified by flash chromatography on a silica column using Hex/EtOAc (2:1) to afford 120 mg (52% 2 steps) of the desired product, Rf=0.29 (2:1EtOAc/Hex). FAB mass spectrum, m/e 559.3 (M+1, calcd for $C_{27}H_{31}S_2O_3N_4Cl$ 559.5).

$^1H$ NMR (400 MHz, $CD_3OD$) δ0.89 (t, 3H), 1.00 (s, 9H), 1.35–1.41 (sextet, 2H), 1.58–1.62 (quintet, 2H), 2.58 (t, 2H), 5.05 (s, 2H), 7.39–7.66 (m, 10 H).

Step B: Preparation of 5-butyl-2-(2-chlorophenyl)-4-[[4-[3-sulfonamido-2-thienyl]phenyl]methyl]-2,4-dihydro-1,2,4-triazol-3-one To the dry product of Step A (60 mg, 0.11 mmol) was added anisole (2 drops) and TFA (2 mL) and the reaction was allowed to stir over two days. The reaction became a deep red color. The TFA was removed and the product was free based by eluting through a silica column using $CHCl_3$/MeOH/$NH_4OH$ (80:10:1) to afford 48.2 mg (87%) of the desired product as a white solid, Rf=0.70 (40:10:1 $CHCl_3$/MeOH/$NH_4OH$).

Step C: Preparation of 5-butyl-2-(2-chlorophenyl)-4-[[4-[3-(N-benzoylsulfonamido-2-thienyl]phenyl]methyl]-2,4-dihydro-1,2,4-triazol-3-one To the product of Step B (21.0 mg, 0.042 mmol) in dry pyridine (0.5 mL) was added benzoylchloride (50 μL, 0.43 mmol) and a catalytic amount of DMAP. After 1.5 h the sides of the flask were rinsed with additional pyridine (1 mL) and the reaction allowed to stir another 30 min. The reaction was concentrated then diluted with $CH_2Cl_2$ and washed with 10% citric acid (2×) and water, dried over $MgSO_4$, filtered and the solvent removed. The product was purified by flash chromatography on a silica column using $CHCl_3$/MeOH/$NH_4OH$ (80:10:1). Purification yielded 21.2 mg (83%) of the titled compound, Rf=0.39 (40:10:1 $CHCl_3$/MeOH/$NH_4OH$). FAB mass spectrum, m/e 629.6 (M+Na, calcd for $C_{30}H_{27}S_2O_4$ OH). FAB mass spectrum, m/e 629.6 (M+Na, calcd for $C_{30}H_{27}S_2O_4N_4Cl$ 629.5).

$^1H$ NMR (400 MHz, $CDCl_3$) δ0.88 (t, 3H), 1.35–1.40 (sextet, 2H), 1.59–1.64 (quintet, 2H), 2.56 (t, 2H), 5.02 (s, 2H), 7.33–7.63 (m, 15H).

EXAMPLE 28

2-(2-chlorophenyl)-5-butyl-4-[[4-[3-N-cyclopropane carbonylsulfonamido-2-thienyl]phenyl]methyl]-2,4-dihydro-1,2,4-triazol-3-one To the product of Example 27, Step B (20.8 mg, 0.041 mmol) in dry pyridine (0.5 mL) was added cyclopropane carbonyl chloride (38 μL, 0.41 mmol) and a catalytic amount of DMAP. After 3 h in the sides of the flask were rinsed with additional pyridine (1 mL) and the reaction allowed to stir another 2 h. The reaction was diluted with $CH_2Cl_2$ and washed with 10% citric acid (2×) and water, dried over $MgSO_4$, filtered and the solvent removed. The product was purified by flash chromatography on a silica column using $CHCl_3$/MeOH/$NH_4OH$ (80:10:1). Purification yielded 16.5 mg (71%) of the titled compound, Rf=0.52 (40:10:1 ($CHCl_3$/MeOH/$NH_4OH$). FAB mass spectrum, m/e 571.3 (M+1, clacd for $C_{27}H_{27}S_2O_4N_4Cl$ 571.5).

$^1H$ NMR (400 MHz, $CD_3OD$) δ0.68–0.75 (m, 4H), 0.89 (t, 3H), 1.34–1.41 (m, 3H), 1.58–1.63 (m, 2H), 2.60 (quintet, 2H), 5.05 (s, 2H), 7.39 (d, 2H), 7.46–7.63 (m, 8H).

EXAMPLE 29

A representative procedure for the preparation of compounds of Structure 11-d, Scheme II-11

Step 1: Preparation of 2-pentyl-5-(t-butylsulfonamido)thiophene (scheme II-11, compound 11a, $R^{12}=(CH_2)_4CH_3$)

To a solution of 2-(t-butylsulfonamido)thiophene (3.42 g, 15.6 mmol) in anhydrous THF cooled to −78° C. under $N_2$ was added 2.5M n-BuLi (15.6 mL, 2.5 equiv). The reaction was warmed to −20° C. over 3.5 h. After stirring at −20° C. for an addional h, iodopentane (2.4 mL, 1.2 equiv) was added. The ice bath was removed and the reaction was stirred at rt overnight. The next day the reaction was quenched with sat'd $NH_4Cl$ solution and the THF was removed in vacuo. The residue was extracted with $Et_2O$/EtOAc and washed with water and brine. The organic was dried over anhydrous $MgSO_4$ and concentrated in vacuo. The product was purified by flash chromatography on a silica column eluting with Hex/EtOAc (15:1). Removal of the solvent afforded 2.72 g (60%) of the titled compound as a yellow oil. Rf=0.4 (6:1 Hex/EtOAc).

$^1H$ NMR (200 MHz, $CDCl_3$) δ0.91 (t, 3H), 1.28 (s, 9H), 1.33 (m, 4H), 1.68 (bt, 2H), 2.81 (t, 2H), 4.63 (s, 1H), 6.69 (d, 1H), 7.41 (d, 1H).

The following table lists additional compounds (11a, scheme II-11) prepared using the procedure described above. Any variation from the above procedure is noted in the comment column.

| | | Compounds 11a, Scheme II-11 | | |
|---|---|---|---|---|
| $R^{12}$ | $R^{12}X$ | % Yield | Rf (solvent) | Comments |
| $CH_3$ | $ICH_3$ | 49 | 0.44 (3:1 Hex/EtOAc) | *, white solid, † |
| $CH_2CH_3$ | $ICH_2CH_3$ | 84 | 0.47 (3:1 Hex/EtOAc) | *, oil |
| $(CH_2)_2CH_3$ | $I(CH_2)_2CH_3$ | 65 | 0.52 (2:1 Hex/EtOAc) | *, oil |
| $(CH_2)_3CH_3$ | $I(CH_2)_3CH_3$ | 62 | 0.32 (6:1 Hex/EtOAc) | *, yellow oil, @ |
| $CH_2CH(CH_3)_2$ | $ICH_2CH(CH_3)_2$ | 44 | 0.37 (6:1 Hex/EtOAc) | *, yellow oil, # |
| $(CH_2)_4CH_3$ | $I(CH_2)_4CH_3$ | 60 | 0.40 (6:1 Hex/EtOAc) | *, yellow oil |
| $CH_2Ph$ | $BrCH_2Ph$ | ~70 | 0.49 (3:1 Hex/EtOAc) | taken on crude |
| $Si(CH_3)_3$ | $ClSi(CH_3)_3$ | 60 | 0.36 (6:1 Hex/EtOAc) | *, solid, @ |

* The high field NMR spectrum and FAB mass spectrum are consistant with the structure assigned.
Yield is based on recovered starting material.
@ A 1.5 M LDA solution was substituted for N-BuLi.
† MPLC purification was necessary.

Step 2: Preparation of boronic acid derivative 11b (scheme II-11, compound 11b, $R^{12}=(CH_2)_4CH_3$)

To a solution of 2-pentyl-5-(t-butylsulfonamido)thiophene (2.50 g, 8.65 mmol) in anhydrous THF (15 mL) cooled to −78° C. was added 2.5M n-BuLi (8.7 mL, 2.5 equiv). The mixture was allowed to warm to rt over 4 h and stirred for an additional 30 min. The mixture was cooled back to −60° C. and triisopropyl borate (3.0 mL, 1.5 equiv) was added. The ice bath was removed and the mixture was stirred overnight at rt. The next day the reaction was quenched with 2N HCL (3 mL) and the resulting mixture was stirred for 30 min. The THF was removed under reduced pressure and the residue was taken up into EtOAc. The organic was washed with $H_2O$ and brine and dried over $MgSO_4$. Removal of the solvent afforded 3.2 g (crude) of the titled compound as a thick yellow oil.

Step 3: Preparation of 4-[(4-hydroxymethyl)phenyl]-2-pentyl-5-(t-butylsulfonamido)thiophene (scheme II-11, compound 11c, $R^{12}=(CH_2)_4CH_3$)

To a solution of the product from step A (3.2 g, crude) in toluene (60 mL) and 1N NaOH (17 ml) was added 4-bromobenzyl alcohol (4.85 g, 3 equiv) in EtOH (15 mL). To this mixture was added $Pd(PPh_3)_4$ (300 mg, 3 mol %). The reaction was stirred at reflux under $N_2$ for 4 h. The mixture was cooled to rt and extracted with $Et_2O$/EtOAc. The organic was washed with $H_2O$ and brine, dried over anhydrous $MgSO_4$ and concentrated in vacuo. The product was purified by flash chromatography on a silica column eluting with Hex/EtOAc (2:1). Removal of the solvent afforded 1.97 g (58%) of the titled compound as a slightly yellow solid. Rf=0.24 (2:1 Hex/EtOAc).

$^1H$ NMR (200 MHz, $CDCl_3$) δ0.91 (t, 3H), 1.01 (s, 9H), 1.35 (m, 4H), 1.67 (bm, 3H), 2.82 (t, 2H), 4.13 (s, 1H), 4.75 (s, 2H), 6.77 (s, 1H), 7.44 (d, 2H), 7.60 (d, 2H).

Step 4: Preparation of 4-[4-bromomethyl)phenyl]-2-pentyl-5-(t-butylsulfonamido)thiophene (scheme II-11, compound 11d, $R^{12}=(CH_2)_4CH_3$)

To a solution of the product of step B (493 mg, 1.25 mmol) in anhydrous $CCl_4$ (4 mL) and $CH_2Cl_2$ (4 mL) was added $PBr_3$ (0.078 mL, 0.66 equiv). After stirring at rt for 1 h the solvent was removed under reduced pressure and the residue was stripped down fom $CCl_4$ several times to remove any residual HBr. The product was purified by flash chromatography on a silica column eluting with Hex/EtOAc (2:1). Removal of the solvent afforded 473 mg (83%) of the titled compound as a slightly yellow solid. Rf=0.72 (2:1 Hex/EtOAc).

$^1H$ NMR (200 MHz, $CDCl_3$) δ0.90 (t, 3H), 0.99 (s, 9H), 1.35 (m, 4H), 1.71 (m, 2H), 2.81 (t, 2H), 4.05 (s, 1H), 4.52 (s, 2H), 6.77 (s, 1H), 7.45 (d, 2H), 7.59 (d, 2H).

The following table lists additional compounds (11d, scheme II-11) prepared using the procedure described above. Any variation from the above procedure is noted in the comment column.

| | Compounds 11d, Scheme II-11 | | |
|---|---|---|---|
| $R^{12}$ | Pd Coupling Yield | Rf (solvent) | Comments |
| $CH_3$ | 27 | 0.67 (2:1 Hex/EtOAc) | *, #, white solid |
| $CH_2CH_3$ | 23 | 0.70 (2:1 Hex/EtOAc) | taken on crude |
| $(CH_2)_2CH_3$ | 52 | 0.44 (1:1 Hex/EtOAc) | *, yellowish solid |

-continued

Compounds 11d, Scheme II-11

| R[12] | Pd Coupling Yield | Rf (solvent) | Comments |
|---|---|---|---|
| $(CH_2)_3CH_3$ | 30 | 0.73 (2:1 Hex/EtOAc) | *, #, yellowish solid |
| $CH_2CH(CH_3)_2$ | 28 | 0.25 (2:1 Hex/EtOAc 2×'s) | *, #, yellowish solid |
| $(CH_2)_4CH_3$ | 58 | 0.40 (6:1 Hex/EtOAc) | *, yellowish solid |
| $CH_2Ph$ | 25 | 0.54 (3:1 Hex/EtOAc) | *, #, white solid |
| $Si(CH_3)_3$ | 36 | 0.45 (6:1 Hex/EtOAc) | *, @, white solid |

\* The high field NMR spectrum and FAB mass spectrum are consistant with the structure assigned.
\# The palladium catalyzed coupling was done using anhydrous DMF as solvent with $NEt_3$ as base.
@ 4-bromotoluene was substituted for 4-bromobenzyl alcohol in the palladium coupling (step B) and NBS bromination was used to prepare the corresponding bromide.

EXAMPLE 30

5-butyl-2-(2-trifluoromethylphenyl)-3-[[4-[2-(N-benzoylsulfonamido)-5-methyl-3-thienyl]phenyl]methyl]-2,4-dihydro-3H-1,2,4-triazol-3-one (Compound 28 of Table V)

The titled compound was prepared from compound 11d ($R^{12}=CH_3$) substituting 5-butyl-2-(2-trifluoromethylphenyl)-2,4-dihydro-3H-1,2,4-triazol-3-one for 5-butyl-2-(2-chlorophenyl)-2,4-dihydro-3H-1,2,4-triazol-3-one and using the procedure described in Steps A through C of Example 27.

$^1$H NMR (400 MHz, $CD_3OD$) δ0.87 (t, 3H), 1.32 (q, 2H), 1.59 (m, 2H), 2.51 (s, 3H), 2.52 (t, 2H), 4.61 (s, 1H), 4.94 (s, 2H), 6.82 (s, 1H), 7.23 (d, 2H), 7.29 (d, 2H), 7.41 (m, 1H), 7.56–7.67 (comp m, 5H), 7.70 (t, 1H), 7.81 (t, 1H), 7.89 (d, 1H).

EXAMPLE 31

5-butyl-2-(2-trifluoromethylphenyl)-3-[[4-[2-(N-benzoylsulfonamido)-5-ethyl-3-thienyl]phenyl]methyl]-2,4-dihydro-3H-1,2,4-triazol-3-one (Compound 29 of Table V)

The titled compound was prepared from compound 11d ($R^{12}=CH_2CH_3$) using the procedure described in Example 30.

$^1$H NMR (400 MHz, $CDCl_3$) δ0.80 (t, 3H), 1.22 (q, 2H), 1.24 (t, 3H), 1.51 (t, 2H), 2.31 (t, 2H), 2.65 (q, 2H), 4.68 (s, 2H), 6.63 (s, 1H), 7.03 (bd, 2H), 7.16 (bd, 2H), 7.32 (m, 2H), 7.38–7.51 (comp m, 4H), 7.61 (d, 1H), 7.71 (bs, 1H).

EXAMPLE 32

5-butyl-2-(2-trifluoromethylphenyl)-3-[[4-[2-(N-benzoylsulfonamido)-5-propyl-3-thienyl]phenyl]methyl]-2,4-dihydro-3H-1,2,4-triazol-3-one (Compound 30 of Table V)

The titled compound was prepared from compound 11d ($R^{12}=(CH_2)_2CH_3$) using the procedure described in Example 30.

$^1$H NMR (400 MHz, $CD_3OD$) δ0.86 (t, 3H), 0.98 (q, 3H), 1.33 (m, 2H), 1.61 (m, 2H), 1.68 (m, 2H), 2.52 (t, 2H), 2.78 (t, 2H), 4.95 (s, 2H), 6.82 (s, 1H), 7.22 (d, 4H), 7.38–7.61 (comp m, 5H), 7.72 (dd, 4H).

EXAMPLE 33

5-butyl-2-(2-trifluoromethylphenyl)-3-[[4-[2-(N-benzoylsulfonamido)-5-n-butyl-3-thienyl]phenyl]methyl]-2,4-dihydro-3H-1,2,4-triazol-3-one (Compound 31 of Table V)

The titled compound was prepared from compound 11d ($R^{12}=(CH_2)_3CH_3$) using the procedure described in Example 30.

$^1$H NMR (400 MHz, $CD_3OD$) δ0.87 (t, 3H), 0.96 (t, 3H), 1.32–1.81 (comp m, 8H), 2.51 (t, 2H), 2.88 (t, 2H), 5.01 (s, 2H), 6.87 (s, 1H), 7.23 (d, 2H), 7.31 (d, 2H), 7.48 (d, 2H), 7.58 (bd, 4H), 7.70–7.82 (comp m, 2H), 7.88 (d, 1H).

EXAMPLE 34

5-butyl-2-(2-trifluoromethylphenyl)-3-[[4-[2-(N-benzoylsulfonamido)-5-isobutyl-3-thienyl]phenyl]methyl]-2,4-dihydro-3H-1,2,4-triazol-3-one (Compound 33 of Table V)

The titled compound was prepared from compound 11d ($R^{12}=CH_2CH(CH_3)_2$) using the procedure described in Example 30.

$^1$H NMR (400 MHz, $CD_3OD$) δ0.87 (t, 3H), 1.00 (d, 6H), 1.30 (m, 2H), 1.59 (m, 2H), 1.96 (m, 2H), 2.52 (t, 2H), 2.73 (d, 2H), 5.00 (s, 2H), 6.86 (s, 1H), 7.27 (d, 2H), 7.33 (d, 2H), 7.47 (d, 3H), 7.58 (bd, 3H), 7.70–7.82 (comp m, 2H), 7.91 (d, 1H).

EXAMPLE 35

5-butyl-2-(2-trifluoromethylphenyl)-3-[[4-[2-(N-benzoylsulfonamido)-5-pentyl-3-thienyl]phenyl]methyl]-2,4-dihydro-3H-1,2,4-triazol-3-one (Compound 32 of Table V)

The titled compound was prepared from compound 11d ($R^{12}=(CH_2)_4CH_3$) using the procedure described in Example 30.

$^1$H NMR (200 MHz, $CD_3OD$) δ0.82–0.95 (comp m, 6H), 1.21–1.51 (comp m, 4H), 1.61 (m, 2H), 1.71 (m, 2H), 2.52 (t, 2H), 2.87 (t, 2H), 4.99 (s, 2H), 6.87 (s, 1H), 7.27 (d, 2H), 7.38 (d, 2H), 7.47 (d, 2H), 7.57 (bd, 4H), 7.70–7.82 (comp m, 2H), 7.89 (d, 1H).

EXAMPLE 36

2-propyl-6-(3-N-ethylurea)-3-[[4-[2-(N-butyloxycarbonylsulfonamido)-5-propyl-3-thienyl]phenyl]methyl]-quinazolin-4-(3H)-one (Compound 46 of Table VII)

The titled compound was prepared from compound 18c of scheme II-18 where $—X^1—X^2—X^3—X^4—$ is $—CH=CR^{12}—S—CZ=$, $Z=SO_2NH_2$, $R^{12}=$propyl and $R^{21}$ is Et. To a solution of 18c (32 mg, 0.056 mmol) in dry pyridine (1.0 mL) was added n-butyl chloroformate (0.1 mL, 0.78 mmol) at rt. After stirring at rt overnight, the mixture was diluted with 1N HCl and extracted with ethyl acetate. The organic extract was dried over anhydrous $Na_2SO_4$, evaporated in vacuo and the residue was purified by silica gel chromatotron plate ($CH_2Cl_2$/MeOH 40:1) to afford 38 mg (100%) of the titled compound as a colorless glass.

$^1$H NMR (200 MHz, $CD_3OD$) δ0.62 (t, 3H), 0.72–0.93 (comp m, 6H), 0.95 (t, 3H), 1.03 (m, 2H), 1.22 (m, 2H), 1.45–1.68 (comp m, 4H), 2.57 (q, 4H), 3.03 (q, 2H), 3.73 (t, 2H), 5.21 (s, 2H), 6.55 (s, 1H), 6.96 (d, 2H), 7.22 (d, 2H), 7.39 (l, 1H), 7.81 (s, 2H).

EXAMPLE 37

2-propyl-6-(N-benzamido)-3-[[4-[2-N-cyclopropylcarbonylsulfonamido)-5-isobutyl-3-thienyl]phenyl]methyl]quinazolin-4-(3H)-one (Compound 42 of Table VII)

The titled compound was prepared using the methodology described in scheme II-17 from compound 17e where $-X^1-X^2-X^3-X^4-$ is $-CH=CR^{12}-S-CZ=$, $Z=SO_2NH_2$, $R^{12}=$isobutyl and $R^{21}$ is Ph.

$^1$H NMR (200 MHz, CDCl$_3$) δ0.62–0.72 (m, 2H), 0.85–1.08 (comp m, 11H), 1.55–1.98 (m, 4H), 2.56 (t, 2H), 2.67 (d, 2H), 4.97 (s, 2H), 6.68 (s, 1H), 6.87 (d, 2H), 7.56–7.71 (comp m, 5H), 7.69 (d, 1H), 7.85 (d, 2H), 8.40 (d, 1H), 8.71 (dd, 1H), 9.61 (bs, 1H).

EXAMPLE 38

2-propyl-6-(N-benzamido)-3-[[4-[2-N-butyloxycarbonylsulfonamido)-5-isobutyl-3-thienyl]phenyl]methyl]quinazolin-4-(3H)-one (Compound 43 of Table VII)

The titled compound was prepared using the methodology described in scheme II-17 from compound 17e where $-X^1-X^2-X^3-X^4-$ is $-CH=CR^{12}-S-CZ=$, $Z=SO_2NH_2$, $R^{12}=$isobutyl and $R^{21}$ is Ph.

$^1$H NMR (200 MHz, CDCl$_3$) δ0.78–0.88 (comp m, 6H), 0.93 (d, 6H), 1.23 (m, 2H), 1.51 (m, 2H), 1.68 (m, 2H), 1.91 (m, 1H), 2.50 (t, 2H), 2.67 (d, 2H), 4.11 (t, 2H), 4.96 (s, 2H), 6.69 (s, 1H), 6.74 (d, 2H), 7.32 (d, 2H), 7.41–7.59 (comp m, 3H), 7.68 (d, 1H), 8.42 (d, 1H), 8.89 (dd, 1H), 9.61 (bs, 1H).

EXAMPLE 39

2-propyl-6-(3-N-ethylurea)-3-[[4-[2-(N-methoxyethoxycarbonylsulfonamido)-5-propyl-3-thienyl]phenyl]methyl]quinazolin-4-(3H)-one (Compound 48 of Table VII)

The titled compound was prepared from compound 18c of scheme II-18 where $-X^1-X^2-X^3-X^4-$ is $-CH=CR^{12}-S-CZ=$, $Z=SO_2NH_2$, $R^{12}=$propyl and $R^{21}$ is ethyl.

$^1$H NMR (200 MHz, CD$_3$OD) δ0.72–0.86 (comp m, 6H), 0.92 (t, 3H), 1.52 (m, 4H), 3.01 (q, 2H), 3.04 (s, 3H), 3.23 (t, 2H), 3.91 (t, 2H), 5.21 (s, 2H), 6.52 (s, 1H), 6.96 (d, 2H), 7.21 (d, 2H), 7.39 (l, 1H), 7.79 (s, 2H).

DEPROTECTION OF THE TRITYL GROUP ON THE TETRAZOLE RING

To a solution of of the trityl protected product in MeOH is added a catalytic amount of 2N HCl. After about an hour the solvent is removed and the product triturated with Et$_2$O to will afford the free tetrazole.

TABLE V

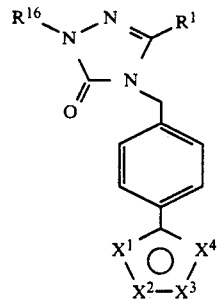

| # | R$^1$ | R$^{16}$ | $-X^1-X^2-X^3-X^4-$ | R$^{12}$ | Z |
|---|---|---|---|---|---|
| 1 | n-propyl | CH$_2$Ph | —CH—S—CH—CZ— | | 1H-tetrazol-5-yl |
| 2 | n-butyl | CH$_2$Ph | —CH—S—CH—CZ— | | 1H-tetrazol-5-yl |
| 3 | n-propyl | cyclopentyl | —CH—S—C(Br)—CZ— | | 1H-tetrazol-5-yl |
| 4 | n-butyl | n-butyl | —CH—S—C(Br)—CZ— | | 1H-tetrazol-5-yl |
| 5 | n-butyl | CO$_2$CH$_3$ | —CH—CH—O—CZ— | | 1H-tetrazol-5-yl |
| 6 | n-butyl | CH$_2$OH | —CH—CH—O—CZ— | | 1H-tetrazol-5-yl |
| 7 | n-butyl | 2-CO$_2$H-Ph | —CH—S—CH—CZ— | | SO$_2$NHCOPh |
| 8 | n-butyl | 2-Cl-Ph | —CH—S—CH—CZ— | | CO$_2$H |
| 9 | n-propyl | CO$_2$CH$_3$ | —CH—S—CH—CZ— | | 1H-tetrazol-5-yl |
| 10 | n-propyl | CH$_2$Ph | —CH—S—CH—CZ— | | SO$_2$NHCOPh |
| 11 | n-propyl | CH$_2$Ph | —CH—CH—S—CZ— | | 1H-tetrazol-5-yl |
| 12 | n-butyl | CH$_2$Ph | —CH—CH—S—CZ— | | 1H-tetrazol-5-yl |
| 13 | n-butyl | 2-CF$_3$-Ph | —CH—S—CH—CZ— | | SO$_2$NHCOPh |
| 14 | n-butyl | 2-CH$_3$-Ph | —CH—S—CH—CZ— | | SO$_2$NHCOPh |
| 15 | n-propyl | 2-Cl-Ph | —CH—S—CH—CZ— | | SO$_2$NHCOPh |
| 16 | n-propyl | CH$_2$Ph | —CH—CH—S—CZ— | | SO$_2$NHCOPh |
| 17 | n-butyl | CH$_2$Ph | —CH—CH—S—CZ— | | SO$_2$NHCOPh |
| 18 | n-propyl | 2-Cl-Ph | —CH—S—CH—CZ— | | SO$_2$NHCOPh |
| 19 | n-propyl | 2-Cl-Ph | —S—CH—CH—CZ— | | SO$_2$NHCOPh |
| 20 | n-butyl | 2-Cl-Ph | —S—CH—CH—CZ— | | SO$_2$NHCOPh |
| 21 | n-butyl | CH$_2$OH | —CH—S—C(SO$_2$NHCOPh)CZ | | SO$_2$NHCOPh |
| 22 | n-butyl | CH$_2$CH$_3$ | —CH—S—CH—CZ— | | 1H-tetrazol-5-yl |
| 23 | n-butyl | CH$_2$Ph | —C—C—S—CZ— with HC\\CH / HC=CH | | 1H-tetrazol-5-yl |

TABLE V-continued

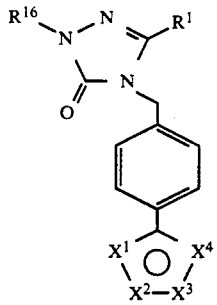

| # | R¹ | R¹⁶ | —X¹—X²—X³—X⁴— | R¹² | Z |
|---|---|---|---|---|---|
| 24 | n-butyl | 2-Cl-Ph | -C=C-S-CZ- fused benzo | | SO₂NHCOPh |
| 25 | n-propyl | 2-CF₃-Ph | -C=C-S-CZ- fused benzo | | SO₂NHCOPh |
| 26 | n-butyl | 2,6-diCl-Ph | -C=C-S-CZ- fused benzo | | SO₂NHCOPh |
| 27 | n-butyl | 2-Cl-Ph | S—CH—CH—CZ | | SO₂NHCO—cyclopropyl |
| 28 | n-butyl | 2-CF₃-Ph | —CH—CR¹²—S—CZ— | methyl | SO₂NHCOPh |
| 29 | n-butyl | 2-CF₃-Ph | —CH—CR¹²—S—CZ— | ethyl | SO₂NHCOPh |
| 30 | n-butyl | 2-CF₃-Ph | —CH—CR¹²—S—CZ— | n-propyl | SO₂NHCOPh |
| 31 | n-butyl | 2-CF₃-Ph | —CH—CR¹²—S—CZ— | n-butyl | SO₂NHCOPh |
| 32 | n-butyl | 2-CF₃-Ph | —CH—CR¹²—S—CZ— | n-pentyl | SO₂NHCOPh |
| 33 | n-butyl | 2-CF₃-Ph | —CH—CR¹²—S—CZ— | isobutyl | SO₂NHCOPh |
| 34 | n-butyl | 2-CF₃-Ph | —CH—CR¹²—S—CZ— | methyl | SO₂NHCOCH(Ph)₂ |
| 35 | n-butyl | 2-CF₃-Ph | —CH—CR¹²—S—CZ— | ethyl | SO₂NHCOCH(Ph)₂ |
| 36 | n-butyl | 2-CF₃-Ph | —CH—CR¹²—S—CZ— | n-propyl | SO₂NHCOCH₂OMe |
| 37 | n-butyl | 2-CF₃-Ph | —CH—CR¹²—S—CZ— | isobutyl | SO₂NHCO(3-Me-2-furyl) |
| 38 | n-butyl | 2-CF₃-Ph | —CH—CR¹²—S—CZ— | n-pentyl | SO₂NHCO(3-Me-2-furyl) |
| 39 | n-butyl | 2-CF₃-Ph | —CH—CR¹²—S—CZ— | n-propyl | SO₂NHCOtBu |
| 40 | n-butyl | 2-CF₃-Ph | —CH—CR¹²—S—CZ— | isobutyl | SO₂NHCOtBu |

TABLE VI

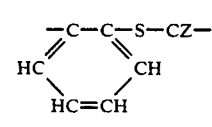

| # | R¹ | R¹⁷ | R¹⁸ | —X¹—X²—X³—X⁴— | R¹² | Z |
|---|---|---|---|---|---|---|
| 1 | n-butyl | CH₃ | H | —CH—S—CH—CZ— | | 1H-tetrazol-5-yl |
| 2 | n-butyl | CH₃ | H | —CH—S—CH—CZ— | | SO₂NHCOPh |
| 3 | n-propyl | 2-Cl-Ph | H | —CH—S—CH—CZ— | | SO₂NHCOPh |
| 4 | n-butyl | CH₃ | CH₃ | —CH—S—CH—CZ— | | SO₂NHCOPh |
| 5 | n-propyl | 2-CH₃-Ph | CH₃ | —CH—S—CH—CZ— | | 1H-tetrazol-5-yl |
| 6 | n-propyl | 2-CF₃-Ph | CH₃ | —CH—S—CH—CZ— | | 1H-tetrazol-5-yl |
| 7 | n-butyl | 2-CH₃-Ph | CH₃ | —CH—C(Si(CH₃)₃)—S—CZ— | | SO₂NHCOPh |

TABLE VI-continued

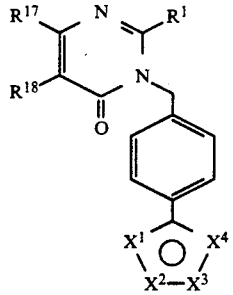

| # | R[1] | R[17] | R[18] | —X[1]—X[2]—X[3]—X[4]— | R[12] | Z |
|---|---|---|---|---|---|---|
| 8 | n-propyl | CH$_3$ | CH$_3$ | =C—C=S—CZ—, HC(–CH=CH–)CH | | SO$_2$NHCOPh |
| 9 | n-butyl | 2-Cl-Ph | | =C—C=S—CZ—, HC(–CH=CH–)CH | | SO$_2$NHCOPh |
| 10 | n-propyl | CH$_3$ | CH$_3$ | —CH—CH—S—CZ— | | SO$_2$NHCOPh |
| 11 | n-propyl | CH$_3$ | CO$_2$H | —CH—CH—S—CZ— | | SO$_2$NHCOPh |
| 12 | n-butyl | CH$_3$ | CH$_3$ | —S—CH—CH—CZ— | | 1H-tetrazol-5-yl |
| 13 | n-butyl | CH$_3$ | CO$_2$H | —S—CH—CH—CZ— | | 1H-tetrazol-5-yl |
| 14 | n-butyl | 2-Cl-Ph | CH$_3$ | —S—CH—CH—CZ— | | SO$_2$NHCOPh |
| 15 | n-propyl | 2-CH$_3$-Ph | CH$_3$ | —S—CH—CH—CZ— | | SO$_2$NHCOPh |
| 16 | n-butyl | CH$_3$ | 2-CH$_3$-Ph | —CH—S—C(SO$_2$NHCOPh)-CZ— | | H |
| 17 | n-propyl | CH$_3$ | Cl | —CH—S—CH—CZ— | | 1H-tetrazol-5-yl |
| 18 | n-butyl | CH$_3$ | 2-CH$_3$-Ph | —CH—S—CH—CZ— | | 1H-tetrazol-5-yl |
| 19 | n-propyl | CH$_3$ | 2-Cl-Ph | —CH—S—C(Br)—CZ— | | 1H-tetrazol-5-yl |
| 20 | n-propyl | CH$_3$ | CH$_2$-Ph | —CH—S—C(Br)—CZ— | | 1H-tetrazol-5-yl |
| 21 | n-propyl | CH$_3$ | 2-Cl-Ph | —CH—CH—S—CZ— | | 1H-tetrazol-5-yl |
| 22 | n-propyl | CH$_3$ | CH$_2$-Ph | —CH—CH—S—CZ— | | 1H-tetrazol-5-yl |
| 23 | n-butyl | CH$_3$ | 2-Cl-Ph | —CH—CH—O—CZ— | | 1H-tetrazol-5-yl |
| 24 | n-butyl | CH$_3$ | CH$_2$-Ph | —CH—CH—O—CZ— | | 1H-tetrazol-5-yl |
| 25 | n-propyl | CH$_3$ | 2-Cl-Ph | =C—C=S—CZ—, HC(–CH=CH–)CH | | SO$_2$NHCOPh |
| 26 | n-butyl | CH$_3$ | 2-CF$_3$-Ph | =C—C=S—CZ—, HC(–CH=CH–)CH | | SO$_2$NHCOPh |
| 27 | n-butyl | CH$_3$ | CH$_2$-Ph | —CH—CH—S—CZ— | | SO$_2$NHCOPh |
| 28 | n-butyl | CH$_3$ | 2-CH$_3$-Ph | —CH—CH—S—CZ— | | SO$_2$NHCOPh |
| 29 | n-butyl | CH$_3$ | 2-Cl-Ph | —S—CH—CH—CZ— | | SO$_2$NHCOPh |
| 30 | n-butyl | CH$_3$ | 2-CF$_3$-Ph | —S—CH—CH—CZ— | | SO$_2$NHCOPh |
| 31 | n-butyl | CH$_3$ | 2-CF$_3$-Ph | —CH—CR[12]—S—CZ— | n-propyl | SO$_2$NHCOPh |
| 32 | n-butyl | CH$_3$ | 2-CF$_3$-Ph | —CH—CR[12]—S—CZ— | n-propyl | SO$_2$NHCO$_2$Bu |
| 33 | n-butyl | 2-CH$_3$-Ph | 2-CF$_3$-Ph | —CH—CR[12]—S—CZ— | n-propyl | SO$_2$NHCO$_2$Bu |
| 34 | n-butyl | CH$_3$ | 2-CF$_3$-Ph | —CH—CR[12]—S—CZ— | isobutyl | SO$_2$NHCO$_2$Bu |
| 35 | n-butyl | CH$_3$ | 2-CF$_3$-Ph | —CH—CR[12]—S—CZ— | isobutyl | SO$_2$NHCOPh |
| 36 | n-butyl | CH$_3$ | 2-CF$_3$-Ph | —CH—CR[12]—S—CZ— | isobutyl | SO$_2$NHCOn-pentyl |
| 37 | butyl | CH$_3$ | 2-CF$_3$-Ph | —CH—CR[12]—S—CZ— | ethyl | SO$_2$NHCO$_2$Bu |
| 38 | n-butyl | CH$_3$ | 2-CF$_3$-Ph | —CH—CR[12]—S—CZ— | propyl | SO$_2$NHCONHBu |

TABLE VII

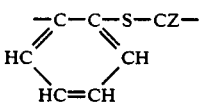

| # | R¹ | R⁸ᵃ | —X¹—X²—X³—X⁴— | R¹² | Z |
|---|---|---|---|---|---|
| 1 | n-butyl | H | —CH—S—CH—CZ— | | 1H-tetrazol-5-yl |
| 2 | n-butyl | Me | —CH—S—CH—CZ— | | 1H-tetrazol-5-yl |
| 3 | n-butyl | N(Me)(CO₂Me) | —CH—S—CH—CZ— | | 1H-tetrazol-5-yl |
| 4 | n-propyl | Me | —CH—S—CH—CZ— | | 1H-tetrazol-5-yl |
| 5 | n-propyl | N(Me)(CO₂Me) | —CH—S—CH—CZ— | | 1H-tetrazol-5-yl |
| 6 | n-butyl | N(Me)(CO₂Me) | —CH—S—CH—CZ— | | SO₂NHCOPh |
| 7 | n-propyl | H | —CH—S—CH—CZ— | | 1H-tetrazol-5-yl |
| 8 | n-propyl | H | —CH—S—CH—CZ— | | SO₂NHCOPh |
| 9 | n-butyl | N(Me)(CO₂Me) | —CH—S—CH—CZ— | | 1H-tetrazol-5-yl |
| 10 | n-butyl | N(Me)(CO₂iBu) | —CH—S—C(SO₂NHCOPh)-CZ— | | 1H-tetrazol-5-yl |
| 11 | n-butyl | CH₃ | —S—CH—CH—CZ— | | SO₂NHCOPh |
| 12 | n-butyl | CH₃ | —CH—CH—S—CZ— | | SO₂NHCOPh |
| 13 | n-propyl | N(Me)(CO₂iBu) | —CH—CH—S—CZ— | | SO₂NHCOPh |
| 14 | n-butyl | CH₃ | —CH—CH—S—CZ— | | 1H-tetrazol-5-yl |
| 15 | n-propyl | N(Bz)(CO₂iBu) | —CH—S—CH—CZ— | | 1H-tetrazol-5-yl |
| 16 | n-butyl | N(Bz)(CO₂Bu) | —CH—S—CH—CZ— | | 1H-tetrazol-5-yl |
| 17 | n-butyl | CH₃ | —CH—S—C(Br)—CZ— | | 1H-tetrazol-5-yl |
| 18 | n-propyl | CH₃ | —CH—S—C(Br)—CZ— | | 1H-tetrazol-5-yl |
| 19 | n-butyl | N(Boz)(Pn) | —CH—CH—S—CZ— | | 1H-tetrazol-5-yl |
| 20 | n-butyl | N(Boz)(Bz) | —CH—CH—S—CZ— | | 1H-tetrazol-5-yl |
| 21 | n-butyl | N(Bz)(CO₂Pn) | —CH—CH—S—CZ— | | 1H-tetrazol-5-yl |
| 22 | n-propyl | N(Me)(CO₂iBu) | —CH—CH—S—CZ— | | 1H-tetrazol-5-yl |
| 23 | n-butyl | N(Me)(CO₂Me) | —CH—CH—O—CZ— | | 1H-tetrazol-5-yl |
| 24 | n-propyl | N(Bz)(CO₂iBu) | —CH—CH—O—CZ— | | 1H-tetrazol-5-yl |
| 25 | n-butyl | N(Boz)(Pn) | —CH—CH—O—CZ— | | 1H-tetrazol-5-yl |
| 26 | n-propyl | N(Bz)(CO₂Bu) | —CH—CH—O—CZ— | | 1H-tetrazol-5-yl |
| 27 | n-butyl | CH₃ | —CH—CH—O—CZ— | | 1H-tetrazol-5-yl |
| 28 | n-propyl | CH₃ | —CH—CH—O—CZ— | | 1H-tetrazol-5-yl |
| 29 | n-propyl | N(Bz)(CO₂iBu) | —CH—S—CH—CZ— | | 1H-tetrazol-5-yl |
| 30 | n-butyl | N(Me)(CO₂Me) | —CH—S—CH—CZ— | | SO₂NHCOCF₃ |
| 31 | n-butyl | N(Bz)(CO₂Me) | —CH—S—CH—CZ— | | CO₂H |
| 32 | n-butyl | CH₃ | —CH—S—C(SO₂NHCOCF₃)—CZ— | | H |
| 33 | n-butyl | CH₃ | —CH—S—C(SO₂NHCOPh)-CZ— | | H |
| 34 | n-butyl | CH₃ | —CH—S—C(SO₂NHCO-4-pyr)-CZ— | | H |
| 35 | n-propyl | N(Bz)[CON(Me)(Et)] | —S—CH—CH—CZ— | | SO₂NHCOPh |
| 36 | n-butyl | N(Bz)[CON(Me)(Et)] | —S—CH—CH—CZ— | | SO₂NHCOPh |
| 37 | n-butyl | N(Me)(CO₂Me) | —S—CH—CH—CZ— | | SO₂NHCOPh |
| 38 | n-butyl | CH₃ | 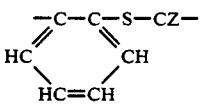 | | SO₂NHCOPh |
| 39 | n-propyl | N(Me)(CO₂Me) | (fused benzo, —C—C—S—CZ—) | | SO₂NHCOPh |
| 40 | n-propyl | NHCOPh | —CH—CR¹²—S—CZ— | n-propyl | SO₂NHCOPh |
| 41 | n-propyl | NHCOPh | —CH—CR¹²—S—CZ— | n-propyl | SO₂NHCOcyPr |
| 42 | n-propyl | NHCOPh | —CH—CR¹²—S—CZ— | isobutyl | SO₂NHCOcyPr |
| 43 | n-propyl | NHCOPh | —CH—CR¹²—S—CZ— | isobutyl | SO₂NHCO₂Bu |
| 44 | n-propyl | NHCOPh | —CH—CR¹²—S—CZ— | isobutyl | SO₂NHCOn-pentyl |
| 45 | n-propyl | NHCOPh | —CH—CR¹²—S—CZ— | isobutyl | SO₂NHCOCH₂OBu |
| 46 | n-propyl | NHCONHEt | —CH—CR¹²—S—CZ— | n-propyl | SO₂NHCO₂Bu |
| 47 | n-propyl | NHCONHEt | —CH—CR¹²—S—CZ— | isobutyl | SO₂NHCO₂Bu |
| 48 | n-propyl | NHCONHEt | —CH—CR¹²—S—CZ— | n-propyl | SO₂NHCO₂(CH₂)₂OMe |
| 49 | n-propyl | NHCONHEt | —CH—CR¹²—S—CZ— | isobutyl | SO₂NHCO₂(CH₂)₂OMe |
| 50 | n-propyl | NHCONHiPr | —CH—CR¹²—S—CZ— | n-propyl | SO₂NHCO₂Bu |
| 51 | n-propyl | NHCONHiPr | —CH—CR¹²—S—CZ— | isobutyl | SO₂NHCO₂Bu |
| 52 | n-propyl | NHCONHiPr | —CH—CR¹²—S—CZ— | n-propyl | SO₂NHCO₂(CH₂)₂OMe |
| 53 | n-propyl | NHCONHiPr | —CH—CR¹²—S—CZ— | isobutyl | SO₂NHCOCH₂OBu |

TABLE VII-continued

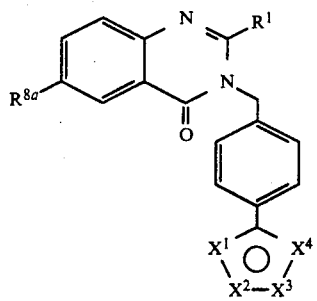

| # | R¹ | R⁸ᵃ | —X¹—X²—X³—X⁴— | R¹² | Z |
|---|---|---|---|---|---|
| 54 | n-propyl | NHCONHiPr | —CH—CR¹²—S—CZ— | CH₂OCH₃ | SO₂NHCO₂Bu |

Abbreviations used: Ph = phenyl; Bz = benzyl; i-Bu = isobutyl; Boz = benzoyl; Bu = n-butyl Pn = n-pentyl; Me = methyl; and Et = ethyl.

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 2-Butyl-6-methyl-3-[[4-[3-(1H-tetrazol-5-yl)-4-thienyl]phenyl]methyl]-quinazolin-4(3H)-one | 50 |
| Lactose | 149 |
| Magnesium stearate | 1 |
| Capsule (size No. 1) | 200 |

The 2-butyl-6-methyl-3-[[4-[3-(1H-tetrazol-5-yl)-thienyl]phenyl]methyl]quinazolin-4(3H)-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical table would contain 2-butyl-6-methyl-3-[[(4-[3-(1H-tetrazol-5-yl)-4-thienyl]phenyl]methyl]-quinazolin-4(3H)-one (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide (25 mg) and 2-butyl-6-methyl-3-[[4-[3-(1H-tetrazol-5-yl)-5-thienyl]phenyl]methyl]quinazolin-4(3H)-one (50 mg) pregelatinized starch USP (82 mg), microcrystalline cellulose (82 mg) and magnesium stearate (1 mg).

D: Suppository

Typical suppository formulations for rectal administration can contain 2-butyl-6-methyl-3-[[4-[3-(1H-tetrazol-5-yl)-4-thienyl]phenyl]methyl]quinazolin-4(3H)-one (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotension converting enzyme and/or a calcium channel blocker in pharmaceutically effective amounts as described, for example, in C above.

E: Injection

A typical injectable formulation would contain 2-butyl-6-methyl-3-[[4-[3-(1H-tetrazol-5-yl)-4-thienyl]-phenyl]methyl]quinazolin-4(3H)-one sodium phosphate dibasic anhydrous (11.4 mg) benzyl alcohol (0.01 ml) and water for injection (1.0 ml). Such as injectable formulation can also include a pharmaceutically effective amount of another active ingredient such as another antihypertensive and/or a diuretic and/or an angiotension converting enzyme inhibitor and/or a calcium channel blocker.

What is claimed is:

1. A compound of structural formula I or its pharmaceutically acceptable salt

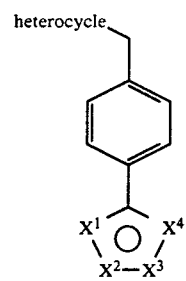

wherein the heterocycle is defined as:

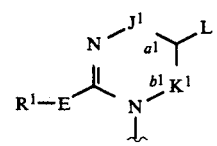

Ia

R¹ is:

(a) ($C_1$-$C_6$)-alkyl, ($C_2$-$C_6$)-alkenyl or ($C_2$-$C_6$)-alkynyl each of which is unsubstituted or substituted with a substituent selected from the group consisting of:
  i) aryl as defined below, ii) $C_3-C_7$)-cycloalkyl,
iii) Cl, Br, I, F,
iv) OH,
v) $NH_2$,
vi) $NH(C_1-C_4)$-alkyl,
vii) $N[(C_1-C_4)$-alkyl$]_2$,
viii) $NHSO_2R^2$,
ix) $CF_3$,
x) $COOR^2$, or
xi) $SO_2NHR^{2a}$;

(b) aryl, wherein aryl is defined as phenyl or naphthyl, unsubstituted or substituted with 1 or 2 substituents selected from the group consisting of:
i) Br, I, Cl, F,
ii) $(C_1-C_4)$-alkyl,
iii) $(C_1-C_4)$-alkoxy,
iv) $NO_2$
v) $CF_3$
vi) $SO_2NR^{2a}R^{2a}$,
vii) $(C_1-C_4)$-alkylthio,
viii) hydroxy,
ix) amino,
x) $(C_3-C_7)$-cycloalkyl, or
xi) $(C_3-C_{10})$-alkenyl;

(c) heteroaryl, wherein heteroaryl is defined as a 5- or 6-membered heteroaromatic moiety, which can contain one or two members selected from the group consisting of N, O, S and wherein the heteroaryl is unsubstituted, monosubstituted or disubstituted with substituents selected from the group consisting of:
i) Cl, Br, I, or F,
ii) OH,
iii) SH,
iv) $NO_2$,
v) $(C_1-C_4)$-alkyl,
vi) $(C_2-C_4)$-alkenyl,
vii) $(C_2-C_4)$-alkynyl,
viii) $(C_1-C_4)$-alkoxy, or
xi) $CF_3$, or (d) $(C_1-C_4)$-polyfluoroalkyl;

E is:
(a) a single bond,
(b) $-S(O)_n(CH_2)_s-$, or
(c) $-O-$;

n is 0 to 2;
s is 0 to 5;

$J^1$ is (a) $-C(=M)-$, (b) $J^1$ and L are connected together to form a 6-carbon aromatic ring substituted with $R^{7a}$, $R^{7b}$, $R^{8a}$ and $R^{8b}$ or (c) $J^1$ and L are connected together to form a 6-membered aromatic ring containing one nitrogen atom not at $J^1$, substituted with $R^{7a}$, $R^{8a}$ and $R^{8b}$;

$K^1$ is (a) $-C(=M)-$, (b) $K^1$ and L are connected together to form a 6-carbon aromatic ring substituted with $R^{7a}$, $R^{7b}$, $R^{8a}$ and $R^{8b}$, or (c) $K^1$ and L are connected together to form a 6-membered aromatic ring containing one nitrogen atom, substituted on the carbon atoms with $R^{7a}$, $R^{8a}$ and $R^{8b}$;

one of $a^1$ or $b^1$ is a double bond in structures Ia provided that when $J^1$ is $-C(=M)-$ then $b^1$ is a double bond and when $K^1$ is $-C(=M)-$ then $a^1$ is a double bond;

L is the point of attachment of the 6-membered fused aromatic ring optionally containing one nitrogen atom;

M is O, S or $NR^{15}$;

$R^2$ is:
(a) H, or
(b) $(C_1-C_6)$-alkyl;

$R^{2a}$ is:
(a) $R^2$,
(b) $CH_2$-aryl, or
(c) aryl;

$R^{2b}$ is:
(a) $R^{2a}$, or
(b) $C_3-C_7$ cycloalkyl;

$R^{2c}$ is:
(a) $-SO_2-(C_1-C_6)$-alkyl;
(b) $-CO-(C_1-C_6)$-alkyl;
(c) $-SO_2-(C_3-C_6)$-cycloalkyl,
(d) $-CO-(C_3-C_6)$-cycloalkyl,
(e) $-SO_2-(C_1-C_4)$-polyfluoroalkyl,
(f) $-CO$-aryl,
(g) $-CO$-polyfluoroaryl,
(h) $-CO$-(2- or 3-thienyl),
(i) $-SO_2-$(2-or 3-thienyl),
(j) $-CO$-(2-, 3- or 4-pyridyl),
(k) $-CONH-(C_1-C_6)$-alkyl,
(l) $-CON[(C_1-C_6)$alkyl$]_2$,
(m) $-CO_2-(C_1-C_6)$-alkyl, or
(n) $-CO_2-(C_3-C_6)$cycloalkyl;

$R^{7a}$ and $R^{7b}$ are independently
(a) H,
(b) $(C_1-C_6)$-alkyl, $(C_2-C_6$-alkenyl or $(C_2-C_6)$-alkynyl,
(c) Cl, Br, I, F,
(d) $CF_3$, or
(e) when $R^{7a}$ and $R^{7b}$ are bonded to adjacent carbon atoms, they can be joined to form a phenyl ring;

$R^{8a}$ and $R^{8b}$ are independently
(a) H,
(b) aryl-$(C_1-C_4)$-alkyl,
(c) heteroaryl-$(C_1-C_4)$-alkyl,
(d) $(C_1-C_6)$-alkyl, which is unsubstituted or substituted with a substituent selected from the group consisting of: $-CON(R^{2a})_2$, $-$heteroaryl, $-S(O)_n-R^{21}$, -tetrazol-5-yl, $-CONSHO_2R^{21}$, $-SO_2NH$-heteroaryl, $-SO_2NHCOR^{21}$, $-PO(OR^2)_2$, $-PO(OR^{2a})_2$, $-SO_2NH$-CN, $-NR^{2a}COOR^{21}$, $-OH$, $-NH_2$, guanidino, $(C_1-C_4)$-alkoxy, $(C_1-C_4)$-alkylthio, $(C_1-C_4)$-alkylamino, $(C_1-C_4)$-dialkylamino, $-COOR^{2a}$, $-CONHR^{2a}$, $-O-COR^{2a}$, aryl, or $$-N\underset{\underline{\phantom{XXX}}}{\overset{\overline{\phantom{XXX}}}{\phantom{XX}}}N-R^{2c};$$

(e) $-CO$-aryl,
(f) $(C_3-C_7)$-cycloalkyl,
(g) Cl, Br, I, F,
(h) $-OH$,
(i) $-OR^{21}$,
(j) $-SH$,
(k) $-S(O)_n-(C_1-C_4)$-alkyl,
(l) $-COR^{2a}$,
(m) $-CO_2H$,
(n) $-SO_3H$,
(o) $-NR^{2a}R^{21}$,
(p) $-NR^{2a}COR^{21}$, (q) —NR$^{2a}$COOR$^{21}$,
(r) —SO$_2$NHR$^{2a}$,
(s) —SO$_2$NR$^2$R$^{2a}$,
(t) —NO$_2$,
(u) —NHSO$_2$CF$_3$,
(v) —CONR$^{2a}$R$^{21}$,
(w) —(C$_1$-C$_4$)-polyfluoroalkyl,
(x) —COOR$^2$,
(y) —SO$_3$H,
(z) —N(R$^{2a}$)SO$_2$R$^{21}$,
(aa) —NR$^{2a}$CONR$^{2b}$R$^{21}$,
(bb) —OC(=O)NR$^{21}$R$^{2a}$,
(cc) —aryl,
(dd) —NHSO$_2$CF$_3$,
(ee) —SO$_2$NH-heteroaryl,
(ff) —SO$_2$NHCOR$^{21}$,
(gg) —CONHSO$_2$R$^{21}$,
(hh) —PO(OR$^2$)$_2$,
(ii) —tetrazol-5-yl,
(jj) —CONH(tetrazol-5-yl),
(kk) —SO$_2$NHCN, or
(ll) —heteroaryl;

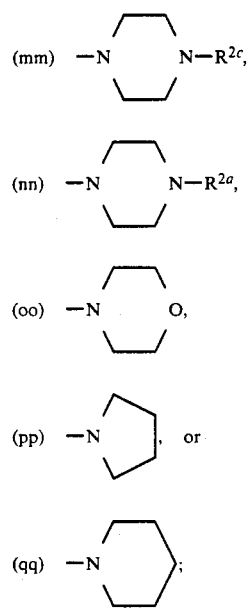

(mm), (nn), (oo), (pp), (qq)

—X$^1$—X$^2$—X$^3$—X$^4$— is:
(a) —Y—CR$^{11}$—CR$^{12}$—CZ—,
(b) —CR$^{11}$—Y—CR$^{12}$—CZ—,
(c) —CR$^{11}$—CR$^{12}$—Y—CZ—,
(d) —Y—CR$^{11}$—CZ—CR$^{12}$—,
(e) —CR$^{11}$—Y—CZ—CR$^{12}$—, or
(f) —CR$^{11}$—CR$^{12}$—CZ—Y—;
Y is: O, S, SO, or SO$_2$;
R$^9$ and R$^{10}$ are each independently:
(a) H,
(b) Cl, Br, I, F,
(c) NO$_2$,
(d) (C$_1$-C$_6$)-alkyl,
(e) (C$_1$-C$_6$)-acyloxy,
(f) (C$_3$-C$_6$)-cycloalkyl,
(g) (C$_1$-C$_6$)-alkoxy,
(h) —NHSO$_2$R$^{2a}$,
(i) hydroxy-(C$_1$-C$_4$)-alkyl,
(j) (C$_1$-C$_4$)-alkyl-aryl,
(k) S(O)$_n$-(C$_1$-C$_4$)-alkyl,
(n) NR$^{2a}$R$^{2a}$,
(q) CF$_3$,
(r) —SO$_2$NHR$^{2a}$,
(s) furyl,
(t) aryl, wherein aryl is phenyl or naphthyl, unsubstituted or substituted with one or two substituents selected from the group consisting of: Cl, Br, I, F, (C$_1$-C$_4$)-alkyl, (C$_1$-C$_4$)-alkoxy, NO$_2$, CF$_3$, (C$_1$-C$_4$)-alkylthio, OH, NH$_2$, —NH[(C$_1$-C$_4$)-alkyl], —N[(C$_1$-C$_4$)-alkyl]$_2$, —CO$_2$H, or —CO$_2$-(C$_1$-C$_4$)-alkyl, or
(u) when R$^9$ and R$^{10}$ are bonded to adjacent carbon atoms, they can be joined to form an aryl ring;
R$^{11}$ and R$^{12}$ are independently:
(a) H,
(b) Cl, Br, I, F,
(c) NO$_2$,
(d) NH$_2$,
(e) NH[(C$_1$-C$_4$)-alkyl],
(f) N[(C$_1$-C$_4$)-alkyl]$_2$,
(g) SO$_2$NHR$^{2a}$,
(h) CF$_3$,
(i) (C$_1$-C$_7$)-alkyl,
(j) (C$_1$-C$_6$)-alkoxy, or
(k) (C$_3$-C$_7$)-cycloalkyl,
(l) when R$^{11}$ and R$^{12}$ are bonded to adjacent carbon atoms, they can be joined to form an aryl ring;
(m) O(CH$_2$)$_{n+1}$O(CH$_2$)$_s$CH$_3$,
(n) (C$_2$)$_{n+1}$O(CH$_2$)$_s$CH$_3$,
(o) (CH$_2$)N(R$^{2a}$)$_2$,
(p) CH$_2$-N[CH$_2$CH$_2$]$_2$O,
(q) (CH$_2$)$_n$N[CH$_2$CH$_2$]$_2$CH$_2$,
(r) CH(OR$^{2a}$)[(C$_1$-C$_7$)-alkyl].
(s) CHO,
(t) CO$_2$R$^{2a}$,
(u) CH=CH—R$^{2a}$,
(v) CH$_2$CR$^{2a}$=C(R$^{2a}$)$_2$,
(w) (CH$_2$)$_n$NCOR$^{2a}$,
(x) (CH$_2$)$_n$aryl, or
(y) CH(R$^{2a}$)$_2$;
Z is:
(a) —CO$_2$R$^{2a}$,
(b) —SO$_3$R$^{13}$,
(c) —NHSO$_2$CF$_3$,
(d) —PO(OR$^{13}$)$_2$,
(e) —SO$_2$NHR$^{2a}$,
(f) —CONHOR$^{13}$, (g) $-\overset{\overset{\text{OH}}{|}}{\underset{\underset{\text{R}^{2a}}{|}}{\text{C}}}-\text{PO(OR}^{13})_2$, (h) —CN,
(i) —SO$_2$NH-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: —OH, —SH, —(C$_1$-C$_4$)-alkyl, —(C$_1$-C$_4$)-alkoxy, —CF$_3$, Cl, Br, F, I, —NO$_2$, —CO$_2$H, —CO$_2$-(C$_1$-C$_4$)-alkyl, —NH$_2$, NH[(C$_1$-C$_4$)-alkyl] and —N[(C$_1$-C$_4$)-alkyl]$_2$,
(j) —CH$_2$SO$_2$NH-heteroaryl,
(k) —SO$_2$NH—CO—R$^{14}$, (l) —CH₂SO₂NH—CO—R¹⁴,
(m) —CONH—SO₂R¹⁴,
(n) —CH₂CONH—SO₂R¹⁴,
(o) —NHSO₂NHCO—R¹⁴,
(p) —NHCONHSO₂—R¹⁴,

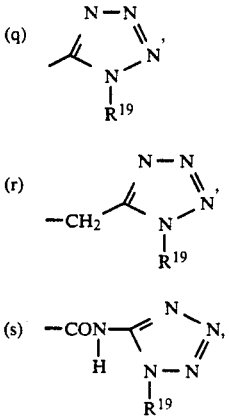

(t) —CONHNHSO₂CF₃,

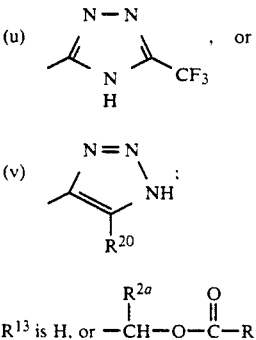

$R^{13}$ is H, or $-\overset{R^{2a}}{\underset{|}{CH}}-O-\overset{O}{\underset{\|}{C}}-R^{2a}$;

$R^{14}$ is
(a) aryl,
(b) heteroaryl,
(c) (C₃-C₇)-cycloalkyl, or
(d) (C₁-C₇)-alkyl, unsubstituted or substituted with a substituent selected from the group consisting of; aryl, heteroaryl, —OH, —SN, (C₁-C₄)-alkyl, —(C₁-C₄)-alkoxy, —S(C₁-C₄)-alkyl, —CF₃, Cl, Br, F, I, —NO₂, —CO₂H, CO₂—(C₁-C₄)-alkyl, —NH₂, —N[(C₁-C₄)-alkyl]₂, —PO₃H or PO-(OH)(O-(C₁-C₄)-alkyl);
(e) (C₁-C₇)-alkoxy,
(f) O(CH₂)ₙ₊₁O(CH₂)ₛCH₃,
(g) (CH₂)ₙ₊₁O(CH₂)ₛCH₃,
(h) CH(R²ᵃ)₂.
(i) (C₁-C₆)-polyfluoroalkyl, or
(j) NH(C₁-C₆)-alkyl;

$R^{15}$ is
(a) H,
(b) aryl, which is unsubstituted or substituted with 1 or 2 substituents selected from the group consisting of: Cl, Br, I, F —O—(C₁-C₄)-alkyl, (C₁-C₄)-alkyl, —NO₂, —CF₃, —SO₂NR²R²ᵃ, —S—(C₁-C₄)—alkyl, —OH, —NH₂, (C₃-C₇)-cycloalkyl, (C₃-C₁₀)-alkenyl;
(c) (C₁-C₆)-alkyl, (C₂-C₆)-alkenyl or (C₂-C₆)-alkynyl each of which is unsubstituted or substituted with one or more substituents selected from the group consisting of: aryl, (C₃-C₇)-cycloalkyl, Cl, Br, I, F, —OH, —NH₂, —NH[(C₁-C₄)-alkyl], —N[(C₁-C₄)-alkyl]₂, —NH—SO₂R²ᵃ, —COOR²ᵃ, —SO₂NHR²ᵃ; or
(d) an unsubstituted, monosubstituted or disubstituted aromatic 5 to 6 membered ring which can contain one or two heteroatoms selected from the group consisting of N, O, S, and wherein the substituents are members selected from the group consisting of —OH, —SH, (C₁-C₄)-alkyl, (C₁-C₄)-alkyloxy, —CF₃, Cl, Br, I, F, or NO₂;

$R^{19}$ is:
(a) H,
(b) (C₁-C₆)-alkyl,
(c) (C₂-C₄)-alkenyl,
(d) (C₁-C₄)-alkoxy, or
(e) benzyl, wherein the phenyl is unsubstituted or substituted with a substituent selected from the group consisting of: —NO₂, —NH₂, —OH or —OCH₃;

$R^{20}$ is —CN, —NO₂, —CO₂R²ᵃ, or —CF₃; and $R^{21}$ is:
(a) aryl, unsubstituted or substituted with a substituent selected from Cl, Br, F or I, or
(b) (C₁-C₄)-alkyl, is unsubstituted or substituted with:
i) NH₂,
ii) NH[(C₁-C₄)-alkyl],
iii) N[(C₁-C₄)-alkyl]₂,
iv) CO₂H,
v) CO₂(C₁-C₄)-alkyl,
vi) OH,
vii) SO₃H, or
viii) SO₂NH₂;
(c) heteroaryl
(d) C₃-C₇ cycloalkyl.
or a pharmaceutically acceptable salt thereof.

2. The compound of claim 1 or its pharmaceutically acceptable salt wherein:
$R^1$ is:
(a) (C₁-C₆)-alkyl or (C₂-C₆)-alkenyl or (C₂-C₆)-alkynyl each of which is unsubstituted or substituted with a substituent selected from the group consisting of:
i) (C₁-C₄)-alkylthio,
ii) (C₁-C₄)-alkoxy,
iii) CF₃,
iv) CF₂CF₃, or
v) (C₃-C₅)-cycloalkyl,
(b) polyfluoro-(C₁-C₄)-alkyl, or
(c) (C₃-C₅)-cyclalkyl;
E is:
(a) single bond,
(b) —S—, or
(c) —O—,
n is 0, 1, or 2;
$J^1$ is (a)—C(=M)—, (b) $J^1$ and L are connected together to form a 6-carbon aromatic ring substituted with R⁷ᵃ, R⁷ᵇ, R⁸ᵃ and R⁸ᵇ or (c) $J^1$ and L are connected together to form a 6-membered aromatic ring containing one nitrogen atom not at $J^1$, substituted with R⁷ᵃ, R⁸ᵃ and R⁸ᵇ;
$K^1$ is (a)—C(=M)—, or (b) $K^1$ and L are connected together to form a 6-carbon aromatic ring substituted with R⁷ᵃ, R⁷ᵇ, R⁸ᵃ and R⁸ᵇ, or (c) $K^1$ and L are connected together to form a six-membered aromatic ring containing one nitrogen atom substituted with R⁷ᵃ, R⁷ᵇ and R⁸ᵇ provided that one and only one of $J^1$ and $K^1$ is —C(=M)—;

one of $a^1$ or $b^1$ is a double bond in structure Ia provided that when $J^1$ is —C(=M)— then $b^1$ is a double bond and when $K^1$ is —C(=M)— then $a^1$ is a double bond;

L is the point of attachment of the 6-membered fused aromatic ring optionally containing one nitrogen atom;

M is O, S or $NR^{15}$;

$R^2$ is:
(a) H,
(b) $(C_1-C_6)$-alkyl;

$R^{2a}$ is:
(a) $R^2$,
(b) $CH_2$aryl, or
(c) aryl;

$R^{2b}$ is;
(a) $R^{2a}$, or
(b) $C_3-C_7$ cycloalkyl;

$R^{2c}$ is:
(a) $-SO_2-(C_1-C_6)$-alkyl,
(b) $-CO-(C_1-C_6)$-alkyl,
(c) $-SO_2-(C_3-C_6)$-cycloalkyl,
(d) $-CO-(C_3-C_6)$-cycloalkyl,
(e) $-SO_2-(C_1-C_4)$-polyfluoroalkyl,
(f) $-CO$-aryl,
(g) $-CO$-polyfluoroaryl,
(h) $-CO-$(2- or 3-thienyl),
(i) $-SO_2$-(2- or 3-thienyl),
(j) $-CO-$(2-, 3- or 4-pyridyl),
(k) $-CONH-(C_1-C_6)$-alkyl,
(l) $-CON[(C_1-C_6)$-alkyl$]_2$,
(m) $-CO_2-(C_1-C_6)$-alkyl, or
(n) $-CO_2-(C_3-C_6)$-cycloalkyl;

$R^{7a}$ and $R^{7b}$ are independently
(a) H,
(b) $(C_1-C_6)$-alkyl, $(C_2-C_6)$-alkenyl or $(C_2-C_6)$-alkynyl,
(c) Cl, Br, I, F,
(d) $CF_3$, or
(e) when $R^{7a}$ and $R^{7b}$ are bonded to adjacent carbon atoms, they can be joined to form a phenyl ring;

$R^{8a}$ and $R^{8b}$ are independently
(a) H,
(b) aryl-$(C_1-C_4)$-alkyl,
(c) heteroaryl-$(C_1-C_4)$-alkyl,
(d) $(C_1-C_6)$-alkyl, is unsubstituted or substituted with a substituent selected from the group consisting of: $-CON(R^{2a})_2$, —heteroaryl, $-S(O)_n-R^{21}$, —tetrazol-5-yl, $-CONHSO_2R^{21}$, $-SO_2NH$-heteroaryl, $-SO_2NHCOR^{21}$, $-PO(OR^2)_2$, $-PO(OR^{2a})_2$, $-SO_2NH-CN$, $-NR^{2a}COOR^{21}$, $-OH$, $-NH_2$, guanidino, $(C_1-C_4)$-alkoxy, $(C_1-C_4)$-alkylthio, $(C_1-C_4)$-alkylamino, $(C_1-C_4)$-dialkylamino, $-COOR^{2a}$, $-CONHR^{2a}$, $-O-COR^{2a}$, aryl, or

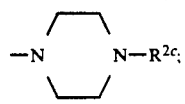

(e) —CO-aryl,
(f) $(C_3-C_7)$-cycloalkyl,
(g) Cl, Br, I, F,
(h) —OH,
(i) $-OR^{21}$, (j) —SH,
(k) $-S(O)_n-(C_1-C_4)$-alkyl,
(l) $-COR^{2a}$,
(m) $-CO_2H$,
(n) $-SO_3H$,
(o) $-NR^{2a}R^{21}$,
(p) $-NR^{2a}COR^{21}$,
(q) $-NR^{2a}COOR^{21}$,
(r) $-SO_2NR^{2a}$,
(s) $-SO_2NR^2R^{2a}$,
(t) $-NO_2$,
(u) $-NHSO_2CF_3$,
(v) $-CONR^{2a}R^{21}$,
(w) $-(C_1-C_4)$-polyfluoroalkyl,
(x) $-COOR^2$,
(y) $-SO_3H$,
(z) $-N(R^{2a})SO_2R^{21}$,
(aa) $-NR^{2a}CONR^{2b}R^{21}$,
(bb) $-OC(=O)NR^{21}R^{2a}$,
(cc) —aryl,
(dd) $-NHSO_2CF_3$,
(ee) $-SO_2NH$-heteroaryl,
(ff) $-SO_2NHCOR^{21}$,
(gg) $-CONHSO_2R^{21}$,
(hh) $-PO(OR^2)_2$,
(ii) -tetrazol-5-yl,
(jj) $-CONH$(tetrazol-5-yl),
(kk) $-SO_2NHCH$,
(ll) -heteroaryl,

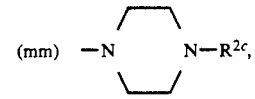

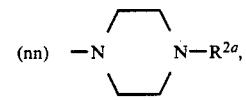

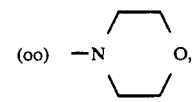

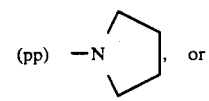

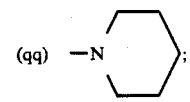

$-X^1-X^2-X^3-X^4-$ is:
(a) $-Y-CR^{11}-CR^{12}-CZ-$,
(b) $-CR^{11}-Y-CR^{12}-CZ-$,
(c) $-CR^{11}-CR^{12}-Y-CZ-$,
(d) $-Y-CR^{11}-CZ-CR^{12}-$,
(e) $-CR^{11}-Y-CZ-CR^{12}-$, or
(f) $-CR^{11}-CR^{12}-CZ-Y-$;

Y is: O, S, SO, or $SO_2$;

$R^9$ and $R^{10}$ are each independently:
(a) H,
(b) Cl, Br, I, F,
(c) $NO_2$,
(d) $(C_1-C_6)$-alkyl, (e) $(C_1-C_6)$-acyloxy,
(f) $(C_3-C_6)$-cycloalkyl,
(g) $(C_1-C_6)$-alkoxy,
(h) —$NHSO_2R^{2a}$,
(k) hydroxy-$(C_1-C_4)$-alkyl,
(j) $(C_1-C_4)$-alkyl-aryl,
(k) $S(O)_n$—$(C_1-C_4)$-alkyl,
(n) $NR^{2a}R^{2a}$,
(q) $CF_3$,
(r) —$SO_2NHR^{2a}$,
(s) furyl,
(t) aryl, wherein aryl is phenyl or naphthyl, unsubstituted or substituted with one or two substituents selected from the group consisting of: Cl, Br, I, F, $(C_1-C_4)$-alkyl, $(C_1-C_4)$-alkoxy, $NO_2$, $CF_3$, $(C_1-C_4)$-alkylthio, OH, $NH_2$, —NH[($C_1-C_4$)-alkyl], —N[$(C_1-C_4)$-alkyl]$_2$, —$CO_2H$, or —$CO_2$—$(C_1-C_4)$-alkyl, or
(u) when $R^9$ and $R^{10}$ are bonded to adjacent carbon atoms, they can be joined to form an aryl ring;
$R^{11}$ and $R^{12}$ are independently:
(a) H,
(b) Cl, Br, I, F,
(c) $NO_2$,
(d) $NH_2$,
(e) NH[$(C_1-C_4)$-alkyl],
(f) N[$(C_1-C_4)$-alkyl]$_2$,
(g) $SO_2NHR^{2a}$,
(h) $CF_3$,
(i) $(C_1-C_7)$-alkyl,
(j) $(C_1-C_6)$-alkoxy,
(k) $(C_3-C_7)$-cycloalkyl,
(l) when $R^{11}$ and $R^{12}$ are bonded to adjacent carbon atoms, they can be joined to form an aryl ring,
(m) $(CH_2)_{n+1}O(CH_2)_sCH_3$,
(n) $(CH_2)_{n+1}O(CH_2)_sCH_3$,
(o) $(CH_2)N(R^{2a})_2$,
(p) $CH_2$—$N[CH_2CH_2]_2O$,
(q) $(CH_2)_nN[CH_2CH_2]_2CH_2$,
(r) $CH(OR^{2a})[(C_1-C_7)$-alkyl],
(s) CHO,
(t) $CO_2R^{2a}$,
(u) CH=CH—$R^{2a}$,
(v) $CH_2CR^{2a}$=C$(R^{2a})_2$,
(w) $(CH_2)_nNCOR^{2a}$,
(x) $(C_1-C_4)$-alkyl-aryl, or
(y) $CH(R^{2a})_2$;
Z is:
(a) —$CO_2R^{2a}$,
(b) —$NHSO_2CF_3$,
(c) —$SO_2NHR^{2a}$,
(d) —CN,
(e) —$SO_2NH$-heteroaryl, wherein heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, —$(C_1-C_4)$-alkyl, —$(C_1-C_4)$-alkoxy, —$CF_3$, Cl, Br, F, I, —$NO_2$, —$CO_2H$, —$CO_2$—$C_1-C_4$-alkyl, —$NH_2$, NH[$(C_1-C_4)$-alkyl] and —N[$(C_1-C_4)$-alkyl]$_2$,
(f) —1H-tetrazol-5-yl.
(g) —$CH_2$—1H-tetrazol-5-yl,
(h) —CONH—1H-tetrazol-5-yl, or
(i) —$SO_2NHCOR^{14}$;
$R^{14}$ is (a) aryl,
(b) heteroaryl,
(c) $(C_3-C_7)$-cycloalkyl, or
(d) $(C_1-C_7)$-alkyl, unsubstituted or substituted with a substituent selected from the group consisting of: aryl, heteroaryl, —OH, —SH, $(C_1-C_4)$-alkyl, —$(C_1-C_4)$-alkoxy, —$S(C_1-C_4)$-alkyl, —$CF_3$, Cl, Br, F, I, —$NO_2$, —$CO_2H$, $CO_2$—$(C_1-C_4)$-alkyl, —$NH_2$, —N[$(C_1-C_4)$-alkyl]$_2$, —$PO_3H$ or PO-(OH)(O-$(C_1-C_4)$-alkyl);
(e) $(C_1-C_7)$-alkoxy,
(f) $O(CH_2)_{n+1}O(CH_2)_sCH_3$,
(g) $(CH_2)_{n+1}O(CH_2)_2CH_3$,
(h) $CH(R^{2a})_2$, or,
(i) —NH—$(C_1-C_6)$-alkyl;
$R^{15}$ is:
(a) H,
(b) aryl, is unsubstituted or substituted with 1 or 2 substituents selected from the group consisting of Cl, Br, I, F, —O—$(C_1-C_4)$-alkyl, $(C_1-C_4)$-alkyl, —$NO_2$, —$CF_3$, —$SO_2NR^2R^{2a}$, —S—$(C_1-C_4)$-alkyl, —OH, —$NH_2$, $(C_3-C_7)$-cycloalkyl, $(C_3-C_{10})$-alkenyl;
(c) $(C_1-C_6)$-alkyl, $(C_2-C_6)$-alkenyl or $(C_2-C_6)$-alkynyl each of which is unsubstituted or substituted with one or more substituents selected from the group consisting of: aryl, $(C_3-C_7)$-cycloalkyl, Cl, Br, I, F, —OH, —NH[$(C_1-C_4)$-alkyl], —N[$(C_1-C_4)$-alkyl]$_2$, —NH—$SO_2R^{2a}$, —$COOR^{2a}$, —$SO_2NHR^{2a}$; or
(d) an unsubstituted, monosubstituted or disubstituted aromatic 5 or 6 membered ring which contains one or two heteroatoms selected from the group consisting of N, O, S, and wherein the substituents are members selected from the group consisting of —OH, —SH, $(C_1-C_4)$-alkyl, $(C_1-C_4)$-alkyloxy —$CF_3$, Cl, Br, I, F, or $NO_2$;
$R^{21}$ is:
(a) aryl, unsubstituted or substituted with a substituent selected from Cl, Br, F or I, or
(b) $(C_1-C_4)$alkyl which is unsubstituted or substituted with:
  i) $NH_2$,
  ii) NH[$(C_1-C_4)$-alkyl],
  iii) N[$(C_1-C_4)$-alkyl]$_2$,
  iv) $CO_2H$,
  v) $CO_2(C_1-C_4)$-alkyl,
  vi) OH,
  vii) $SO_3H$, or
  viii) $SO_2NH_2$,
(c) heteroaryl, or
(d) $(C_3-C_7)$-cycloalkyl.

3. The compound of claim 1 or its pharmaceutically acceptable salt wherein:
$R^1$ is:
(a) $(C_1-C_6)$-alkyl $(C_2-C_6)$-alkenyl or $(C_2-C_6)$-alkynyl each of which is unsubstituted or substituted with a substituent selected from the group consisting of:
  i) $(C_1-C_4)$-alkylthio,
  ii) $(C_1-C_4)$-alkoxy,
  iii) $CF_3$,
  iv) $CF_2CF_3$, or
  v) $(C_3-C_5)$-cycloalkyl, or
(b) $(C_1-C_4)$-polyfluoroalkyl;
E is a single bond;
n is 0 to 2;

$J^1$ and L are connected together to form a 6-carbon aromatic ring substituted with $R^{7a}$, $R^{7b}$, $R^{8a}$ and $R^{8b}$; or $J^1$ and L are connected together to form a 6-membered aromatic ring containing one nitrogen atom not at $J^1$, substituted with $R^{7a}$, $R^{8a}$ and $R^{8b}$;

$K^1$ is —C(=M)—;

$a^1$ is a double bond;

L is the point of attachment of the 6-membered fused aromatic ring optionally containing one nitrogen atom;

M is O, or $NR^{15}$;

$R^2$ is:
(a) H,
(b) $(C_1-C_6)$-alkyl, or
(c) $(C_1-C_6)$-alkyl;

$R^{2a}$ is:
(a) $R^2$,
(b) benzyl, or
(c) phenyl;

$R^{2b}$ is:
(a) $R^{2a}$, or
(b) $(C_3-C_7)$ cycloalkyl;

$R^{2c}$ is:
(a) —$SO_2$—$(C_1-C_6)$-alkyl,
(b) —CO—$(C_1-C_6)$-alkyl,
(c) —$SO_2$—$(C_3-C_6)$-cycloalkyl,
(d) —CO—$(C_3-C_6)$-cycloalkyl,
(e) —$SO_2$—$(C_1-C_4)$-polyfluoroalkyl,
(f) —CO-aryl,
(g) —CO-polyfluoroaryl,
(h) —Co-(2- or 3-thienyl),
(i) —$SO_2$-(2- or 3-thienyl),
(j) —CO-(2-, 3- or 4-pyridyl),
(k) —CONH-$(C_1-C_6)$-alkyl,
(l) —CON[$(C_1-C_6)$-alkyl]$_2$,
(m) —$CO_2$-$(C_1-C_6)$-alkyl, or
(n) —$CO_2$-$(C_3-C_6)$-cycloalkyl;

$R^{7a}$ and $R^{7b}$ are independently;
(a) H,
(b) $(C_1-C_6)$-alkyl, $(C_2-C_6)$-alkenyl or $(C_2-C_6)$-alkynyl.
(c) Cl, Br, I, F,
(d) $CF_3$, or
(e) when $R^{7a}$ and $R^{7b}$ are bonded to adjacent carbon atoms, they can be joined to form a phenyl ring;

$R^{8a}$ and $R^{8b}$ are independently:
(a) H,
(b) aryl-$(C_1-C_4)$-alkyl,
(c) heteroaryl-$(C_1-C_4)$-alkyl,
(d) $(C_1-C_6)$-alkyl, unsubstituted or substituted with a substituent selected from the group consisting of: —CON$(R^{2a})_2$, -heteroaryl, —S(O)$_n$-$R^{21}$, -tetrazol-5-yl, —$CONHSO_2R^{21}$, —$SO_2NH$-heteroaryl, —$SO_2NHCOR^{21}$, —$PO(OR^2)_2$, —PO(OR$^{2a}$)$_2$, —$SO_2NH$—CN, —$NR^{2a}COOR^{21}$, —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^{2a}$, —$CONHR^{2a}$, —O—$COR^{2a}$, aryl, or

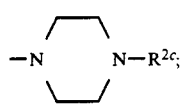

(e) —CO-aryl,
(f) $(C_3-C_7)$-cycloalkyl,
(g) Cl, Br, I, F,
(h) —OH,
(i) —$OR^{21}$,
(j) —SH,
(k) —S(O)$_n$—$(C_1-C_4)$-alkyl,
(l) —$COR^{2a}$,
(m) —$CO_2H$,
(n) —$SO_3H$,
(o) —$NR^{2a}R^{21}$,
(p) —$NR^{2a}COR^{21}$,
(q) —$NR^{2a}COOR^{21}$,
(r) —$SO_2NR^{2a}$,
(s) —$SO_2NR^2R^{2a}$,
(t) —$NO_2$,
(u) —$NHSO_2CF_3$,
(v) —$CONR^{2a}R^{21}$,
(w) —$(C_2-C_4)$-polyfluoroalkyl,
(x) —$COOR^2$,
(y) —$SO_3H$,
(z) —$N(R^{2a})SO_2R^{21}$,
(aa) —$NR^{2a}CONR^{2b}R^{21}$,
(bb) —OC(=O)$NR^{21}R^{2a}$,
(cc) -aryl,
(dd) —$NHSO_2CF_3$,
(ee) —$SO_2NH$-heteroaryl,
(ff) —$SO_2NHCOR^{21}$,
(gg) —$CONHSO_2R^{21}$,
(hh) —$PO(OR^2)_2$,
(ii) -tetrazol-5-yl,
(jj) —CONH(tetrazol-5-yl),
(kk) —$SO_2NHCN$,
(ll) -heteroaryl, (mm) 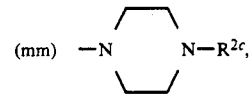

(nn) 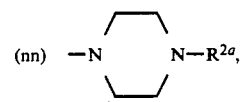

(oo) 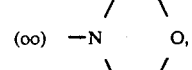

(pp) 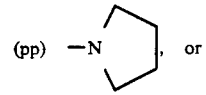, or (qq) 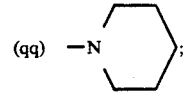;

—$X^1$—$X^2$—$X^3$—$X^4$— is;
(a) —Y—$CR^{11}$—$CR^{12}$—CZ—,
(b) —$CR^{11}$—Y—$CR^{12}$—DZ—,
(c) —$CR^{11}$—$CR^{12}$—Y—CZ—,
(d) —Y—$CR^{11}$—CZ—$CR^{12}$—,
(e) —$CR^{11}$—Y—CZ—$CR^{12}$—, or
(f) —$CR^{11}$—$CR^{12}$—CZ—Y—;

Y is: O or S;

n is: 0 to 2;
R[11] and R[12] are independently:
 (a) H,
 (b) Cl, Br, I, F,
 (c) NH$_2$,
 (d) NH[(C$_1$-C$_4$)-alkyl],
 (e) N[(C$_1$-C$_4$)-alkyl]$_2$
 (f) SO$_2$NHR$^{2a}$,
 (g) CF$_3$,
 (h) (C$_1$-C$_7$)-alkyl,
 (i) (C$_1$-C$_4$)-alkoxy, or
 (j) (C$_3$-C$_6$)-cycloalkyl;
Z is:
 (a) —CO$_2$R$^{2a}$,
 (b) —NHSO$_2$CF$_3$,
 (c) —SO$_2$NHR$^{14}$,
 (d) —1H-tetrazol-5-yl,
 (e) —SO$_2$NHCOR$^{14}$, or
 (f) —NHSO$_2$R$^{14}$;
R$^{14}$ is (a) aryl,
 (b) heteroaryl,
 (c) (C$_3$-C$_7$)-cycloalkyl,
 (d) (C$_1$-C$_4$)-alkyl, unsubstituted or substituted with a substituted selected from the group consisting of aryl as defined above, heteroaryl as defined above, —OH, —SH, (C$_1$-C$_4$)-alkyl, —(C$_1$-C$_4$)-alkoxy, —S(C$_1$-C$_4$)-alkyl, —CF$_3$, Cl, Br, F, I, —NO$_2$, —CO$_2$H, CO$_2$—(C$_1$-C$_4$)-alkyl, —NH$_2$, —N[(C$_1$-C$_4$)-alkyl]$_2$, —PO$_3$H, PO(OH)(O-(C$_1$-C$_4$)-alkyl);
 (e) (C$_1$-C$_7$)-alkoxy,
 (f) O(CH$_2$)$_{n+1}$O(CH$_2$)$_5$CH$_3$,
 (g) (CH$_2$)$_{n+1}$O(CH$_2$)$_5$CH$_3$,
 (h) CH(R$^{2a}$)$_2$,
 (i) (C$_1$-C$_6$)-polyfluoroalkyl, or
 (j) —NH(C$_1$-C$_6$)-alkyl;
R$^{15}$ is:
 (a) H,
 (b) aryl, unsubstituted or substituted with 1 or 2 substituents selected from the group consisting of: Cl, Br, I, F —O—(C$_1$-C$_4$)-alkyl, (C$_1$-C$_4$)-alkyl, —NO$_2$, —CF$_3$, —SO$_2$NR$^2$R$^{2a}$, —S—(C$_1$-C$_4$)-alkyl, —OH, —NH$_2$, (C$_3$-C$_7$)-cycloalkyl, (C$_3$-C$_{10}$)-alkenyl;
 (c) (C$_1$-C$_6$)-alkyl, (C$_2$-C$_6$)-alkenyl or (C$_2$-C$_6$)-alkynyl each of which is unsubstituted or substituted with one or more substituents selected from the group consisting of aryl as defined above, (C$_3$-C$_6$)-cyclalkyl, Cl, Br, I, F, —OH, —NH$_2$, —NH[(C$_1$-C$_4$)-alkyl], —N[(C$_1$-C$_4$)-alkyl]$_2$, —NH—SO$_2$R$^{2a}$, —COOR$^{2a}$, —SO$_2$NHR$^{2a}$; or
 (d) an unsubstituted, monosubstituted or disubstituted aromatic 5 or 6 membered ring which can contain one or two heteroatoms selected from the group consisting of N, O, S, and wherein the substituents are members selected from the group consisting of: —OH, —SH, (C$_1$-C$_4$)-alkyl, (C$_1$-C$_4$)-alkyloxy, —CF$_3$, Cl, Br, I, F, or NO$_2$; and
R$^{21}$ is
 (a) aryl, unsubstituted or substituted with a substituent selected from Cl, Br, F, or I, or
 (b) (C$_1$-C$_4$)-alkyl which is unsubstituted of substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H,
  viii) SO$_2$NH$_2$,
 (c) heteroaryl, or
 (d) (C$_3$-C$_7$)-cycloalkyl.
4. The compound of claim 1 of structural formula

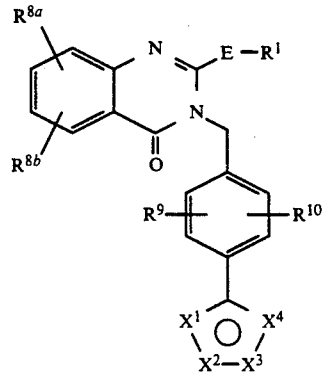

or a pharmaceutically acceptable salt thereof.

5. The compound of claim 1 or its pharmaceutically acceptable salt in which the structural formula is

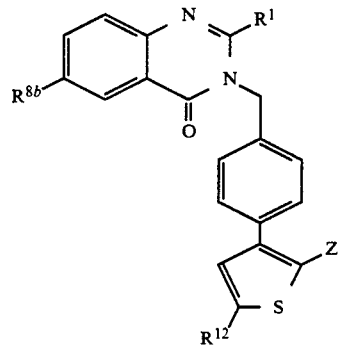

wherein
R$^1$ is: ethyl, n-propyl, n-butyl or n-pentyl;
R$^{2c}$ is:
 (a) —SO$_2$—(C$_1$-C$_6$)-alkyl,
 (b) —CO—(C$_1$-C$_6$)-alkyl,
 (c) —SO$_2$—(C$_3$-C$_6$)-cycloalkyl,
 (d) —CO—(C$_3$-C$_6$)-cycloalkyl,
 (e) —SO$_2$—(C$_1$-C$_4$)-polyfluoroalkyl,
 (f) —CO-aryl,
 (g) —CO-polyfluoroaryl,
 (h) —CO—(2- or 3-thienyl),
 (i) —SO$_2$—(2- or 3-thienyl),
 (j) —CO—(2-, 3- or 4-pyridyl),
 (k) —CONH-(C$_1$-C$_6$)-alkyl,
 (l) —CON[(C$_1$-C$_6$)-alkyl]$_2$,
 (m) —CO$_2$-(C$_1$-C$_6$)-alkyl, or
 (n) —CO$_2$-(C$_3$-C$_6$)-cycloalkyl;
R$^{8b}$ is:
 N(n-butyl)CO-phenyl,
 N(pentyl)CO-phenyl,
 N(benzyl))CO-phenyl,
 N(benzyl)CO$_2$-isobutyl,
 N(pentyl)CO-4-pyridyl,
 N(pentyl)CO-(4-chlorophenyl), N(n-butyl)CO-(4-fluorophenyl),
N(methyl)CO2-isobutyl,
isopropyl,
N(benzyl)CON(methyl)(ethyl), or

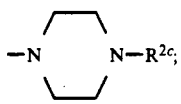

R$^{12}$ is:
H, (C$_1$–C$_6$)-alkyl, benzyl, or

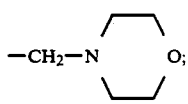

Z is:
(a) CO$_2$R$^2$,
(b) 1H-tetrazol-5-yl,
(c) CONHSO$_2$R$^{14}$,
(d) SO$_2$NHR$^{14}$,
(e) NHSO$_2$R$^{14}$,
(f) SO$_2$NHCOR$^{14}$, or
(g) NHSO$_2$CF$_3$; and
R$^{14}$ is:
(a) phenyl,
(b) (C$_1$–C$_6$)-alkyl,
(c) (C$_1$–C$_6$)-alkoxy,
(d) CH$_2$phenyl,
(f)

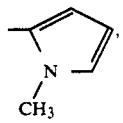

(g) (C$_3$–C$_7$)-cycloalkyl,
(h) (C$_1$–C$_3$)-alkyl-(C$_3$–C$_6$)-cycloalkyl,
(i) (CH$_2$)$_5$NH$_2$,
(j) O(CH$_2$)$_{n+1}$O(CH$_2$)$_5$CH$_3$.
(k) (CH$_{2n+1}$O(CH$_2$)$_5$CH$_3$, or
(j) —NH(C$_1$–C$_6$)-alkyl.

6. A pharmaceutical composition useful in the treatment of hypertension which comprises a pharmaceutically acceptable carrier and a therapeutically effective amount of a compound of claim 1.

7. A method of treating hypertension which comprises administering to a patient in need of such treatment a therapeutically effective amount of a compound of claim 1.

8. An ophthalmological formulation for the treatment of ocular hypertension comprising an ophthalmologically acceptable carrier and an effective ocular antihypertensive amount of a compound of claim 1.

9. A method of treating ocular hypertension comprising topical ocular administration to a patient in need of such treatment of an effective ocular antihypertensive amount of a compound of claim 1.

10. A compound of structural formula I

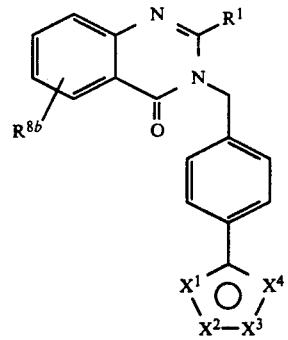

or its pharmaceutically acceptable salt thereof.
wherein:
R$^1$ is: ethyl, n-propyl, n-butyl or n-pentyl;
—X$^1$—X$^2$—X$^3$—X$^4$— is:
(a) —Y—CR$^{11}$—CR$^{12}$—CZ,
(b) —CR$^{11}$—Y—CR$^{12}$—CZ—, or
(c) —CR$^{11}$—CR$^{12}$—Y—CZ;
Y is: O or S;
R$^{8b}$ is:
(a) H,
(b) CH$_3$,
(c) N(CH$_3$)(CO$_2$CH$_3$),
(d) N(CH$_3$)(CO$_2$iBu),
(e) N(Bz)(CO$_2$iBu),
(f) N(Bz)(CO$_2$Bu),
(g) N(Boz)(nPn),
(h) N(Boz)(Bz),
(i) N(Bz)(CO$_2$CH$_3$),
(j) N(Bz)]CON(CH$_3$)(Et)],
(k) NHCOnPn,
(l) NHCONHEt, or
(m) NHCONHiPr;
Z is:
(a) tetrazol-5-yl,
(b) SO$_2$NHCOPh,
(c) SO$_2$NHCOCF$_3$,
(d) SO$_2$NHCOcyPr,
(e) SO$_2$NHCO$_2$Bu,
(f) SO$_2$NHCOnPn,
(g) SO$_2$NHCOCH$_2$OBu, or
(h) SO$_2$NHCO$_2$(CH$_2$)$_2$OCH$_3$; and
R$^{11}$ and R$^{12}$ are:
(a) both H,
(b) when R$^{11}$ and R$^{12}$ are bonded to adjacent carbon atoms, they can be joined to form a phenyl ring; or
(c) when R$^{11}$ is H, R$^{12}$ is (C$_1$–C$_6$)-alkyl, benzyl or CH$_2$—[CH$_2$CH$_2$]$_2$O.

11. A compound or its pharmaceutically acceptable salt in which the structural formula is:

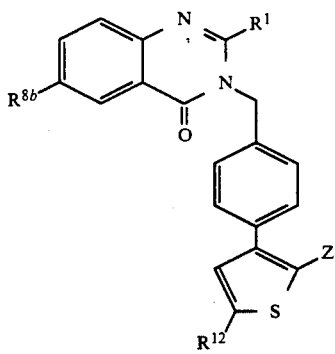

and wherein
$R^1$ is: ethyl, n-propyl, n-butyl or n-pentyl;
$R^2$ is: H or $(C_1-C_6)$-alkyl;
$R^{2c}$ is:
(a) $-SO_2-(C_1-C_6)$-alkyl,
(b) $-CO-(C_1-C_6)$-alkyl,
(c) $-SO_2-(C_3-C_6)$-cycloalkyl,
(d) $-CO-(C_3-C_6)$-cycloalkyl,
(e) $-SO_2-(C_1-C_4)$-polyfluoroalkyl,
(f) $-CO$-aryl,
(g) $-CO$-polyfluoroaryl,
(h) $-CO$-(2- or 3-thienyl),
(i) $-SO_2$-(2- or 3-thienyl),
(j) $-CO$-(2-, 3- or 4- pyridyl),
(k) $-CONH-(C_1-C_6)$-alkyl,
(l) $-CON[(C_1-C_6)$-alkyl$]_2$,
(m) $-CO_2-(C_1-C_6)$-alkyl, or
(n) $-CO_2-(C_3-C_6)$-cycloalkyl;
n is: 0, 1 or 2;
s is: 0 to 5;
$R^{8b}$ is:
N(n-butyl)CO-phenyl,
N(pentyl)CO-phenyl,
N(benzyl))CO-phenyl,
N(benzyl)CO$_2$-isobutyl,
N(pentyl)CO-4-pyridyl,
N(pentyl)CO-(4-chlorophenyl),
N(n-butyl)CO-(4-fluorophenyl),
N(methyl)CO$_2$-isobutyl,
isopropyl,
N(benzyl)CON(methyl)(ethyl), or

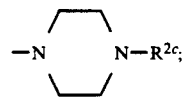

$R^{12}$ is:
H, $(C_1-C_6)$-alkyl, benzyl, or

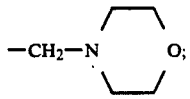

Z is:
(a) $CO_2R^2$,
(b) 1H-tetrazol-5-yl,
(c) $CONHSO_2R^{14}$,
(d) $SO_2NHR^{14}$,
(e) $NHSO_2R^{14}$,
(f) $SO_2NHCOR^{14}$, or
(g) $NHSO_2CF_3$; and
$R^{14}$ is:
(a) phenyl,
(b) $(C_1-C_6)$-alkyl,
(c) $(C_1-C_6)$-alkoxy,
(d) CH$_2$phenyl,
(f)

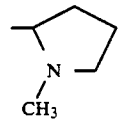

(g) $(C_3-C_7)$-cycloalkyl,
(h) $(C_1-C_3)$-alkyl-$(C_3-C_6)$-cycloalkyl,
(i) $(CH_2)_5NH_2$,
(j) $O(CH_2)_{n+1}O(CH_2)_sCH_3$,
(k) $(CH_2)_{n+1}O(CH_2)_sCH_3$, or
(j) $-NH(CH_1-C_6)$-alkyl.

* * * * *